US011304946B2

(12) United States Patent
Lefranc et al.

(10) Patent No.: US 11,304,946 B2
(45) Date of Patent: Apr. 19, 2022

(54) 2-HETARYLPYRIMIDINE-4-CARBOXAMIDES AS ARYL HYDROCARBON RECEPTOR ANTAGONISTS

(71) Applicants: Bayer Aktiengesellschaft, Leverkusen (DE); Bayer Pharma Aktiengesellschaft, Berlin (DE); Deutsches Krebsforschungszentrum, Heidelberg (DE)

(72) Inventors: Julien Lefranc, Berlin (DE); Norbert Schmees, Berlin (DE); Ulrike Röhn, Berlin (DE); Ludwig Zorn, Berlin (DE); Judith Günther, Berlin (DE); Ilona Gutcher, Berlin (DE); Lars Röse, Berlin (DE); Benjamin Bader, Berlin (DE); Detlef Stöckigt, Potsdam (DE); Michael Platten, Heidelberg (DE)

(73) Assignees: Bayer Aktiengesellschaft, Leverkusen (DE); Bayer Pharma Aktiengesellschaft, Berlin (DE); Deutsches Krebsforschungszentrum, Heidelberg (DE)

( * ) Notice: Subject to any disclaimer, the term of this patent is extended or adjusted under 35 U.S.C. 154(b) by 23 days.

(21) Appl. No.: 16/765,778

(22) PCT Filed: Nov. 16, 2018

(86) PCT No.: PCT/EP2018/081543
§ 371 (c)(1),
(2) Date: May 20, 2020

(87) PCT Pub. No.: WO2019/101641
PCT Pub. Date: May 31, 2019

(65) Prior Publication Data
US 2020/0289509 A1    Sep. 17, 2020

(30) Foreign Application Priority Data
Nov. 21, 2017 (EP) .................................... 17202887

(51) Int. Cl.
C07D 401/04 (2006.01)
C07D 401/14 (2006.01)
C07D 403/04 (2006.01)
C07D 405/14 (2006.01)
C07D 409/04 (2006.01)
C07D 409/14 (2006.01)
C07D 413/04 (2006.01)
A61K 31/506 (2006.01)

(52) U.S. Cl.
CPC .......... A61K 31/506 (2013.01); C07D 401/04 (2013.01); C07D 401/14 (2013.01); C07D 403/04 (2013.01); C07D 405/14 (2013.01); C07D 409/04 (2013.01); C07D 409/14 (2013.01); C07D 413/04 (2013.01)

(58) Field of Classification Search
CPC .. C07D 403/04; C07D 401/04; C07D 409/04; C07D 413/04; C07D 401/14; C07D 409/14; C07D 405/14; A61K 31/506
See application file for complete search history.

(56) References Cited

U.S. PATENT DOCUMENTS

| 5,418,233 A | 5/1995 | Linz |
| 2014/0023623 A1 | 1/2014 | Peled |

FOREIGN PATENT DOCUMENTS

| EP | 1953147 A1 | 8/2008 |
| WO | WO2006084017 A2 | 8/2006 |
| WO | WO2006084017 A3 | 12/2006 |
| WO | WO2007058392 A1 | 5/2007 |
| WO | WO2007128723 A1 | 11/2007 |
| WO | WO2008009963 A2 | 1/2008 |
| WO | WO2008009963 A3 | 5/2008 |
| WO | WO2010059401 A2 | 5/2010 |
| WO | WO2010059401 A3 | 9/2010 |
| WO | WO2012015914 A2 | 2/2012 |
| WO | WO2012015914 A3 | 5/2012 |

OTHER PUBLICATIONS

Andersson, P. et al. (2002). "A constitutively active dioxin/aryl hydrocarbon receptor induces stomach tumors," PNAS 99(15): 9990-9995.
Bui, L-C. et al. (2009). "Nedd9/Hef1/Cas-L mediates the effects of environmental pollutants on cell migration and plasticity," Oncogene 28: 3642-3651.
Bushuev, M.B. et al. (2011). "Zinc(II) and cadmium(II) complexes based on 2-(3,5-dimethyl-1H-pyrazol-1-yl)-6-(4-methoxyphenyl)pyrimidine-4-carboxylic acid: Synthesis, structure and luminescence," Inorganic Chemistry Communications 14: 749-752.

(Continued)

Primary Examiner — Susanna Moore
(74) Attorney, Agent, or Firm — Morrison & Foerster LLP

(57) ABSTRACT

The present invention covers 2-hetarylpyrimidine-4-carboxamide compounds of general formula (I): in which X, Y, Z, $R^1$, $R^2$ and $R^4$ are as defined herein, methods of preparing said compounds, intermediate compounds useful for preparing said compounds, pharmaceutical compositions and combinations comprising said compounds and the use of said compounds for manufacturing pharmaceutical compositions for the treatment or prophylaxis of diseases, in particular of cancer or conditions with dysregulated immune responses or other disorders associated with aberrant AHR signaling, as a sole agent or in combination with other active ingredients.

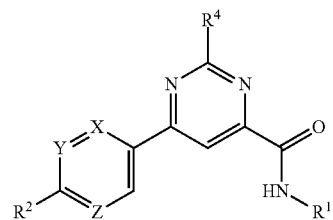

(I)

11 Claims, No Drawings

(56) References Cited

OTHER PUBLICATIONS

Dinatale, B.C. et al. (2010). "Kynurenic Acid Is a Potent Endogenous Aryl Hydrocarbon Receptor Ligand that Synergistically Induces Interleukin-6 in the Presence of Inflammatory Signaling," Toxicological Sciences 115(1): 89-97.

Esser, C. et al. (2009). "The aryl hydrocarbon receptor in immunity," Trends in Immunology 30(9): 447-454.

Gramatzki, D. et al. (2009). "Aryl hydrocarbon receptor inhibition downregulates the TGF-β/Smad pathway in human glioblastoma cells," Oncogene 28: 2593-2605.

International Search Report dated Jan. 2, 2019 for PCT Application No. PCT/EP2018/081543 filed Nov. 16, 2018, 3 pages.

Liu, X. et al. (2010). "Selective inhibition of IDO1 effectively regulates mediators of antitumor immunity," Blood 115(17): 3520-3530.

Metz, R. et al. (2007). "Novel Tryptophan Catabolic Enzyme IDO2 Is the Preferred Biochemical Target of the Antitumor Indoleamine 2,3-Dioxygenase Inhibitory Compound D-1-Methyl-Tryptophan," Cancer Res 67(15): 7082-7087.

Mezrich, J.D. et al. (2010). "An Interaction between Kynurenine and the Aryl Hydrocarbon Receptor Can Generate Regulatory T Cells," J Immunol 185(6): 3190-3198.

Muller, A.J. et al. (2005). "Inhibition of indoleamine 2,3-dioxygenase, an immunoregulatory target of the cancer suppression gene Bin1, potentiates cancer chemotherapy," Nature Medicine 11(3): 312-319.

Nguyen, L.P. et al. (2008). "The Search for Endogenous Activators of the Aryl Hydrocarbon Receptor," Chem. Res. Toxicol. 21: 102-116.

Nguyen, N.T. et al. (2010). "Aryl hydrocarbon receptor negatively regulates dendritic cell immunogenicity via a kynurenine-dependent mechanism," PNAS 107(46): 19961-19966.

Nguyen, N.T. et al. (2014). "Aryl hydrocarbon receptor and kynurenine: recent advances in autoimmune disease research," Frontiers in Immunology 5(551): 1-6.

Opitz, C.A. et al. (2011). "An endogenous tumour-promoting ligand of the human aryl hydrocarbon receptor," Nature 478: 197-203.

Reyes, H. et al. (1992). "Identification of the Ah Receptor Nuclear Translocator Protein (Arnt) as a Component of the DNA Binding Form of the Ah Receptor," Science 256: 1193-1195.

Uyttenhove, C. et al. (2003). "Evidence for a tumoral immune resistance mechanism based on tryptophan degradation by indoleamine 2,3-dioxygenase," Nature Medicine 9(10): 1269-1274.

Wang, C. et al. (2014). "Activation of the aryl hydrocarbon receptor affects activation and function of human monocyte-derived dendritic cells," Clinical and Experimental Immunology 117: 521-530.

Wei, P. et al. (2014). "An aryl hydrocarbon receptor ligand acts on dendritic cells and T cells to suppress the Th17 response in allergic rhinitis patients," Laboratory Investigation 94: 528-535.

Yamada, T. et al. (2016). "Constitutive aryl hydrocarbon receptor signaling constrains type I interferon-mediated antiviral innate defense," Nature Immunology 17(6): 687-694.

2-HETARYLPYRIMIDINE-4-CARBOXAMIDES AS ARYL HYDROCARBON RECEPTOR ANTAGONISTS

CROSS REFERENCE TO RELATED APPLICATIONS

This application is a national stage application under 35 U.S.C. § 371 of International Application No. PCT/EP2018/081543, filed internationally on Nov. 16, 2018, which claims the benefit of priority to European Application No. 17202887.0, filed Nov. 21, 2017.

The present invention covers 2-hetarylpyrimidine-4-carboxamide compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular cancer or conditions with dysregulated immune responses, as a sole agent or in combination with other active ingredients.

BACKGROUND

The AHR (Aryl Hydrocarbon Receptor) is a ligand-activated transcription factor, belonging to the basic helix-loop-helix/Per-Arnt-Sim (bHLH/PAS) family, and is located in the cytosol. Upon ligand binding, the AHR translocates to the nucleus where it heterodimerises with ARNT (AHR Nuclear Translocator) upon which it interacts with DREs (Dioxin Response Elements) of AHR-responsive genes to regulate their transcription. The AHR is best known for binding to environmental toxins and inducing the metabolic machinery, such as cytochrome P 450 enzymes (eg. CYP1A1, CYP1A2 and CYP1B1), required for their elimination (Reyes et al., Science, 1992, 256(5060): 1193-5). Activation of AHR by xenobiotics has demonstrated its role in numerous cellular processes such as embryogenesis, tumourigenesis and inflammation.

AHR is expressed in many cells of the immune system, including dendritic cells (DCs), macrophages, T cells and NK cells, and plays an important role in immunoregulation (Nguyen et al., Front Immunol, 2014, 5: 551). The classic exogenous AHR ligands TCDD and 3-methylcholanthrene, for example, are known to induce profound immunosuppression, promote carcinogenesis and induce tumour growth (Gramatzki et al., Oncogene, 2009, 28(28): 2593-605; Bui et al., Oncogene, 2009, 28(41): 3642-51; Esser et al., Trends Immunol, 2009, 30: 447-454). In the context of immunosuppression, AHR activation promotes regulatory T cell generation, inhibits Th1 and Th17 differentiation, directly and indirectly, and decreases the activation and maturation of DCs (Wang et al., Clin Exp Immunol, 2014, 177(2): 521-30; Mezrich et al., J Immunol, 2010, 185(6): 3190-8; Wei et al., Lab Invest, 2014, 94(5): 528-35; Nguyen et al., PNAS, 2010, 107(46): 19961-6). AHR activation modulates the innate immune response and constitutive AHR expression has been shown to negatively regulate the type-I interferon response to viral infection (Yamada et al., Nat Immunol, 2016). Additionally, mice with a constitutively active AHR spontaneously develop tumours (Andersson et al., PNAS, 2002, 99(15): 9990-5).

In addition to xenobiotics, the AHR can also bind metabolic products of tryptophan degradation. Tryptophan metabolites, such as kynurenine and kynurenic acid, are endogenous AHR ligands that activate the AHR under physiological conditions (DiNatale et al., Toxicol Sci, 2010, 115(1): 89-97; Mezrich et al., J Immunol, 2010, 185(6): 3190-8; Opitz et al., Nature, 2011, 478(7368): 197-203). Other endogenous ligands are known to bind the AHR although their physiological roles are currently unknown (Nguyen & Bradfield, Chem Res Toxicol, 2008, 21(1): 102-116).

The immunosuppressive properties of kynurenine and tryptophan degradation are well described and are implicated in cancer-associated immunosuppression. The enzymes indoleamine-2,3-dioxygenases 1 and 2 (IDO1/IDO2) as well as tryptophan-2,3-dioxygenase 2 (TDO2) are responsible for catalysing the first and rate-limiting step of tryptophan metabolism. IDO1/2-mediated degradation of tryptophan in tumours and tumour-draining lymph nodes reduces anti-tumour immune responses and inhibition of IDO can suppress tumour formation in animal models (Uyttenhove et al., Nat Med, 2003, 9(10): 1269-74; Liu et al., Blood, 2005, 115(17): 3520-30; Muller et al., Nat Med, 11(3): 312-9; Metz, Cancer Res, 2007, 67(15): 7082-7087).

TDO2 is also strongly expressed in cancer and can lead to the production of immunosuppressive kynurenine. In glioma, activation of the AHR by kynurenine, downstream of TDO-mediated tryptophan degradation, enhances tumour growth as a consequence of inhibiting anti-tumour immune responses as well as directly promoting tumour cell survival and motility (Opitz et al., Nature, 2011, 478(7368): 197-203). AHR ligands generated by tumour cells therefore act in both an autocrine and paracrine fashion on tumour cells and lymphocytes, respectively, to promote tumour growth.

The present invention covers 2-hetarylpyrimidine-4-carboxamide compounds of general formula (I) which inhibit the AHR.

State of the Art

WO 2010/059401 relates to compounds and compositions for expanding the number of CD34+ cells for transplantation. In particular, WO 2010/059401 relates inter alia to heterocyclic compounds capable of down-regulating the activity and/or expression of AHR.

WO 2012/015914 relates to compositions and methods for modulating AHR activity. In particular, WO 2012/015914 relates inter alia to heterocyclic compounds that modulate AHR activity for use in therapeutic compositions.

WO 2007/058392 relates to novel heterocyclic compounds and a pharmaceutical use thereof. In particular, WO 2007/058392 relates inter alia to heterocyclic compounds having an hepatitis C virus cell infection inhibitory activity.

U.S. Pat. No. 5,418,233 relates to heterobiaryl derivatives inhibiting cell-cell aggregation and cell-matrix interactions. In particular, U.S. Pat. No. 5,418,233 relates to heterobiaryl derivatives which are histamine receptor antagonists.

WO 2008/009963 relates to pyrimidine derivatives. In particular, WO 2008/009963 relates to parathyroid hormone and parathyroid hormone related protein receptor ligands.

However, the state of the art does not describe the 2-hetarylpyrimidine-4-carboxamide compounds of general formula (I) of the present invention as described and defined herein.

It has now been found, and this constitutes the basis of the present invention, that the compounds of the present invention have surprising and advantageous properties.

In particular, the compounds of the present invention have surprisingly been found to effectively inhibit AHR for which data are given in biological experimental section and may therefore be used for the treatment or prophylaxis of cancer or other conditions where exogenous and endogenous AHR ligands induce dysregulated immune responses, uncontrolled cell growth, proliferation and/or survival of tumour cells, immunosuppression in the context of cancer, inappropriate cellular immune responses, or inappropriate cellular inflammatory responses or diseases which are accompanied with uncontrolled cell growth, proliferation and/or survival of tumour cells, immunosuppression in the context of cancer inappropriate cellular immune responses, or inappropriate cellular inflammatory responses, particularly in which the uncontrolled cell growth, proliferation and/or survival of tumour cells, immunosuppression in the context of cancer, inappropriate cellular immune responses, or inappropriate cellular inflammatory responses is mediated by AHR, such as, for example, liquid and solid tumours, and/or metastases thereof, e.g. head and neck tumours including brain tumours and brain metastases, tumours of the thorax including non-small cell and small cell lung tumours, gastrointestinal tumours including colon, colorectal and pancreatic tumours, liver tumours, endocrine tumours, mammary and other gynecological tumours, urological tumours including renal, bladder and prostate tumours, skin tumours, and sarcomas, and/or metastases thereof.

DESCRIPTION OF THE INVENTION

In accordance with a first aspect, the present invention covers compounds of general formula (I):

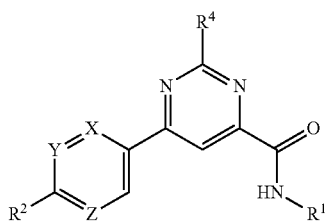

(I)

in which
X represents CH or N;
Y represents $CR^3$ or N;
Z represents CH or N, wherein
    if X represents N, Y represents $CR^3$ and Z represents CH, and
    if X represents CH, Z represents CH and Y represents $CR^3$ or N, and
    if Z represents N, Y represents N and X represents CH;
$R^1$ represents $C_2$-$C_8$-hydroxyalkyl, wherein said $C_2$-$C_8$-hydroxyalkyl groups are optionally substituted once with $R^7$ and optionally one to three times with halogen, or
    $C_3$-$C_6$-cycloalkyl substituted once with hydroxy or $C_1$-$C_3$-hydroxyalkyl and optionally one to three times with halogen, or
    ($C_3$-$C_6$-cycloalkyl substituted once with hydroxy)-$C_1$-$C_4$-alkyl, or
    5- to 6-membered heterocycloalkyl optionally substituted once with hydroxy or $C_1$-$C_3$-hydroxyalkyl and optionally one to three times with halogen, or
    (5- to 6-membered heterocycloalkyl optionally substituted once with hydroxy)-$C_1$-$C_4$-alkyl;
$R^2$ represents hydrogen, chloro, methyl, fluoromethyl, difluoromethyl, trifluoromethyl, methoxy, difluoromethoxy, trifluoromethoxy or —$NR^8R^9$;
$R^3$ represents hydrogen, halogen or methyl;
$R^4$ represents monocyclic heteroaryl optionally substituted one to three times, independently from each other, with $R^5$;
$R^5$ represents $C_1$-$C_4$-alkyl, $C_1$-$C_4$-haloalkyl, $C_3$-$C_6$-cycloalkyl, $C_1$-$C_4$-alkoxy, halogen or cyano;
$R^7$ represents $C_1$-$C_4$-alkoxy, —$CO_2$—$R^{10}$, —CO—$NR^8R^9$, cyano, —$NR^8R^9$, $C_3$-$C_6$-cycloalkyl, 5- to 6-membered heterocycloalkyl, phenyl or monocyclic heteroaryl;
$R^8$ and $R^9$ are the same or different and represent, independently from each other, hydrogen or $C_1$-$C_3$-alkyl, or together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;
$R^{10}$ represents hydrogen or $C_1$-$C_4$-alkyl;
their polymorphs, enantiomeres, diastereomeres, racemates, tautomeres, N-oxides, hydrates and solvates, as well as their physiological acceptable salts and solvates of these salts, as well as mixtures of the same.

Further, it covers their use in combination with other anti cancer medications such as immunotherapeutics, targeted anti cancer agents or chemotherapy.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon atom. Commonly, it is possible for the number of optional substituents, when present, to be 1, 2 or 3.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen" means a fluorine, chlorine, bromine or iodine, particularly a fluorine, chlorine or bromine atom.

The term "$C_2$-$C_8$-alkyl" means a linear or branched, saturated, monovalent hydrocarbon group having 2, 3, 4, 5, 6, 7 or 8 carbon atoms, e.g. a ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl, 1,3-dimethylbutyl, 3-ethyl-pentyl or 3-ethyl-hexyl group, or an isomer thereof. Particularly, said group has 2, 3 or 4 carbon atoms ("$C_2$-$C_4$-alkyl"), e.g. a ethyl, propyl, isopropyl, butyl, sec-butyl isobutyl, or tert-butyl group, more particularly 2 or 3 carbon atoms ("$C_2$-$C_3$-alkyl"), e.g. a ethyl, n-propyl or isopropyl group.

The term "$C_2$-$C_8$-hydroxyalkyl" means a linear or branched, saturated, monovalent hydrocarbon group in which the term "$C_2$-$C_8$-alkyl" is defined supra, and in which 1 or 2 hydrogen atoms are replaced with a hydroxy group, e.g. a 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methylpropyl, 2-hydroxy-2-methyl-propyl, 1-hydroxy-2-methylpropyl, 3-ethyl-2-hydroxypentyl or 3-ethyl-2-hydroxyhexyl group.

The term "$C_1$-$C_4$-alkoxy" means a linear or branched, saturated, monovalent group of formula ($C_1$-$C_4$-alkyl)-O—, which means methoxy, ethoxy, n-propoxy, isopropoxy, n-butoxy, sec-butoxy, isobutoxy or tert-butoxy.

The term "$C_3$-$C_6$-cycloalkyl" means a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is a monocyclic hydrocarbon ring, e.g. a cyclopropyl, cyclobutyl, cyclopentyl or cyclohexyl.

The term "5- to 6-membered heterocycloalkyl" means a monocyclic, saturated heterocycle with 5 or 6 ring atoms in total, which contains a heteroatom-containing group selected from the group consisting of —$NR^8$—, —O—, —S—, —SO—, —$SO_2$—, —$SO_2$—$NR^8$—, —SO (=$NR^8$)—, wherein $R^8$ means a hydrogen atom or a $C_1$-$C_3$-alkyl group. It being possible for said heterocycloalkyl group to be attached to the rest of the molecule via any one of the carbon atoms or, if present, a nitrogen atom.

Said heterocycloalkyl group, without being limited thereto, can be a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, tetrahydrothiophene 1-oxide, 1,2-thiazolidine 1-oxide, 1,3-thiazolidine 1-oxide, tetrahydrothiophene 1,1-dioxide, 1,2-thiazolidine 1,1-dioxide, 1,3-thiazolidine 1,1-dioxide, 1,2,5-thiadiazolidine 1,1-dioxide, 1,2,4-thiadiazolidine 1,1-dioxide, 1,2,3-thiadiazolidine 1,1-dioxide, tetrahydro-1H-1$\lambda^4$-thiophen-1-imine 1-oxide, 1$\lambda^4$,2-thiazolidin-1-imine 1-oxide or 1$\lambda^4$,3-thiazolidin-1-imine 1-oxide, for example; or a 6 membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, tetrahydro-2H-thiopyran 1-oxide, 1,2-thiazinane 1-oxide, 1,3-thiazinane 1-oxide, thiomorpholine 1-oxide, tetrahydro-2H-thiopyran 1,1-dioxide, 1,2-thiazinane 1,1-dioxide, 1,3-thiazinane 1,1-dioxide, thiomorpholine 1,1-dioxide, 1,2,6-thiadiazinane 1,1-dioxide, 1,2,5-thiadiazinane 1,1-dioxide, 1,2,4-thiadiazinane 1,1-dioxide, 1,2,3-thiadiazinane 1,1-dioxide, hexahydro-1$\lambda^4$-thiopyran-1-imine 1-oxide, 1$\lambda^4$,2-thiazinan-1-imine 1-oxide, 1$\lambda^4$,3-thiazinan-1-imine 1-oxide or 1$\lambda^4$-thiomorpholin-1-imine 1-oxide, for example.

The term "monocyclic heteroaryl" means a monovalent, aromatic ring having 5 or 6 ring atoms (a "5- or 6-membered heteroaryl" group), which contains at least one ring heteroatom and optionally one or two further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly, the heteroaryl group is a pyrazolyl or pyridinyl group.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown. Unless specified otherwise, suffixes to chemical names or structural formulae relating to salts, such as "hydrochloride", "trifluoroacetate", "sodium salt", or "x HCl", "x CF$_3$COOH", "x Na$^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

The invention further includes all possible crystallized and polymorphic forms of the inventive compounds, whereby the polymorphs are existing either as a single polymorph form or are existing as a mixture of several polymorphs in all concentrations.

The compounds are either commercially available or can be prepared according to procedures available from the public domain, as understandable to the person skilled in the art. Specific examples are described in the Experimental Section.

In accordance with a second embodiment of the first aspect, the present invention covers compounds of general formula (I), supra, in which:

X represents CH;
Y represents $CR^3$;
Z represents CH;
$R^1$ represents $C_2$-$C_6$-hydroxyalkyl, wherein said $C_2$-$C_6$-hydroxyalkyl groups are optionally substituted once with $R^7$ and optionally one to three times with fluoro, or
$C_4$-$C_6$-cycloalkyl substituted once with hydroxy and optionally one to two times with fluoro, or
($C_4$-$C_6$-cycloalkyl substituted once with hydroxy)-methyl, or
4-hydroxyoxolan-3-yl, 4-hydroxythiolan-3-yl or 4-hydroxy-1,1-dioxo-1lambda$^6$-thiolan-3-yl;
$R^2$ represents chloro, difluoromethyl, trifluoromethyl or trifluoromethoxy;
$R^3$ represents hydrogen;
$R^4$ represents a group selected from:

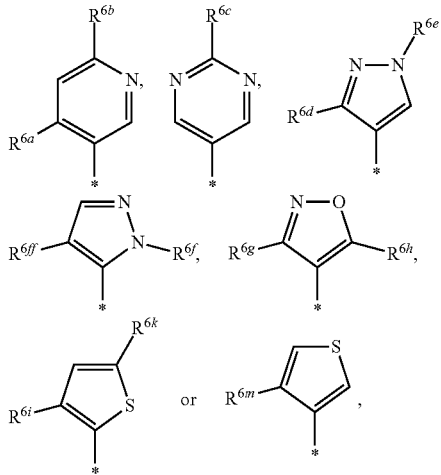

wherein * indicates the point of attachment of said group with the rest of the molecule;
$R^{6a}$ represents hydrogen or methoxy;
$R^{6b}$ represents hydrogen, methyl, methoxy or cyano;
$R^{6c}$ represents hydrogen, chloro, methyl or cyano;
$R^{6d}$ represents hydrogen or methyl;
$R^{6e}$ represents hydrogen, methyl, isobutyl or cyclopropyl;
$R^{6f}$ represents hydrogen or methyl;
$R^{6ff}$ represents hydrogen or methyl;
$R^{6g}$ represents hydrogen or methyl;
$R^{6h}$ represents hydrogen or methyl;
$R^{6i}$ represents hydrogen or methyl;
$R^{6k}$ represents hydrogen, chloro or cyano;
$R^{6m}$ represents hydrogen or methyl;
$R^7$ represents cyano, $C_3$-$C_4$-cycloalkyl or pyridinyl;

their polymorphs, enantiomeres, diastereomeres, racemates, tautomeres, N-oxides, hydrates and solvates, as well as their physiological acceptable salts and solvates of these salts, as well as mixtures of the same.

In accordance with a third embodiment of the first aspect, the present invention covers compounds of general formula (I), supra, in which:
X represents CH or N;
Y represents $CR^3$ or N;
Z represents CH or N, wherein
if X represents N, Y represents $CR^3$ and Z represents CH, and
if X represents CH, Z represents CH and Y represents $CR^3$ or N, and
if Z represents N, Y represents N and X represents CH;
$R^1$ represents $C_2$-$C_8$-hydroxyalkyl, wherein said $C_2$-$C_8$-hydroxyalkyl groups are optionally substituted once with $R^7$ and optionally one to three times with halogen, or
$C_3$-$C_6$-cycloalkyl substituted once with hydroxy or $C_1$-$C_3$-hydroxyalkyl and optionally one to three times with halogen, or
($C_3$-$C_6$-cycloalkyl substituted once with hydroxy)-$C_1$-$C_4$-alkyl, or
5- to 6-membered heterocycloalkyl which contains a heteroatom-containing group selected from the group consisting of —$NR^8$—, —O— or —S— substituted once with hydroxy or
$C_1$-$C_3$-hydroxyalkyl and optionally one to three times with halogen, or
5- to 6-membered heterocycloalkyl which contains a heteroatom-containing group selected from the group consisting of —SO—, —$SO_2$—, —$SO_2$—$NR^8$— or —SO(=$NR^8$)— optionally substituted once with hydroxy or $C_1$-$C_3$-hydroxyalkyl and optionally one to three times with halogen, or
(5- to 6-membered heterocycloalkyl optionally substituted once with hydroxy)-$C_1$-$C_4$-alkyl;
$R^2$ represents hydrogen, chloro, methyl, fluoromethyl, difluoromethyl, trifluoromethyl, methoxy, difluoromethoxy, trifluoromethoxy or —$NR^8R^9$;
$R^3$ represents hydrogen, halogen or methyl;
$R^4$ represents a group selected from:

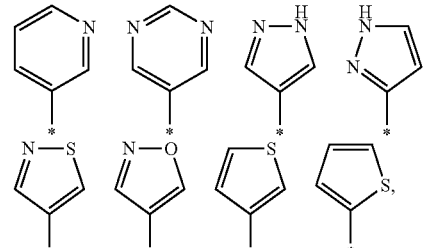

wherein * indicates the point of attachment of said group with the rest of the molecule and said group is optionally substituted one to three times, independently from each other, with $R^5$;
$R^5$ represents $C_1$-$C_4$-alkyl, $C_1$-$C_4$-haloalkyl, $C_3$-$C_6$-cycloalkyl, $C_1$-$C_4$-alkoxy, halogen or cyano;
$R^7$ represents $C_1$-$C_4$-alkoxy, —$CO_2$—$R^{10}$, —CO—$NR^8R^9$, cyano, —$NR^8R^9$, $C_3$-$C_6$-cycloalkyl, 5- to 6-membered heterocycloalkyl, phenyl or monocyclic heteroaryl;
$R^3$ and $R^9$ are the same or different and represent, independently from each other, hydrogen or $C_1$-$C_3$-alkyl, or
together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;
$R^{10}$ represents hydrogen or $C_1$-$C_4$-alkyl;

their polymorphs, enantiomeres, diastereomeres, racemates, tautomeres, N-oxides, hydrates and solvates, as well as their physiological acceptable salts and solvates of these salts, as well as mixtures of the same.

In accordance with a forth embodiment of the first aspect, the present invention covers compounds of general formula (I), supra, in which:
X represents CH;
Y represents $CR^3$;
Z represents CH;
$R^1$ represents $C_2$-$C_6$-hydroxyalkyl, wherein said $C_2$-$C_6$-hydroxyalkyl groups are optionally substituted once with $R^7$ and optionally one to three times with fluoro, or
$C_4$-$C_6$-cycloalkyl substituted once with hydroxy and optionally one to two times with fluoro, or
($C_4$-$C_6$-cycloalkyl substituted once with hydroxy)-methyl, or
4-hydroxyoxolan-3-yl, 4-hydroxythiolan-3-yl or 4-hydroxy-1,1-dioxo-1lambda$^6$-thiolan-3-yl;
$R^2$ represents chloro, difluoromethyl, trifluoromethyl or trifluoromethoxy;
$R^3$ represents hydrogen;
$R^4$ represents a group selected from:

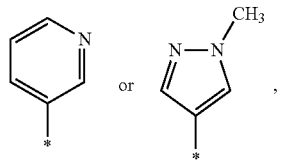

wherein * indicates the point of attachment of said group with the rest of the molecule;
$R^7$ represents cyano, $C_3$-$C_4$-cycloalkyl or pyridinyl;
their polymorphs, enantiomeres, diastereomeres, racemates, tautomeres, N-oxides, hydrates and solvates, as well as their physiological acceptable salts and solvates of these salts, as well as mixtures of the same.

In accordance with a second aspect, the present invention covers methods of preparing compounds of general formula (I) as defined supra, said methods comprising the step of allowing an intermediate compound of general formula (VII):

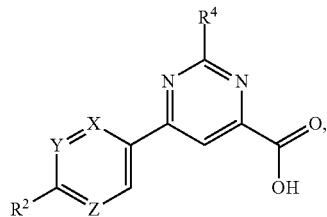

in which
X represents CH or N;
Y represents $CR^3$ or N;
Z represents CH or N, wherein
  if X represents N, Y represents $CR^3$ and Z represents CH, and
  if X represents CH, Z represents CH and Y represents $CR^3$ or N, and
  if Z represents N, Y represents N and X represents CH;
$R^2$ represents hydrogen, chloro, methyl, fluoromethyl, difluoromethyl, trifluoromethyl, methoxy, difluoromethoxy, trifluoromethoxy or —$NR^8R^9$;
$R^3$ represents hydrogen, halogen or methyl;
$R^4$ represents monocyclic heteroaryl optionally substituted one to three times, independently from each other, with $R^5$;

$R^5$ represents $C_1$-$C_4$-alkyl, $C_1$-$C_4$-haloalkyl, $C_3$-$C_6$-cycloalkyl, $C_1$-$C_4$-alkoxy, halogen or cyano;
$R^8$ and $R^9$ are the same or different and represent, independently from each other, hydrogen or $C_1$-$C_3$-alkyl, or
together with the nitrogen atom to which they are attached form a 4- to 6-membered nitrogen containing heterocyclic ring, said ring optionally containing one additional heteroatom selected from O, S, NH, $NR^a$ in which $R^a$ represents a $C_1$-$C_4$-alkyl group;
to react with a compound of general formula (VIII):

$$H_2N\text{—}R^1 \qquad (VIII),$$

in which
$R^1$ represents $C_2$-$C_8$-hydroxyalkyl, wherein said $C_2$-$C_8$-hydroxyalkyl groups are optionally substituted once with $R^7$ and optionally one to three times with halogen, or
$C_3$-$C_6$-cycloalkyl substituted once with hydroxy or $C_1$-$C_3$-hydroxyalkyl and optionally one to three times with halogen, or
($C_3$-$C_6$-cycloalkyl substituted once with hydroxy)-$C_1$-$C_4$-alkyl, or
5- to 6-membered heterocycloalkyl optionally substituted once with hydroxy or $C_1$-$C_3$-hydroxyalkyl and optionally one to three times with halogen, or
(5- to 6-membered heterocycloalkyl optionally substituted once with hydroxy)-$C_1$-$C_4$-alkyl in which $R^7$ is as defined supra.
thereby giving a compound of general formula (I):

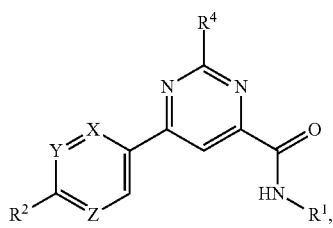

in which X, Y, Z, $R^1$, $R^2$ and $R^4$ are as defined supra.

The present invention covers methods of preparing compounds of the present invention of general formula (I), said methods comprising the steps as described in the Experimental Section herein.

In accordance with a third aspect, the present invention covers intermediate compounds which are useful for the preparation of the compounds of general formula (I), supra.

Particularly, the inventions covers the intermediate compounds of general formula (VII):

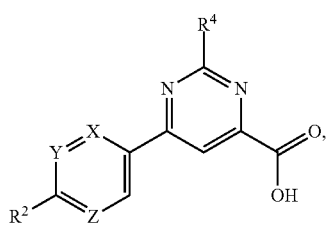

in which
X represents CH or N;
Y represents $CR^3$ or N;
Z represents CH or N, wherein
  if X represents N, Y represents $CR^3$ and Z represents CH, and if X represents CH, Z represents CH and Y represents CR$^3$ or N, and if Z represents N, Y represents N and X represents CH;

R$^2$ represents hydrogen, chloro, methyl, fluoromethyl, difluoromethyl, trifluoromethyl, methoxy, difluoromethoxy, trifluoromethoxy or —NR$^8$R$^9$;

R$^3$ represents hydrogen, halogen or methyl;

R$^4$ represents monocyclic heteroaryl optionally substituted one to three times, independently from each other, with R$^5$;

R$^5$ represents C$_1$-C$_4$-alkyl, C$_1$-C$_4$-haloalkyl, C$_3$-C$_6$-cycloalkyl, C$_1$-C$_4$-alkoxy, halogen or cyano;

R$^8$ and R$^9$ are the same or different and represent, independently from each other, hydrogen or C$_1$-C$_3$-alkyl, or together with the nitrogen atom to which they are attached form a 4- to 6-membered nitrogen containing heterocyclic ring, said ring optionally containing one additional heteroatom selected from O, S, NH, NR$^a$ in which R$^a$ represents a C$_1$-C$_4$-alkyl group;

In accordance with a forth aspect, the present invention covers the use of said intermediate compounds for the preparation of a compound of general formula (I) as defined supra.

Particularly, the inventions covers the use of intermediate compounds of general formula (VII):

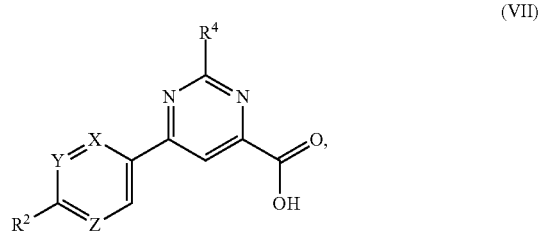

(VII)

in which
X represents CH or N;
Y represents CR$^3$ or N;
Z represents CH or N, wherein
if X represents N, Y represents CR$^3$ and Z represents CH, and
if X represents CH, Z represents CH and Y represents CR$^3$ or N, and
if Z represents N, Y represents N and X represents CH;

R$^2$ represents hydrogen, chloro, methyl, fluoromethyl, difluoromethyl, trifluoromethyl, methoxy, difluoromethoxy, trifluoromethoxy or —NR$^8$R$^9$;

R$^3$ represents hydrogen, halogen or methyl;

R$^4$ represents monocyclic heteroaryl optionally substituted one to three times, independently from each other, with R$^5$;

R$^5$ represents C$_1$-C$_4$-alkyl, C$_1$-C$_4$-haloalkyl, C$_3$-C$_6$-cycloalkyl, C$_1$-C$_4$-alkoxy, halogen or cyano;

R$^8$ and R$^9$ are the same or different and represent, independently from each other, hydrogen or C$_1$-C$_3$-alkyl, or together with the nitrogen atom to which they are attached form a 4- to 6-membered nitrogen containing heterocyclic ring, said ring optionally containing one additional heteroatom selected from O, S, NH, NR$^a$ in which R$^a$ represents a C$_1$-C$_4$-alkyl group;

for the preparation of a compound of general formula (I) as defined supra.

The present invention covers the intermediate compounds which are disclosed in the Example Section of this text, infra.

In a further embodiment of the first aspect, the present invention covers compounds of formula (I), supra, in which:
R$^1$ represents C$_2$-C$_8$-hydroxyalkyl, wherein said C$_2$-C$_8$-hydroxyalkyl groups are optionally substituted once with W and optionally one to three times with halogen, or C$_3$-C$_6$-cycloalkyl substituted once with hydroxy or C$_1$-C$_3$-hydroxyalkyl and optionally one to three times with halogen, or (C$_3$-C$_6$-cycloalkyl substituted once with hydroxy)-C$_1$-C$_4$-alkyl, or 5- to 6-membered heterocycloalkyl optionally substituted once with hydroxy or C$_1$-C$_3$-hydroxyalkyl and optionally one to three times with halogen, or (5- to 6-membered heterocycloalkyl optionally substituted once with hydroxy)-C$_1$-C$_4$-alkyl;

their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
R$^1$ represents C$_2$-C$_8$-hydroxyalkyl, wherein said C$_2$-C$_8$-hydroxyalkyl groups are optionally substituted once with R$^7$ and optionally one to three times with halogen, or C$_3$-C$_6$-cycloalkyl substituted once with hydroxy or C$_1$-C$_3$-hydroxyalkyl and optionally one to three times with halogen, or (C$_3$-C$_6$-cycloalkyl substituted once with hydroxy)-C$_1$-C$_4$-alkyl, or 5- to 6-membered heterocycloalkyl which contains a heteroatom-containing group selected from the group consisting of —NR$^8$—, —O— or —S— substituted once with hydroxy or C$_1$-C$_3$-hydroxyalkyl and optionally one to three times with halogen, or 5- to 6-membered heterocycloalkyl which contains a heteroatom-containing group selected from the group consisting of —SO—, —SO$_2$—, —SO$_2$—NR$^8$— or —SO(=NR$^8$)— optionally substituted once with hydroxy or C$_1$-C$_3$-hydroxyalkyl and optionally one to three times with halogen, or (5- to 6-membered heterocycloalkyl optionally substituted once with hydroxy)-C$_1$-C$_4$-alkyl;

their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
R$^1$ represents C$_2$-C$_8$-hydroxyalkyl, wherein said C$_2$-C$_8$-hydroxyalkyl groups are optionally substituted once with W and optionally one to three times with halogen, or C$_3$-C$_6$-cycloalkyl substituted once with hydroxy or C$_1$-C$_3$-hydroxyalkyl and optionally one to three times with halogen, or (C$_3$-C$_6$-cycloalkyl substituted once with hydroxy)-C$_1$-C$_4$-alkyl;

their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
R$^1$ represents C$_2$-C$_6$-hydroxyalkyl, wherein said C$_2$-C$_6$-hydroxyalkyl groups are optionally substituted once with R$^7$ and optionally one to three times with fluoro, or C$_4$-C$_6$-cycloalkyl substituted once with hydroxy and optionally one to two times with fluoro, or (C$_4$-C$_6$-cycloalkyl substituted once with hydroxy)-methyl, or 4-hydroxyoxolan-3-yl, 4-hydroxythiolan-3-yl or 4-hydroxy-1,1-dioxo-1lambda⁶-thiolan-3-yl;
   their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
$R^1$ represents 5- to 6-membered heterocycloalkyl which contains a heteroatom-containing group selected from the group consisting of —$NR^8$—, —O— or —S— substituted once with hydroxy or $C_1$-$C_3$-hydroxyalkyl and optionally one to three times with halogen;
   their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
$R^1$ represents 5- to 6-membered heterocycloalkyl which contains a heteroatom-containing group selected from the group consisting of —SO—, —$SO_2$—, —$SO_2$—$NR^8$— or —SO(=$NR^8$)— optionally substituted once with hydroxy or $C_1$-$C_3$-hydroxyalkyl and optionally one to three times with halogen;
   their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
$R^1$ represents (5- to 6-membered heterocycloalkyl optionally substituted once with hydroxy)-$C_1$-$C_4$-alkyl;
   their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
$R^1$ represents $C_3$-$C_4$-hydroxyalkyl, wherein said $C_3$-$C_4$-hydroxyalkyl groups are optionally substituted one to three times with fluoro;
   their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
$R^2$ represents hydrogen, chloro, methyl, fluoromethyl, difluoromethyl, trifluoromethyl, methoxy, difluoromethoxy, trifluoromethoxy or —$NR^8R^9$;
   their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
$R^2$ represents chloro, difluoromethyl, trifluoromethyl or trifluoromethoxy;
   their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
$R^4$ represents monocyclic heteroaryl optionally substituted one to three times, independently from each other, with $R^5$;
   their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
$R^4$ represents a group selected from:

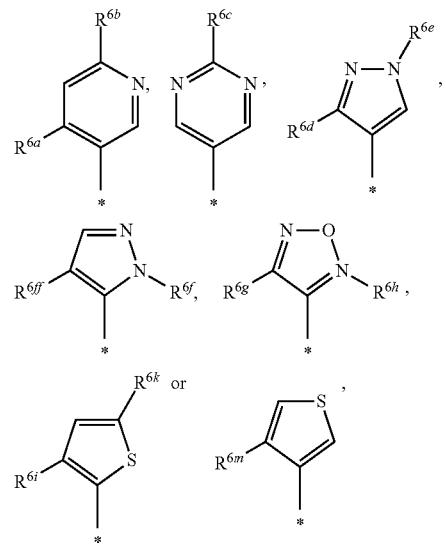

wherein * indicates the point of attachment of said group with the rest of the molecule;
   their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
$R^4$ represents a group selected from:

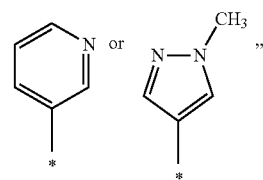

wherein * indicates the point of attachment of said group with the rest of the molecule;
   their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
$R^7$ represents $C_1$-$C_4$-alkoxy, —$CO_2$—$R^{10}$, —CO—$NR^8R^9$, cyano, —$NR^8R^9$, $C_3$-$C_6$-cycloalkyl, 5- to 6-membered heterocycloalkyl, phenyl or monocyclic heteroaryl;
   their polymorphs, enantiomeres, diastereomeres, racemates, tautomeres, N-oxides, hydrates and solvates, as well as their physiological acceptable salts and solvates of these salts, as well as mixtures of the same.

In a further embodiment of the first aspect, the present invention covers compounds of formula (I), supra, in which:
$R^7$ represents cyano, $C_3$-$C_4$-cycloalkyl or pyridinyl;
   their polymorphs, enantiomeres, diastereomeres, racemates, tautomeres, N-oxides, hydrates and solvates, as well as their physiological acceptable salts and solvates of these salts, as well as mixtures of the same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of intermediate compounds of general formula (VII), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

The compounds according to the invention of general formula (I) can be prepared according to the following scheme 1. The scheme and procedures described below illustrate synthetic routes to the compounds of general formula (I) of the invention and are not intended to be limiting. It is clear to the person skilled in the art that the order of transformations as exemplified in scheme 1 can be modified in various ways. The order of transformations exemplified in this scheme is therefore not intended to be limiting. In addition, interconversion of any of the substituents $R^1$, $R^2$, $R^3$, $R^4$ or $R^5$ can be achieved before and/or after the exemplified transformations. These modifications can be such as the introduction of protecting groups, cleavage of protecting groups, reduction or oxidation of functional groups, halogenation, metallation, metal-catalysed coupling reactions, substitution or other reactions known to the person skilled in the art. These transformations include those which introduce a functionality which allows for further interconversion of substituents. Appropriate protecting groups and their introduction and cleavage are well-known to the person skilled in the art. Specific examples are described in the subsequent paragraphs.

Scheme 1 shows a route for the preparation of compounds of general formula (I) in which X, Y, Z, $R^1$, $R^2$, $R^3$, $R^4$ and $R^5$ have the meaning as given for the general formula (I) supra.

Dichloropyrimidine carboxylates can be coupled in a Suzuki cross coupling reaction with boronic acids/esters of formula (III) in order to provide non-commercial compounds of formula (IV). This reaction can be performed using appropriate palladium catalysts, such as $Pd(PPh_3)_4$ or Xphos precatalysts, in the presence or absence of phosphine ligands, a base, such as potassium carbonate or sodium carbonate, in a solvent such as THF, DMF, dioxane or toluene, and in the presence or absence of water.

Conversion to the carboxylic acids of formula (V) can be achieved using aqueous bases such as NaOH or LiOH.

Compounds of formula (VII) can be prepared in an analogous fashion as compounds of formula (IV) via a Suzuki cross coupling reaction with boronic acids/esters of formula (VI).

Compounds of general formula (I) can then be synthesised through an amine coupling using an amine of formula (VIII). This reaction can be performed using reagents such as HATU or T3P, in the presence of a base such as $NaHCO_3$, $Na_2CO_3$, $K_2CO_3$ or DIPEA in solvents like dioxane, THF, DMF or NMP. Optionally this amide coupling can also be made via the acyl chloride or the anhydride derivatives of compounds (VII).

Scheme 1: Route for the preparation of compounds of general formula (I) in which X, Y, Z, $R^1$, $R^2$ and $R^4$ have the meaning as given for general formula (I), supra and R represents hydrogen or C1-C4-alkyl.

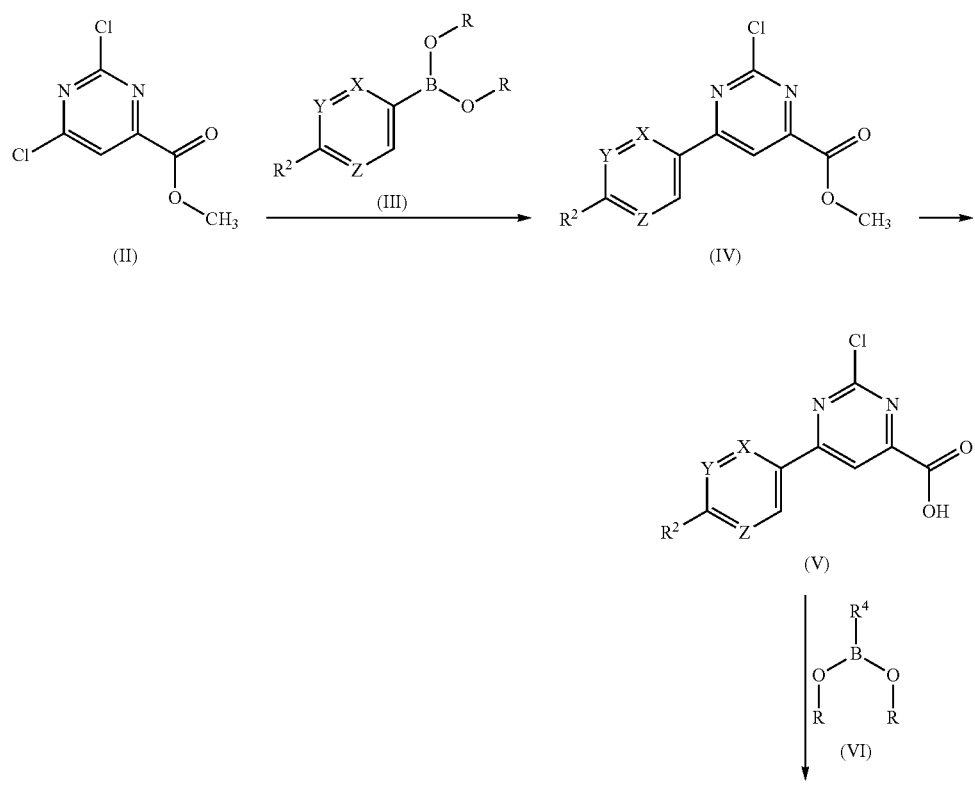

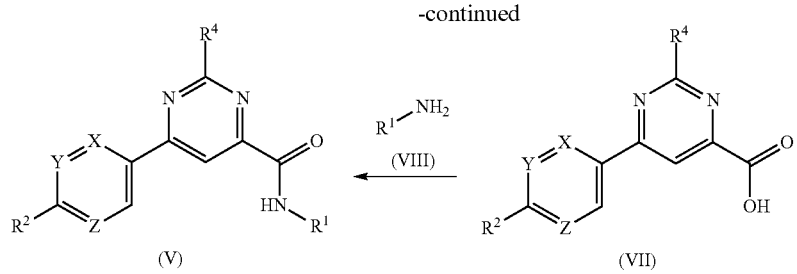

Scheme 2 describes another route for the preparation of compounds or formula (I) using the same steps as in scheme 1 but in a different order.

Scheme 2: Route for the preparation of compounds of general formula (I) in which X, Y, Z, $R^1$, $R^2$ and $R^4$ have the meaning as given for general formula (I), supra and R represents hydrogen or C1-C4-alkyl.

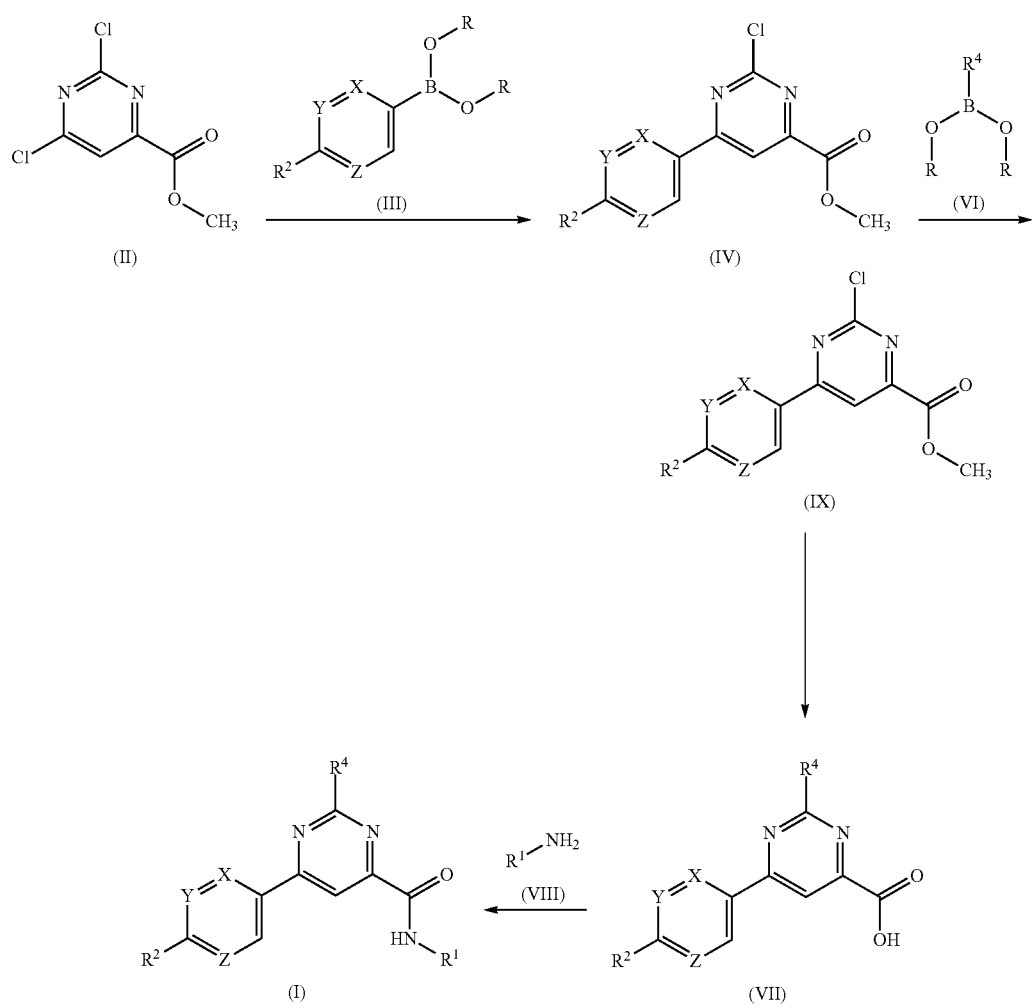

Scheme 3 describes an alternative route to prepare compounds of general formula (I).

2,6-Dichloropyrimidine-4-carboxylic acid can be reacted with an amine of formula (VII) via an amid coupling reaction to provide compounds of formula (XI). This reaction can be performed using reagents such as HATU or T3P, in the presence of a base such as $NaHCO_3$, $Na_2CO_3$, $K_2CO_3$ or DIPEA in solvents like dioxane, THF, DMF or NMP. Two subsequent Suzuki cross coupling reactions using first a boronic acid/ester of formula (III) and then a boronic acid/ester of formula (VI) allow the preparation of compounds of general formula (I). Such reactions can be performed using palladium catalysts such as $Pd(PPh_3)_4$ or Xphos precatalysts, in the presence or absence of phosphine ligands, a base, such as K₂CO₃, Na₂CO₃ or CsCO₃, in a solvent such as THF, DMF, dioxane or toluene, and in the presence or absence of water.

Scheme 3: Route for the preparation of compounds of general formula (I) in which X, Y, Z, R1, R2 and R4 have the meaning as given for general formula (I), supra and R represents hydrogen or C1-C4-alkyl.

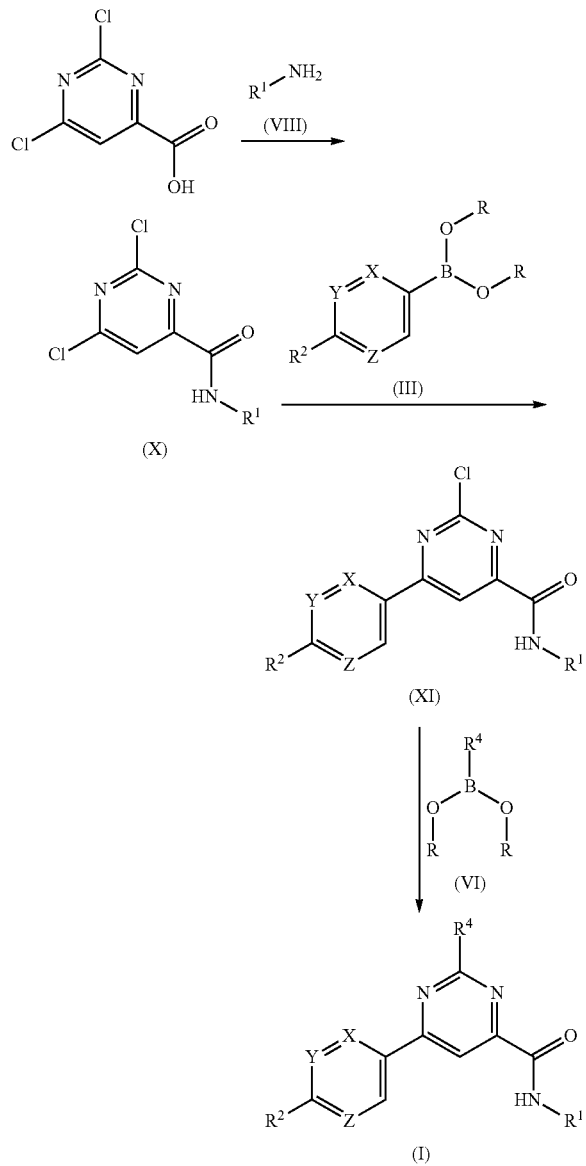

Compounds of general formula (I) of the present invention demonstrate a valuable pharmacological spectrum of action, which could not have been predicted. Compounds of the present invention have surprisingly been found to effectively inhibit AHR and it is possible therefore that said compounds be used for the treatment or prophylaxis of diseases, preferably cancer or conditions with dysregulated immune responses or other disorders associated with aberrant AHR signaling, in humans and animals.

Disorders and conditions particularly suitable for treatment with an AHR inhibitor of the present invention are liquid and solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, triple negative breast cancer, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, glioblastoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Examples of ovarian cancer include, but are not limited to serous tumour, endometrioid tumour, mucinous cystadenocarcinoma, granulosa cell tumour, Sertoli-Leydig cell tumour and arrhenoblastoma.

Examples of cervical cancer include, but are not limited to squamous cell carcinoma, adenocarcinoma, adenosquamous carcinoma, small cell carcinoma, neuroendocrine tumour, glassy cell carcinoma and villoglandular adenocarcinoma.

Tumours of the digestive tract include, but are not limited to, anal, colon, colorectal, esophageal, gallbladder, gastric, pancreatic, rectal, small-intestine, and salivary gland cancers. Examples of esophageal cancer include, but are not limited to esophageal cell carcinomas and adenocarcinomas, as well as squamous cell carcinomas, leiomyosarcoma, malignant melanoma, rhabdomyosarcoma and lymphoma.

Examples of gastric cancer include, but are not limited to intestinal type and diffuse type gastric adenocarcinoma.

Examples of pancreatic cancer include, but are not limited to ductal adenocarcinoma, adenosquamous carcinomas and pancreatic endocrine tumours.

Tumours of the urinary tract include, but are not limited to, bladder, penile, kidney, renal pelvis, ureter, urethral and human papillary renal cancers.

Examples of kidney cancer include, but are not limited to renal cell carcinoma, urothelial cell carcinoma, juxtaglomerular cell tumour (reninoma), angiomyolipoma, renal oncocytoma, Bellini duct carcinoma, clear-cell sarcoma of the kidney, mesoblastic nephroma and Wilms' tumour.

Examples of bladder cancer include, but are not limited to transitional cell carcinoma, squamous cell carcinoma, adenocarcinoma, sarcoma and small cell carcinoma.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, squamous cell cancer of the head and neck, laryngeal, hypopharyngeal, nasopharyngeal, oropharyngeal cancer, salivary gland cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The term "treating" or "treatment" as stated throughout this document is used conventionally, for example the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

yield better efficacy in reducing the growth of a tumour or even eliminate the tumour as compared to administration of either agent alone, provide for the administration of lesser amounts of the administered chemotherapeutic agents, provide for a chemotherapeutic treatment that is well tolerated in the patient with fewer deleterious pharmacological complications than observed with single agent chemotherapies and certain other combined therapies, provide for treating a broader spectrum of different cancer types in mammals, especially humans, provide for a higher response rate among treated patients, provide for a longer survival time among treated patients compared to standard chemotherapy treatments, provide a longer time for tumour progression, and/or yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention may be used to sensitize a cell to radiation, i.e. treatment of a cell with a compound of the present invention prior to radiation treatment of the cell renders the cell more susceptible to DNA damage and cell death than the cell would be in the absence of any treatment with a compound of the present invention. In one aspect, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In one aspect, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e. after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g. cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of general formula (I) of the present invention is administered to a cell prior to the radiation or other induction of DNA damage in the cell. In another aspect of the invention, a compound of general formula (I) of the present invention is administered to a cell concomitantly with the radiation or other induction of DNA damage in the cell. In yet another aspect of the invention, a compound of general formula (I) of the present invention is administered to a cell immediately after radiation or other induction of DNA damage in the cell has begun.

In another aspect, the cell is in vitro. In another embodiment, the cell is in vivo.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with: 131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

The compounds of the invention can further be combined with other reagents targeting the immune system, such as immune checkpoint inhibitors. Compositions comprising a PD-1/-L1 axis antagonist and an AHR antagonist and methods of using the same are provided herein. Data presented herein demonstrate that a combination of AHR inhibition and blockade of the PD-1/-L1 axis reduces the growth of tumor cells in more than an additive manner. PD-1, along with its ligands PD-L1 and PD-L2, function as negative regulators of T cell activation. AHR suppresses immune cell function while increasing cancer cell proliferation and motility. PD-L1 is overexpressed in many cancers and overexpression of PD-1 often occurs concomitantly in tumor infiltrating T cells. Thus results in attenuation of T cell activation and evasion of immune surveillance, which contributes to impaired antitumor immune responses. (Keir M E et al. (2008) Annu. Rev. Immunol. 26:677). Simultaneously targeting both the PD-1/-L1 axis and AHR enhances anti-tumor immune responses in more than an additive manner, leading to reduction of tumor growth that is unexpected. In some experiments, the resulting effect is greater than the expected or calculated additive effect of the individual components given separately. Thus, compositions comprising a PD-1/-L1 axis antagonist and an AHR antagonist are surprisingly effective in enhancing an immune response and in the treatment of cancer.

In addition, the inventive compounds can also be used as a therapeutic in a variety of other disorders wherein AHR is involved such as, cardiovascular and lung diseases.

Accordingly, the compounds according to the invention are suitable for the treatment and/or prophylaxis in particular of cardiovascular, inflammatory and fibrotic disorders and of renal disorders, in particular of acute and chronic renal insufficiency, and also of acute and chronic renal failure.

Accordingly, the compounds according to the invention can be used in medicaments for the treatment and/or prophylaxis of cardiovascular, inflammatory and fibrotic disorders, renal disorders, in particular of acute and chronic renal insufficiency, and also of acute and chronic renal failure.

For the purpose of the present invention the term renal insufficiency comprises both acute and chronic manifestations of renal insufficiency, and also underlying or related renal disorders such as diabetic and non-diabetic nephropathies, hypertensive nephropathies, ischaemic renal disorders, renal hypoperfusion, intradialytic hypotension, obstructive uropathy, renal stenoses, glomerulopathies, glomerulonephritis (such as, for example, primary glomerulonephritides; minimal change glomerulonephritis (lipoid-nephrosis); membranous glomerulonephritis; focal segmental glomerulosclerosis (FSGS); membrane-proliferative glomerulonephritis; crescentic glomerulonephritis; mesangioproliferative glomerulonephritis (IgA nephritis, Berger's disease); post-infectious glomerulonephritis; secondary glomerulonephritides: diabetes mellitus, lupus erythematosus, amyloidosis, Goodpasture syndrome, Wegener granulomatosis, Henoch-Schönlein purpura, microscopic polyangiitis, acute glomerulonephritis, pyelonephritis (for example as a result of: urolithiasis, benign prostate hyperplasia, diabetes, malformations, abuse of analgesics, Crohn's disease), glomerulosclerosis, arteriolonecrose of the kidney, tubulointerstitial diseases, nephropathic disorders such as primary and congenital or aquired renal disorder, Alport syndrome, nephritis, immunological kidney disorders such as kidney transplant rejection and immunocomplex-induced renal disorders, nephropathy induced by toxic substances, nephropathy induced by contrast agents, diabetic and non-diabetic nephropathy, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or the need for dialysis. The present invention also comprises the use of the compounds according to the invention for the treatment and/or prophylaxis of sequelae of renal insufficiency, for example pulmonary oedema, heart failure, uremia, anemia, electrolyte disturbances (for example hypercalemia, hyponatremia) and disturbances in bone and carbohydrate metabolism.

The present invention also comprises the use of the compounds according to the invention for the treatment and/or prevention of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

The compounds according to the invention are further suitable for the treatment and/or prevention of polycystic kidney disease (PCKD) and of the syndrome of inappropriate ADH secretion (SIADH).

Furthermore, the compounds according to the invention are also suitable for the treatment and/or prophylaxis of metabolic syndrome, hypertension, resistant hypertension, acute and chronic heart failure, coronary heart disease, stable and unstable angina pectoris, peripheral and cardiac vascular disorders, arrhythmias, atrial and ventricular arrhythmias and impaired conduction, for example atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation, for example pulmonary oedema, cerebral oedema, renal oedema or oedema caused by heart failure, peripheral circulatory disturbances, reperfusion damage, arterial and venous thromboses, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for treatment and/or prophylaxis of erectile dysfunction and female sexual dysfunction.

In addition, the compounds according to the invention are also suitable for treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraines. They are also suitable for the prophylaxis and control of sequelae of cerebral infarction (cerebral apoplexy) such as stroke, cerebral ischaemia and craniocerebral trauma. The compounds according to the invention can likewise be used for controlling states of pain and tinnitus.

In addition, the compounds according to the invention have anti-inflammatory action and can therefore be used as anti-inflammatory agents for treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

Furthermore, the compounds according to the invention can also be used for treatment and/or prophylaxis of autoimmune diseases.

The compounds according to the invention are also suitable for treatment and/or prophylaxis of fibrotic disorders of the internal organs, for example the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

The compounds according to the invention are also suitable for controlling postoperative scarring, for example as a result of glaucoma operations.

The compounds according to the invention can also be used cosmetically for ageing and keratinized skin.

Moreover, the compounds according to the invention are suitable for treatment and/or prophylaxis of hepatitis, neoplasms, osteoporosis, glaucoma and gastroparesis.

The present invention further provides for the use of the compounds according to the invention for treatment and/or prophylaxis of disorders, especially the disorders mentioned above.

The present invention further provides for the use of the compounds according to the invention for the treatment and/or prophylaxis of chronic renal disorders, acute and chronic renal insufficiency, diabetic, inflammatory or hypertensive nephropaties, fibrotic disorders, cardiac insufficiency, angina pectoris, hypertension, pulmonary hypertension, ischemias, vascular disorders, thromboembolic disorders, arteriosclerosis, sickle cell anemia, erectile dysfunction, benign prostate hyperplasia, dysuria associated with benign prostate hyperplasia, Huntington, dementia, Alzheimer and Creutzfeld-Jakob.

The present invention further provides a method for treatment and/or prophylaxis of disorders, in particular the disorders mentioned above, using an effective amount of at least one of the compounds according to the invention.

The present invention further provides a method for the treatment and/or prophylaxis of chronic renal disorders, acute and chronic renal insufficiency, diabetic, inflammatory or hypertensive nephropathies, fibrotic disorders, cardiac insufficiency, angina pectoris, hypertension, pulmonary hypertension, ischemias, vascular disorders, thromboembolic disorders, arteriosclerosis, sickle cell anemia, erectile dysfunction, benign prostate hyperplasia, dysuria associated with benign prostate hyperplasia, Huntington, dementia, Alzheimer and Creutzfeld-Jakob.

In another embodiment, the inventive compounds can also be used to treat or to prevent uterine fibroids (uterine leiomyoma or uterine myoma) in women.

Uterine fibroids are benign tumors of the myometrium, the smooth muscle layer of the uterus. Uterine fibroids grow slowly during a women's life, and their growth is dependent on the female sexual hormones estradiol and progesterone [Kawaguchi K et al. Immunohistochemical analysis of oestrogen receptors, progesterone receptors and Ki-67 in leiomyoma and myometrium during the menstrual cycle and pregnancy Virchows Arch A Pathol Anat Histopathol. 1991; 419(4):309-15.], therefore the highest prevalence of uterine fibroids with approx. 70% and >80% in white and afro-american women, respectively, is found from 35 years of age onwards to menopause, when they shrink due to reduced hormone levels [Baird D D et al. High cumulative incidence of uterine leiomyoma in black and white women: Ultrasound evidence Am J Obstet Gynecol. 2003 January; 188(1):100-7.]. Approx 30% and 45% of white and afro-american women, respectively, do show clinically relevant symptoms due to their fibroids, which are heavy menstrual bleeding and pain, which is related to the menstrual cycle [David M et al. Myoma-associated pain frequency and intensity: a retrospective evaluation of 1548 myoma patients. Eur J Obstet Gynecol Reprod Biol. 2016 April; 199:137-40]. Heavy menstrual bleeding in this respect is defined by a blood loss of more than 80 mL in a menstrual bleeding period [Fraser I S et al. The FIGO Recommendations on Terminologies and Definitions for Normal and Abnormal Uterine Bleeding, Semin Reprod Med 2011; 29(5): 383-390]. Submucosal position of the uterine fibroids, e.g. those located directly below the endometrium, seems to have an even more severe effect on uterine bleeding, which may result in anemia in affected women [Yang J H et al. Impact of submucous myoma on the severity of anemia. Fertil Steril. 2011 April; 95(5):1769-72]. Furthermore, uterine fibroids, due to their symptoms, do severely affect the quality of life of affected women [Downes E et al. The burden of uterine fibroids in five European countries. Eur J Obstet Gynecol Reprod Biol. 2010 September; 152(1):96-102].

So far, it is not understood how uterine fibroids do cause heavy menstrual bleeding. Disregulated genes in uterine fibroids, in comparison to normal myometrium, can give a hint to understand the underlying mechanisms. In published and internal studies, we found TDO2, Tryptophan 2,3-dioxygenase, being highly upregulated [Tsibris J C et al. Insights from gene arrays on the development and growth regulation of uterine leiomyomata. Fertil Steril. 2002 July; 78(1):114-21.]. TDO2 metabolizes the substrate L-Tryptophan to L-Kynurenine, which can be further metabolized to kynurenic acid. Both, L-Kynurenine and Kynurenic acid are physiological ligands and activators for the arylhydrocarbon receptor AHR [Opitz C A et al. An endogenous tumour-promoting ligand of the human aryl hydrocarbon receptor Nature. 2011 Oct. 5; 478(7368):197-203].

L-Kynurenine controls at least two physiological processes which are dysregulated in uterine fibroids. L-Kynurenine, synthesized by an upregulation of IDO (Indoleamine-2,3-dyoxygenase) or TDO2, and acting via the AHR receptor, suppresses the immune system and thus prevents immune cells from recognizing and clearing the tumor cells [Munn D H Blocking IDO activity to enhance anti-tumor immunity. Front Biosci (Elite Ed). 2012 Jan. 1; 4:734-45]. Furthermore, an upregulation of L-Kynurenine leads to a vasodilation of vessels, and thus can directly increase blood loss and bleeding [Wang Y et al. Kynurenine is an endothelium-derived relaxing factor produced during inflammation Nature Medicine 16, 279-285 (2010)].

In summary, the upregulation of L-Kynurenine through activation of its physiological receptor AHR seems to support uterine fibroid growth by local suppression of the immune system, and might cause heavy menstrual bleeding by vasodilation of endometrial vessels in proximity to the tumor.

Therefore, a systemic or local application of compounds from the present invention inhibiting activation of the AHR and thus blocking the effect of uterine fibroid derived L-Kynurenine presents a new and valid treatment option for uterine fibroids.

Compounds of the present invention can be utilized to inhibit, block, reduce or decrease AHR activation by exogenous and/or endogenous ligands for the reduction of tumour growth and the modulation of dysregulated immune responses e.g. to block immunosuppression and increase immune cell activation and infiltration in the context of cancer and cancer immunotherapy; This method comprises administering to a mammal in need thereof, including a human, an amount of a compound of this invention, or a pharmaceutically acceptable salt, isomer, polymorph, metabolite, hydrate, solvate or ester thereof; which is effective to treat the disorder.

The present invention also provides methods of treating a variety of other disorders wherein AHR is involved such as, but not limited to, inflammation, vaccination for infection & cancer, viral infections, obesity and diet-induced obesity, adiposity, metabolic disorders, hepatic steatosis and uterine fibroids.

These disorders have been well characterized in humans, but also exist with a similar etiology in other mammals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as liquid and solid tumours.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular cancer or conditions with dysregulated immune responses or other disorders associated with aberrant AHR signaling.

The pharmaceutical activity of the compounds according to the invention can be explained by their activity as AHR inhibitors.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular cancer or conditions with dysregulated immune responses or other disorders associated with aberrant AHR signaling, particularly liquid and solid tumours.

In accordance with a further aspect, the present invention covers the use of a compound of formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of diseases, in particular cancer or conditions with dysregulated immune responses or other disorders associated with aberrant AHR signaling, particularly liquid and solid tumours.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular cancer or conditions with dysregulated immune responses or other disorders associated with aberrant AHR signaling, particularly liquid and solid tumours.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular cancer or conditions with dysregulated immune responses or other disorders associated with aberrant AHR signaling, particularly liquid and solid tumours.

In accordance with a further aspect, the present invention covers a method of treatment or prophylaxis of diseases, in particular cancer or conditions with dysregulated immune responses or other disorders associated with aberrant AHR signaling, particularly liquid and solid tumours, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example,) Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride),
adsorbents (for example highly-disperse silicas),
viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragie®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prophylaxis of cancer or conditions with dysregulated immune responses or other disorders associated with aberrant AHR signaling generic name disorders, particularly liquid and solid tumours.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

Based upon standard laboratory techniques known to evaluate compounds useful for the treatment of cancer or conditions with dysregulated immune responses or other disorders associated with aberrant AHR signaling, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

NMR peak forms are stated as they appear in the spectra, possible higher order effects have not been considered. The multiplicities are stated according to the signal form which appears in the spectrum, NMR-spectroscopic effects of a higher order were not taken into consideration. Multiplicity of the NMR signals: s=singlet, d=doublet, t=triplet, q=quartet, qi, quin=quintet, b, br=broad signal, m=multiplet. NMR signals: shift in ppm. Combinations of multiplicity could be e.g. dd=doublet from doublet.

Chemical names were generated using the ACD/Name software from ACD/Labs. In some cases generally accepted names of commercially available reagents were used in place of ACD/Name generated names.

Table 1 lists the abbreviations used in this paragraph and in the Examples section as far as they are not explained within the text body. Other abbreviations have their meanings customary per se to the skilled person.

TABLE 1

| Abbreviations | |
|---|---|
| ACN | acetonitrile |
| AcOH | acetic acid |
| BPR | Back Pressure Regulator |
| CDCl$_3$ | deuterochloroform |
| DAD | diode array detector |
| DCM | dichloromethane |
| DEA | diethylamine |
| DIPEA | N,N-Diisopropylethylamine |

TABLE 1-continued

| Abbreviations | |
|---|---|
| DMA | N,N-dimethylacetamide |
| DME | 1,2-dimethoxyethane |
| DMF | N,N-dimethylformamide |
| DMSO-d6 | deuterated dimethyl sulfoxide |
| DMSO | dimethyl sulfoxide |
| EtOAc | ethyl acetate |
| Eq | equivalent |
| ESI | electrospray ionisation |
| Expl. | example |
| HATU | (7-aza-1H-benzotriazol-1-yl)-1,1,3,3-tetramethyluronium hexafluorophosphate |
| HBTU | O-benzotriazole-N,N,N',N'-tetramethyluronium hexafluorophosphate |
| HPLC | high-pressure liquid chromatography |
| KA | kynurenic acid |
| LCMS | liquid chromatography coupled with mass spectrometry |
| LPS | lipopolysaccharide |
| mL | milliliter |
| min. | minute(s) |
| M | molar |
| MS | mass spectrometry |
| MTBE | methyl tert-butyl ether |
| NMP | N-Methyl-2-pyrrolidone |
| p | pressure |
| PBMC | peripheral blood mononuclear cells |
| PyBOB | (benzotriazol-1-yl)oxytripyrrolidinophosphonium hexafluorophosphate |
| RP-HPLC | reverse-phase high-pressure liquid chromatography |
| Rt | retention time |
| rt, r.t. | room temperature |
| sat. | saturated |
| T3P | 2,4,6-tripropyl-1,3,5,2,4,6-trioxatriphosphorinane 2,4,6-trioxide |
| TEA | triethylamine |
| THF | tetrahydrofuran |
| TFA | trifluoroacetic acid |
| TLC | thin layer chromatography |
| TNFa | tumour necrosis factor alpha |
| μM | micromolar |
| UPLC | Ultra high performance chromatography |
| Xphos | 2-Dicyclohexylphosphino-2',4',6'-triisopropylbiphenyl |

The various aspects of the invention described in this application are illustrated by the following examples which are not meant to limit the invention in any way.

The example testing experiments described herein serve to illustrate the present invention and the invention is not limited to the examples given.

EXPERIMENTAL SECTION—GENERAL PART

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC/MS-Methods

Method 1:

Instrument: Waters Acquity UPLCMS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Method 2:

Instrument: Waters Acquity UPLCMS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method 3:

Instrument: Waters Autopurification MS SingleQuad; Colum: Waters XBrigde C18 5μ 100×30 mm; eluent A: water+0.2 vol % aqueous ammonia (32%), eluent B: acetonitrile; gradient: 0-5.5 min 5-100% B; flow 70 ml/min; temperature: 25° C.; DAD scan: 210-400 nm.

EXPERIMENTAL SECTION—INTERMEDIATES

Intermediate 1

2-chloro-6-[4-(trifluoromethoxy)phenyl]pyrimidine-4-carboxylic acid

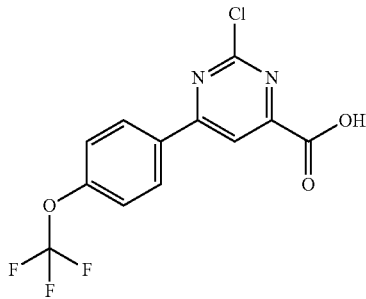 [SMILES: O=C(O)c1cc(-c2ccc(OC(F)(F)F)cc2)nc(Cl)n1]

Methyl 2,6-dichloropyrimidine-4-carboxylate (1.00 g, 4.83 mmol) and [4-(trifluoromethoxy)phenyl]boronic acid (895 mg, 4.35 mmol) were dissolved in 20 mL dioxane, sodium carbonate (7.2 mL, 2.0 M, 14 mmol) and tetrakis(triphenylphosphine)palladium(0) (558 mg, 483 μmol) were added. The mixture was stirred for 2 h at 90° C. The reaction mixture was filtered and the precipitate was washed with DCM to give the title compound as a salt (2.47 g, 4.65 mmol, 60% purity).

LC-MS (Method 1): $R_t$=0.71 min; MS (ESIpos): m/z=319 $[M+H]^+$ $^1$H-NMR (400 MHz, DMSO-d6): δ [ppm]=7.57 (dd, 2H), 8.35-8.44 (m, 2H), 8.54 (s, 1H)

Intermediate 2

2,6-dichloro-N-[(2S)-1-hydroxypropan-2-yl]pyrimidine-4-carboxamide

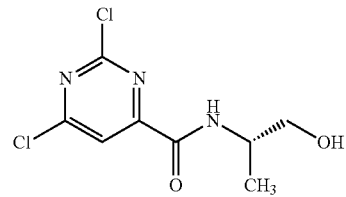

2,6-Dichloropyrimidine-4-carboxylic acid (1.00 g, 5.18 mmol) was solubilised in 8 mL DMF, (2S)-2-aminopropan-1-ol (810 μL, 10 mmol), N,N-diisopropylethylamine (5.4 ml, 31 mmol) and propylphosphonic anhydride solution (9 mL, 50% purity, 16 mmol) were added and it was stirred for 2 h at rt. The reaction was diluted with water and extracted twice with DCM. The organic layer was dried over a silicone filter and concentrated under reduced pressure to obtain the title compound (1.9 g, 2.70 mmol, 75% purity).

LC-MS (Method 1): $R_t$=0.79 min; MS (ESIneg): m/z=248 $[M-H]^-$ $^1$H-NMR (400 MHz, DMSO-d6): δ [ppm]=1.14 (d, 3H), 3.39-3.50 (m, 2H), 3.98-4.07 (m, 1H), 5.76 (s, 1H), 7.90-8.00 (m, 1H), 8.11 (s, 1H)

Intermediate 3

2-chloro-N-[(2S)-1-hydroxypropan-2-yl]-6-[4-(trifluoromethoxy)phenyl]pyrimidine-4-carboxamide

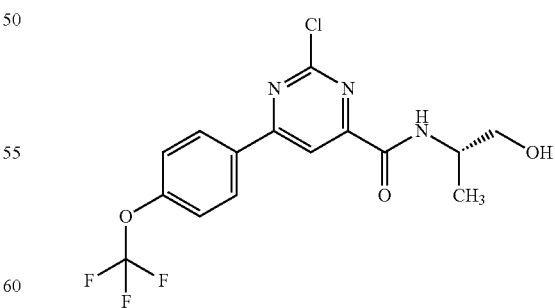

2,6-Dichloro-N-[(2S)-1-hydroxypropan-2-yl]pyrimidine-4-carboxamide (1.93 g, 45% purity, 3.47 mmol) and [4-(trifluoromethoxy)phenyl]boronic acid (643 mg, 3.12 mmol) were dissolved in a mixture of 15 mL dioxane and 2.9 mL water, aqueous potassium carbonate solution (5.2 mL, 2.0

M, 10 mmol) and AmPhosPdCl2 (244 mg, 347 µmol) were added. The mixture was stirred for 2 h at 80° C. The reaction was concentrated under reduced pressure. The residue was purified using a 25 g Ultra Sil-cartridge, 100% Hex-80% EtOAc, to give of the title compound 117 mg (75% purity, 7% yield) and 240 mg (94% purity, 17% yield).

LC-MS (Method 1): $R_t$=1.25 min; MS (ESIneg): m/z=374 [M−H]$^-$ $^1$H-NMR (400 MHz, DMSO-d$_6$): δ [ppm]=1.18 (d, 3H), 3.41-3.56 (m, 2H), 3.99-4.06 (m, 1H), 4.88 (t, 1H), 7.57 (dd, 2H), 8.39-8.45 (m, 2H), 8.52 (s, 1H), 8.59 (d, 1H)

Intermediate 4

2-chloro-N-[(2R)-1-hydroxypropan-2-yl]-6-[4-(trifluoromethoxy)phenyl]pyrimidine-4-carboxamide

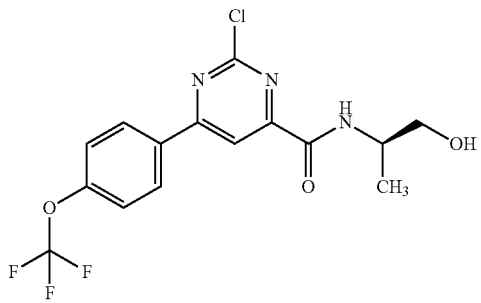 [SMILES: C[C@H](CO)NC(=O)c1cc(-c2ccc(OC(F)(F)F)cc2)nc(Cl)n1]

2-Chloro-6-[4-(trifluoromethoxy)phenyl]pyrimidine-4-carboxylic acid (1.20 g, 88% purity, 3.31 mmol), (2R)-2-aminopropan-1-ol (390 µL, 5.0 mmol), sodium bicarbonate (1.67 g, 19.9 mmol) and HATU (3.78 g, 9.94 mmol) were stirred in 17 mL DMF overnight at rt. The mixture was diluted with EtOAc and washed with half saturated brine thrice. The organic phase was dried over a silicone filter and concentrated under reduced pressure The residue was purified using a 50 g Ultra Sil-cartridge, 100% Hex-100% EtOAc, to give 312 mg (63% purity, 16% yield) of the title compound.

LC-MS (Method 1): $R_t$=1.25 min; MS (ESIpos): m/z=376 [M+H]$^+$

Intermediate 5

2-chloro-N-(2-hydroxy-2-methylpropyl)-6-[4-(trifluoromethoxy)phenyl]pyrimidine-4-carboxamide

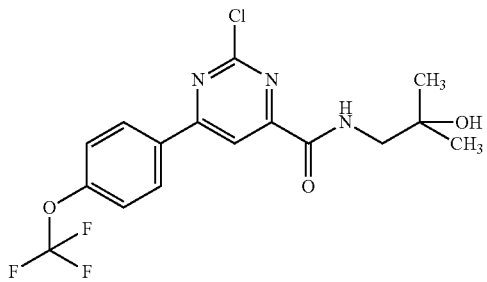 [SMILES: CC(C)(O)CNC(=O)c1cc(-c2ccc(OC(F)(F)F)cc2)nc(Cl)n1]

2-Chloro-6-[4-(trifluoromethoxy)phenyl]pyrimidine-4-carboxylic acid (2.20 g, 60% purity, 4.14 mmol), 1-amino-2-methylpropan-2-ol (554 mg, 6.21 mmol), N,N-diisopropylethylamine (3.6 mL, 21 mmol) and propylphosphonic anhydride solution (7.4 mL, 50% purity, 12 mmol) were stirred in 960 µL NMP for 1 h at rt. The reaction was diluted with water and stirred for 30 min. The aqueous mixture was extracted with DCM. The organic layer was washed with half saturated brine thrice, dried over a silicone filter and concentrated under reduced pressure to give 2.0 g (4.11 mmol, 80% purity) of the title compound.

LC-MS (Method 1): $R_t$=1.31 min; MS (ESIpos): m/z=390 [M+H]$^+$

Intermediate 6

2-chloro-N-[(2S)-3,3,3-trifluoro-2-hydroxypropyl]-6-[4-(trifluoromethoxy)phenyl]pyrimidine-4-carboxamide

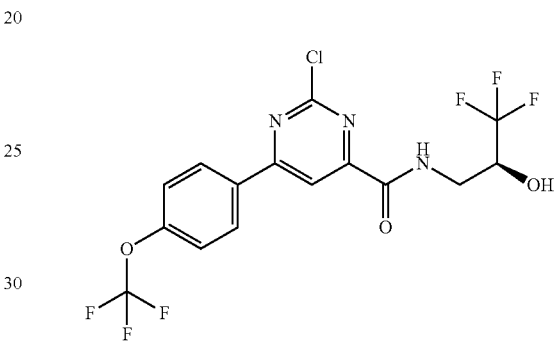

2-Chloro-6-[4-(trifluoromethoxy)phenyl]pyrimidine-4-carboxylic acid (250 mg, 60% purity, 471 µmol), (2R)-3-amino-1,1,1-trifluoropropan-2-ol (72.9 mg, 565 µmol), N,N-diisopropylethylamine (410 µL, 2.4 mmol) and propylphosphonic anhydride solution (840 µL, 50% purity, 1.4 mmol) were stirred in 2.0 mL NMP for 1 h at rt. The reaction was diluted with water and stirred for 30 min. The aqueous mixture was extracted with DCM. The organic layer was washed with half saturated brine thrice, dried over a silicone filter and concentrated under reduced pressure to give 80 mg (0.19 mmol, 77% purity) of the title compound.

LC-MS (Method 1): $R_t$=1.35 min; MS (ESIneg): m/z=428 [M−H]$^-$

Intermediate 7

2-chloro-6-[4-(trifluoromethyl)phenyl]pyrimidine-4-carboxylic acid

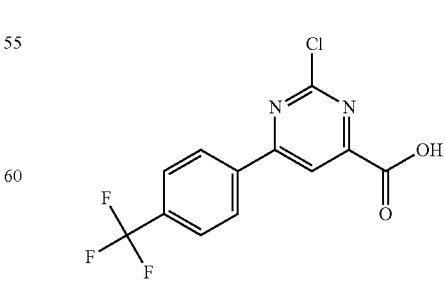

Methyl 2,6-dichloropyrimidine-4-carboxylate (150 mg, 725 µmol) and [4-(trifluoromethyl)phenyl]boronic acid (124 mg, 652 µmol) were dissolved in 3 mL dioxane, aqueous sodium carbonate solution (1.1 mL, 2.0 M, 2.2 mmol) and tetrakis(triphenylphosphine)palladium(0) (83.7 mg, 72.5 µmol) were added. The mixture was stirred for 2 h at 90° C. The reaction mixture was filtered and the precipitate was washed with DCM to give the title compound as a salt (350 mg, 0.69 mmol, 60% purity).

LC-MS (Method 1): $R_t$=0.69 min; MS (ESIneg): m/z=301 [M−H]⁻

Intermediate 8

2-chloro-N-(2-hydroxy-2-methylpropyl)-6-[4-(trifluoromethyl)phenyl]pyrimidine-4-carboxamide

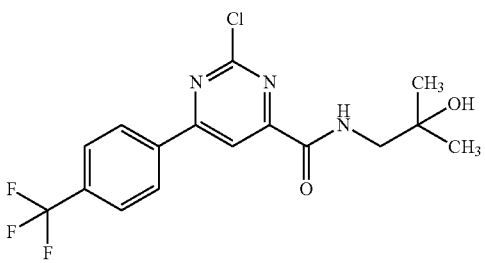 [SMILES: CC(C)(O)CNC(=O)c1cc(-c2ccc(C(F)(F)F)cc2)nc(Cl)n1]

2-Chloro-6-[4-(trifluoromethyl)phenyl]pyrimidine-4-carboxylic acid (1.70 g, 60% purity, 3.37 mmol), 1-amino-2-methylpropan-2-ol (451 mg, 5.06 mmol), N,N-diisopropylethylamine (2.9 mL, 17 mmol) and propylphosphonic anhydride solution (6.0 mL, 50% purity, 10 mmol) were stirred in 960 µL NMP for 1 h at rt. The reaction was diluted with water and stirred for 30 min. The aqueous mixture was extracted with DCM. The organic layer was washed with half saturated brine thrice, dried over a silicone filter and concentrated under reduced pressure to give 740 mg (1.98 mmol, 57% purity) of the title compound.

LC-MS (Method 1): $R_t$=1.26 min; MS (ESIpos): m/z=374 [M+H]⁺

Intermediate 9

2-chloro-6-(4-chlorophenyl)pyrimidine-4-carboxylic acid

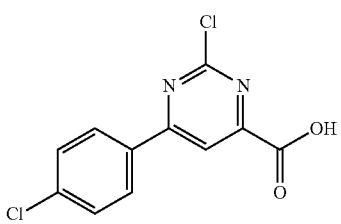 [SMILES: O=C(O)c1cc(-c2ccc(Cl)cc2)nc(Cl)n1]

Methyl 2,6-dichloropyrimidine-4-carboxylate (150 mg, 725 µmol) and (4-chlorophenyl)boronic acid (102 mg, 652 µmol) were dissolved in 3 mL dioxane, aqueous sodium carbonate solution (1.1 mL, 2.0 M, 2.2 mmol) and tetrakis (triphenylphosphine)palladium(0) (83.7 mg, 72.5 µmol) were added. The mixture was stirred for 2 h at 90° C. The reaction mixture was filtered and the precipitate was washed with DCM to give the title compound as a salt (392 mg, 0.73 mmol, 50% purity).

LC-MS (Method 1): $R_t$=0.64 min; MS (ESIpos): m/z=268 [M+H]⁺

¹H-NMR (400 MHz, DMSO-d6): δ [ppm]=7.66 (d, 2H), 8.31 (d, 2H), 8.51 (s, 1H), 13.95-14.75 (m, 1H)

Intermediate 10

2-chloro-6-(4-chlorophenyl)-N-[(2S)-1-hydroxypropan-2-yl]pyrimidine-4-carboxamide

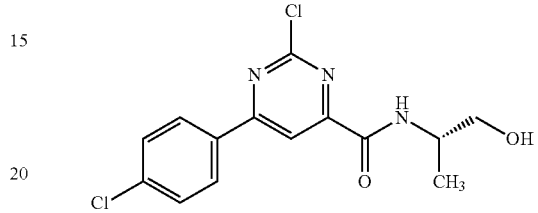

2-Chloro-6-(4-chlorophenyl)pyrimidine-4-carboxylic acid (500 mg, 1.86 mmol), (2S)-2-aminopropan-1-ol (220 µL, 2.8 mmol), sodium bicarbonate (937 mg, 11.1 mmol) and HATU (2.12 g, 5.57 mmol) were stirred in 9.7 mL DMF overnight at rt. The mixture was concentrated under reduced pressure. The residue was purified using a 50 g Ultra Sil-cartridge, 100% Hex-100% EtOAc, to give 197 mg (76% purity, 25% yield) of the title compound.

LC-MS (Method 1): $R_t$=1.19 min; MS (ESIpos): m/z=326 [M+H]⁺

¹H-NMR (400 MHz, DMSO-d6): δ [ppm]=1.17 (d, 3H), 3.40-3.55 (m, 3H), 4.01-4.12 (m, 1H), 4.89 (s, 1H), 7.66 (d, 3H), 8.28-8.33 (m, 3H), 8.51 (s, 1H), 8.58 (d, 1H)

Intermediate 11

2-chloro-6-(4-chlorophenyl)-N-[(2R)-1-hydroxypropan-2-yl]pyrimidine-4-carboxamide

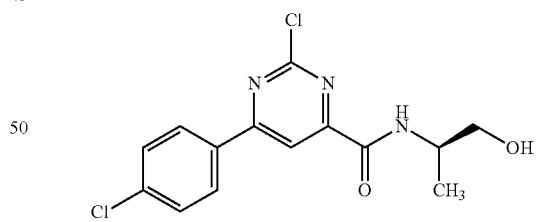

2-Chloro-6-(4-chlorophenyl)pyrimidine-4-carboxylic acid (1.40 g, 55% purity, 2.86 mmol), (2R)-2-aminopropan-1-ol (330 µL, 4.3 mmol), sodium bicarbonate (1.44 g, 17.2 mmol) and HATU (3.26 g, 8.58 mmol) were stirred in 15 mL DMF overnight at rt. The mixture was diluted with EtOAc and washed with half saturated brine thrice. The organic phase was dried over a silicone filter and concentrated under reduced pressure. The residue was purified using a 50 g Ultra Sil-cartridge, 100% Hex-100% EtOAc, to give 321 mg (50% purity, 17% yield) of the title compound.

LC-MS (Method 1): $R_t$=1.18 min; MS (ESIpos): m/z=326 [M+H]⁺

Intermediate 12

2-chloro-6-(4-chlorophenyl)-N-(2-hydroxy-2-methylpropyl)pyrimidine-4-carboxamide

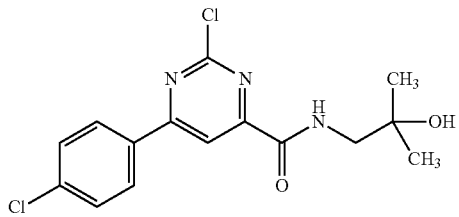 [SMILES: CC(C)(O)CNC(=O)c1cc(-c2ccc(Cl)cc2)nc(Cl)n1]

2-Chloro-6-(4-chlorophenyl)pyrimidine-4-carboxylic acid (2.0 g, 55% purity, 4.09 mmol), 1-amino-2-methylpropan-2-ol (0.55 mL, 6.13 mmol), N,N-diisopropylethylamine (3.56 mL, 20.44 mmol) and propylphosphonic anhydride solution (7.3 mL, 50% purity, 12.3 mmol) were stirred in 10 mL NMP for 1 h at rt. Because of incomplete conversion stirring was continued overnight at rt. Again 1-amino-2-methylpropan-2-ol (0.55 mL, 6.13 mmol), N,N-diisopropylethylamine (3.56 mL, 20.44 mmol) and propylphosphonic anhydride solution (7.3 mL, 50% purity, 12.3 mmol) were added and the mixture was stirred for 1 h at rt. The reaction was diluted with water and stirred for 30 min. The aqueous mixture was extracted with DCM. The organic layer was washed with half saturated brine thrice, dried over a silicone filter and concentrated under reduced pressure to give 2.3 g (4.06 mmol, 60% purity) of the title compound.

LC-MS (Method 1): $R_t$=1.24 min; MS (ESIpos): m/z=340 [M+H]$^+$ $^1$H-NMR (400 MHz, DMSO-d$_6$): δ [ppm]=1.13 (s, 6H), 3.31 (s, 2H), 4.75 (br s, 1H), 7.65-7.67 (m, 2H), 8.32 (d, 2H), 8.53 (s, 1H)

Intermediate 13

2-(1-methyl-1H-pyrazol-4-yl)-6-[4-(trifluoromethoxy)phenyl]pyrimidine-4-carboxylic acid

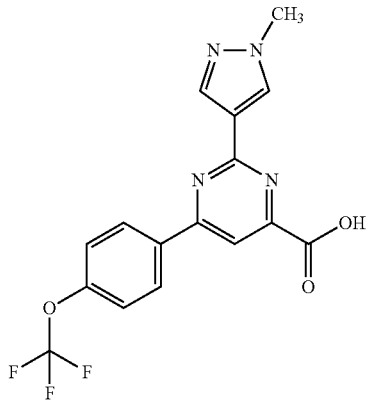 [SMILES: Cn1cc(-c2nc(C(=O)O)cc(-c3ccc(OC(F)(F)F)cc3)n2)cn1]

2-chloro-6-[4-(trifluoromethoxy)phenyl]pyrimidine-4-carboxylic acid (6.76 g, 21.2 mmol) and (1-methyl-1H-pyrazol-4-yl)boronic acid (4.01 g, 31.8 mmol) were solubilised in dioxane and aqueous sodium carbonate (32 ml, 2.0 M, 64 mmol) was added. The reaction mixture was sparged with argon and palladiumtetrakis (2.45 g, 2.12 mmol) was added. The mixture was stirred for 3 h at 80° C. The mixture cooled to rt was diluted with water and acidified with 3N HCl (pH 1). The solid was filtered, washed with H2O and dried overnight at 60° C. to give 7.79 g of the itle compound that was used without further purification.

Intermediate 14

2-(pyridin-3-yl)-6-[4-(trifluoromethyl)phenyl]pyrimidine-4-carboxylic acid

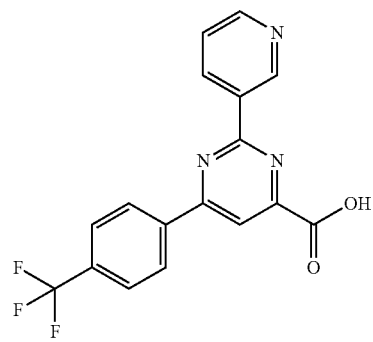 [SMILES: O=C(O)c1cc(-c2ccc(C(F)(F)F)cc2)nc(-c2cccnc2)n1]

2-chloro-6-[4-(trifluoromethyl)phenyl]pyrimidine-4-carboxylic acid (100 mg, 330 μmol) and pyridin-3-ylboronic acid (60.9 mg, 496 μmol) were solubilised in 1,4-dioxane (1.0 ml), aqueous Na2CO3 (500 μl, 2.0 M, 990 μmol) and palladiumtetrakis (38.2 mg, 33.0 μmol) were added. The mixture was stirred for 2 h at 90° C. and the cooled to rt and diluted with water. The aqueous mixture was acidified to pH 1 and extracted twice with DCM. The aqueous layer was filtered and the filtrate was lyophilisated to give 210 mg of the title compound that was used without further purification.

Intermediate 15

2-(pyridin-3-yl)-6-[4-(trifluoromethoxy)phenyl]pyrimidine-4-carboxylic acid

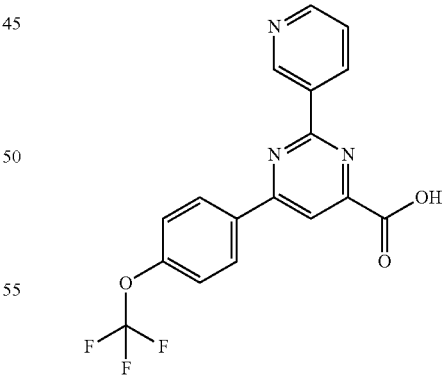

2-chloro-6-[4-(trifluoromethoxy)phenyl]pyrimidine-4-carboxylic acid (150 mg, 471 μmol) and pyridin-3-ylboronic acid (86.8 mg, 706 μmol) were solubilised in 1,4-dioxane (7.5 ml), aqueous Na2CO3 (710 μl, 2.0 M, 1.4 mmol) and palladiumtetrakis (54.4 mg, 47.1 μmol) were added and the mixture was stirred for 2 h at 90° C. The reaction was cooled to rt and diluted with water. The aqueous mixture was acidified to pH 1 and extracted twice with DCM. The aqueous layer was filtered and the filtrate was lyophilisated to give 220 mg of the title compound that was used without further purification.

Intermediate 16

2-chloro-6-[4-(difluoromethyl)phenyl]pyrimidine-4-carboxylic acid

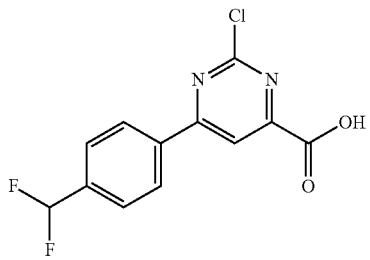 [SMILES: O=C(O)c1cc(-c2ccc(C(F)F)cc2)nc(Cl)n1]

methyl 2,6-dichloropyrimidine-4-carboxylate (1.00 g, 4.83 mmol), [4-(difluoromethyl)phenyl]boronic acid (748 mg, 4.35 mmol) and Bis(di-tert-butyl(4-dimethylaminophenyl)phosphine)dichloropalladium(II) (341 mg, 483 µmol) were dissolved in 1,4-dioxane (20 ml)/water (4.0 ml) and K2CO3 (7.2 ml, 2.0 M, 14 mmol) was added. The mixture was stirred for 2 h at 80° C. The reaction was cooled to rt, diluted with water and acidified to pH 3 using 3N HCl. The aqueous phase was extracted with EtOAc and the organic layer was dried over a silicone filter and concentrated under reduced pressure to give 1.3 g of the title compound that was used without further purification.

Intermediate 17

6-[4-(difluoromethyl)phenyl]-2-(pyridin-3-yl)pyrimidine-4-carboxylic acid

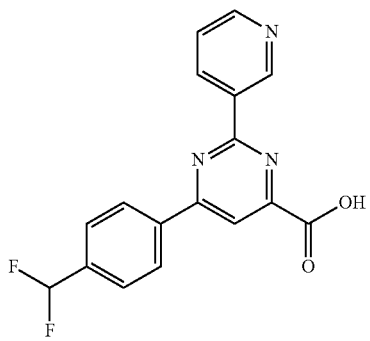 [SMILES: O=C(O)c1cc(-c2ccc(C(F)F)cc2)nc(-c2cccnc2)n1]

2-chloro-6-[4-(difluoromethyl)phenyl]pyrimidine-4-carboxylic acid (400 mg, 1.41 mmol) and pyridin-3-ylboronic acid (259 mg, 2.11 mmol) were solubilised in 1,4-dioxane (4.3 ml), aqueous Na2CO3 (2.1 ml, 2.0 M, 4.2 mmol) and palladiumtetrakis (162 mg, 141 µmol) were added. The mixture was stirred for 2 h at 90° C. and then cooled to rt. The reaction was diluted with water and to pH 1. The aqueous layer was filtered and the solid was dried under reduced pressure to give 287 mg of the crude title compound that was used without further purification.

EXPERIMENTAL SECTION—EXAMPLES

The following examples describe the embodiment of the instant invention, not restricting the invention to these examples only.

Example 1

N-[(2S)-1-hydroxypropan-2-yl]-2-(pyridin-3-yl)-6-[4-(trifluoromethoxy)phenyl]pyrimidine-4-carboxamide

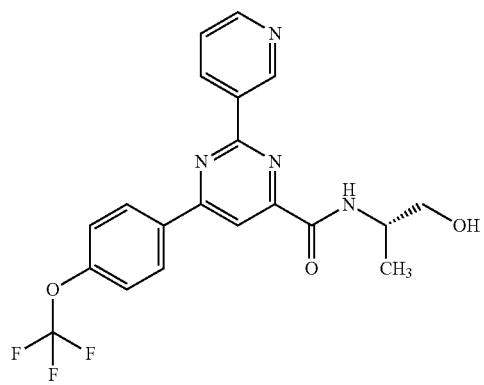 [SMILES: C[C@@H](CO)NC(=O)c1cc(-c2ccc(OC(F)(F)F)cc2)nc(-c2cccnc2)n1]

2-Chloro-N-[(2S)-1-hydroxypropan-2-yl]-6-[4-(trifluoromethoxy)phenyl]pyrimidine-4-carboxamide (473 mg, 1.26 mmol) and pyridin-3-ylboronic acid (774 mg, 6.29 mmol) were dissolved in a mixture of 9.5 mL dioxane and 1.9 mL water, aqueous potassium carbonate solution (1.9 mL, 2.0 M, 3.8 mmol) and Xphos precat G1 (104 mg, 126 µmol) were added. The mixture was stirred for 2 h at 80° C. The reaction was concentrated under reduced pressure. The residue was purified using a 10 g SNAP Sil-cartridge (solvents: Hx/EtOAc: 0-80% EtOAc). Further it was purified by preparative HPLC to give 136 mg (95% purity, 35% yield) of the title compound.

LC-MS (Method 1): $R_t$=1.22 min; MS (ESIpos): m/z=419 [M+H]$^+$ $^1$H-NMR (400 MHz, DMSO-d6): δ [ppm]=1.24 (d, 3H), 3.45-3.62 (m, 2H), 4.08-4.20 (m, 1H), 4.91 (t, 1H), 7.59 (dd, 2H), 7.65 (ddd, 1H), 8.50 (s, 1H), 8.56-8.62 (m, 2H), 8.80 (dd, 1H), 8.83-8.89 (m, 1H), 9.02 (dt, 1H), 9.90 (dd, 1H)

Example 2

N-[(2R)-1-hydroxypropan-2-yl]-2-(pyridin-3-yl)-6-[4-(trifluoromethoxy)phenyl]pyrimidine-4-carboxamide

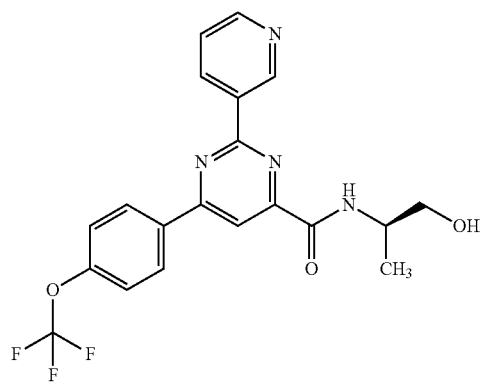 [SMILES: C[C@H](CO)NC(=O)c1cc(-c2ccc(OC(F)(F)F)cc2)nc(-c2cccnc2)n1]

2-Chloro-N-[(2R)-1-hydroxypropan-2-yl]-6-[4-(trifluoromethoxy)phenyl]pyrimidine-4-carboxamide (150 mg, 399 μmol) and pyridin-3-ylboronic acid (73.6 mg, 599 μmol) were dissolved in 6.4 mL dioxane, aqueous sodium carbonate solution (600 μL, 2.0 M, 1.2 mmol) and tetrakis(triphenylphosphine)palladium(0) (46.1 mg, 39.9 μmol) were added. The mixture was stirred for 4 h at 90° C. The mixture was concentrated under reduced pressure. The residue was purified by preparative HPLC to give 40.4 mg (100% purity, 24% yield) of the title compound.

LC-MS (Method 1): $R_t$=1.22 min; MS (ESIpos): m/z=419 [M+H]$^+$ $^1$H-NMR (400 MHz, DMSO-d6): δ [ppm]=1.24 (d, 3H), 3.46-3.62 (m, 2H), 4.08-4.22 (m, 1H), 4.91 (s, 1H), 7.56-7.62 (m, 2H), 7.62-7.68 (m, 1H), 8.50 (s, 1H), 8.59 (d, 2H), 8.78-8.82 (m, 1H), 8.84-8.89 (m, 1H), 8.98-9.05 (m, 1H), 9.90 (d, 1H)

Example 3

N-(2-hydroxy-2-methylpropyl)-2-(pyridin-3-yl)-6-[4-(trifluoromethoxy)phenyl]pyrimidine-4-carboxamide

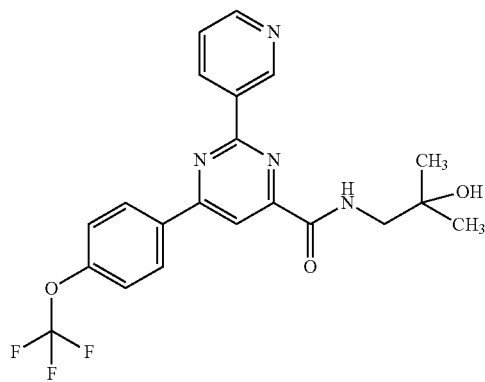 [SMILES: CC(C)(O)CNC(=O)c1cc(-c2ccc(OC(F)(F)F)cc2)nc(-c2cccnc2)n1]

2-Chloro-N-(2-hydroxy-2-methylpropyl)-6-[4-(trifluoromethoxy)phenyl]pyrimidine-4-carboxamide (650 mg, 80% purity, 1.33 mmol) and pyridin-3-ylboronic acid (246 mg, 2.00 mmol) were dissolved in 5 mL dioxane, aqueous sodium carbonate solution (2.0 mL, 2.0 M, 4.0 mmol) and tetrakis(triphenylphosphine)palladium(0) (154 mg, 133 μmol) were added. The mixture was stirred for 2 h at 90° C. UPLC. The reaction was diluted with water and the aqueous mixture was extracted twice with DCM. The organic layer was dried over a silicone filter and concentrated under reduced pressure. The residue was purified by preparative HPLC to give 6 mg (90% purity, 1% yield) of the title compound.

LC-MS (Method 1): $R_t$=1.27 min; MS (ESIneg): m/z=431 [M−H]$^-$ $^1$H-NMR (400 MHz, DMSO-d6): δ [ppm]=1.17 (s, 6H), 4.79 (s, 1H), 7.57-7.62 (m, 2H), 7.66 (ddd, 1H), 8.51 (s, 1H), 8.57-8.62 (m, 2H), 8.80 (dd, 1H), 8.98 (dt, 1H), 9.02 (t, 1H), 9.85 (dd, 1H)

Example 4

2-(pyridin-3-yl)-N-[(2S)-3,3,3-trifluoro-2-hydroxypropyl]-6-[4-(trifluoromethoxy)phenyl]pyrimidine-4-carboxamide

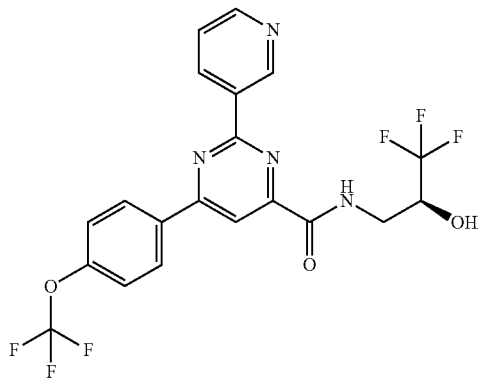 [SMILES: O=C(NC[C@H](O)C(F)(F)F)c1cc(-c2ccc(OC(F)(F)F)cc2)nc(-c2cccnc2)n1]

2-Chloro-N-[(2S)-3,3,3-trifluoro-2-hydroxypropyl]-6-[4-(trifluoromethoxy)phenyl]pyrimidine-4-carboxamide (80.0 mg, 186 μmol) and pyridin-3-ylboronic acid (34.3 mg, 279 μmol) were dissolved in 1 mL dioxane, aqueous sodium carbonate solution (280 μL, 2.0 M, 560 μmol) and tetrakis(triphenylphosphine)palladium(0) (21.5 mg, 18.6 μmol) were added. The mixture was stirred for 2 h at 90° C. The reaction was diluted with water and the aqueous mixture was extracted twice with DCM. The organic layer was dried over a silicone filter and concentrated under reduced pressure. The residue was purified by preparative HPLC to give 39.0 mg (95% purity, 42% yield) of the title compound.

LC-MS (Method 1): $R_t$=1.30 min; MS (ESIpos): m/z=473 [M+H]$^+$ $^1$H-NMR (400 MHz, DMSO-d6): δ [ppm]=3.50-3.62 (m, 1H), 3.64-3.73 (m, 1H), 4.29-4.40 (m, 1H), 7.60 (d, 2H), 7.65 (ddd, 1H), 8.51 (s, 1H), 8.57-8.63 (m, 2H), 8.81 (dd, 1H), 9.05 (dt, 1H), 9.49 (br s, 1H), 9.93 (dd, 1H)

Example 5

N-[(2S)-1-hydroxypropan-2-yl]-2-(1-methyl-1H-pyrazol-4-yl)-6-[4-(trifluoromethoxy)phenyl]pyrimidine-4-carboxamide

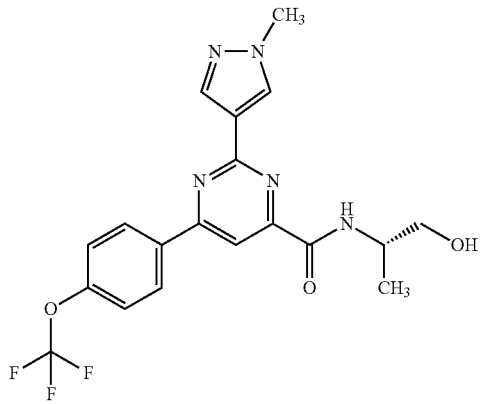 [SMILES: C[C@@H](CO)NC(=O)c1cc(-c2ccc(OC(F)(F)F)cc2)nc(-c2cnn(C)c2)n1]

2-Chloro-N-[(2S)-1-hydroxypropan-2-yl]-6-[4-(trifluoromethoxy)phenyl]pyrimidine-4-carboxamide (357 mg, 950 µmol) and (1-methyl-1H-pyrazol-4-yl)boronic acid (179 mg, 1.43 mmol) were dissolved in a mixture of 7.1 mL dioxane and 1.4 mL water, aqueous potassium carbonate solution (1.4 mL, 2.0 M, 2.9 mmol) and Xphos precat G1 (78.6 mg, 95.0 µmol) were added. The mixture was stirred for 2 h at 80° C. The reaction was concentrated under reduced pressure. The reaction was concentrated under reduced pressure. The residue was purified using a 10 g Ultra Sil-cartridge (solvents: Hx/EtOAc: 0-100% EtOAc). Further it was purified by preparative HPLC to give 196 mg (100% purity, 49% yield) of the title compound.

LC-MS (Method 1): $R_t$=1.17 min; MS (ESIpos): m/z=422 [M+H]$^+$ $^1$H-NMR (400 MHz, DMSO-d6): δ [ppm]=1.23 (d, 3H), 3.44-3.59 (m, 2H), 3.96 (s, 3H), 4.04-4.17 (m, 1H), 4.92 (s, 1H), 7.56 (dd, 2H), 8.24 (s, 1H), 8.37 (s, 1H), 8.46-8.52 (m, 2H), 8.62 (d, 1H), 8.66 (s, 1H)

Example 6

N-(2-hydroxy-2-methylpropyl)-2-(1-methyl-1H-pyrazol-4-yl)-6-[4-(trifluoromethoxy)phenyl]pyrimidine-4-carboxamide

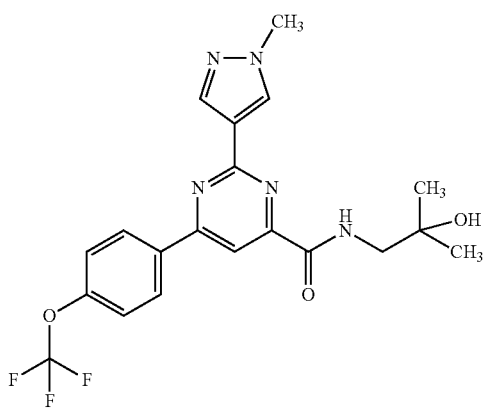 [SMILES: Cn1cc(-c2nc(C(=O)NCC(C)(C)O)cc(-c3ccc(OC(F)(F)F)cc3)n2)cn1]

2-Chloro-N-(2-hydroxy-2-methylpropyl)-6-[4-(trifluoromethoxy)phenyl]pyrimidine-4-carboxamide (650 mg, 80% purity, 1.33 mmol) and (1-methyl-1H-pyrazol-4-yl)boronic acid (252 mg, 2.00 mmol) were dissolved in 5 mL dioxane, aqueous sodium carbonate solution (2.0 mL, 2.0 M, 4.0 mmol) and tetrakis(triphenylphosphine)palladium(0) (154 mg, 133 µmol) were added. The mixture was stirred for 2 h at 90° C. The reaction was diluted with water and the aqueous mixture was extracted twice with DCM. The organic layer was dried over a silicone filter and concentrated under reduced pressure. The residue was purified by preparative HPLC to give 94.0 mg (95% purity, 15% yield) of the title compound.

LC-MS (Method 1): $R_t$=1.27 min; MS (ESIpos): m/z=436 [M+H]$^+$ $^1$H-NMR (400 MHz, DMSO-d6): δ [ppm]=1.15 (s, 6H), 3.36 (d, 2H), 3.93-4.00 (m, 3H), 4.75 (s, 1H), 7.56 (dd, 2H), 8.26 (s, 1H), 8.30 (s, 1H), 8.45-8.52 (m, 2H), 8.62 (s, 1H), 8.79 (t, 1H)

Example 7

N-(2-hydroxy-2-methylpropyl)-2-(pyridin-3-yl)-6-[4-(trifluoromethyl)phenyl]pyrimidine-4-carboxamide

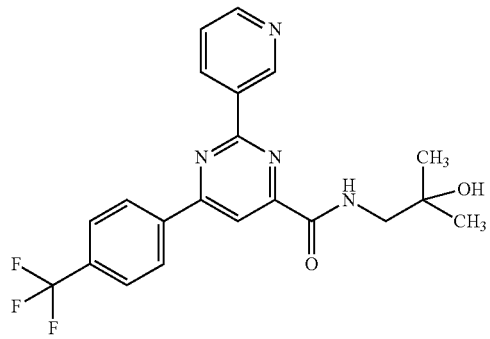 [SMILES: CC(C)(O)CNC(=O)c1cc(-c2ccc(C(F)(F)F)cc2)nc(-c2cccnc2)n1]

2-Chloro-N-(2-hydroxy-2-methylpropyl)-6-[4-(trifluoromethyl)phenyl]pyrimidine-4-carboxamide (240 mg, 642 µmol) and pyridin-3-ylboronic acid (118 mg, 963 µmol) were dissolved in 2 mL dioxane, aqueous sodium carbonate solution (960 µL, 2.0 M, 1.9 mmol) and tetrakis(triphenylphosphine)palladium(0) (74.2 mg, 64.2 µmol) were added. The mixture was stirred for 2 h at 90° C. The reaction was diluted with water and the aqueous mixture was extracted twice with DCM. The organic layer was dried over a silicone filter and concentrated under reduced pressure. The residue was purified by preparative HPLC to give 51.0 mg (95% purity, 18% yield) of the title compound.

LC-MS (Method 1): $R_t$=1.22 min; MS (ESIpos): m/z=417 [M+H]$^+$ $^1$H-NMR (400 MHz, DMSO-d6): δ [ppm]=1.17 (s, 6H), 3.40 (d, 2H), 4.77 (s, 1H), 7.66 (ddd, 1H), 7.97 (d, 2H), 8.57 (s, 1H), 8.66 (d, 2H), 8.81 (dd, 1H), 8.99 (dt, 1H), 9.04 (t, 1H), 9.86 (dd, 1H)

Example 8

N-(2-hydroxy-2-methylpropyl)-2-(1-methyl-1H-pyrazol-4-yl)-6-[4-(trifluoromethyl)phenyl]pyrimidine-4-carboxamide

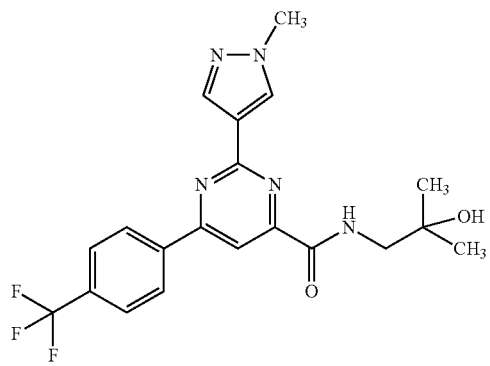 [SMILES: Cn1cc(-c2nc(C(=O)NCC(C)(C)O)cc(-c3ccc(C(F)(F)F)cc3)n2)cn1]

2-Chloro-N-(2-hydroxy-2-methylpropyl)-6-[4-(trifluoromethyl)phenyl]pyrimidine-4-carboxamide (240 mg, 642 µmol) and (1-methyl-1H-pyrazol-4-yl)boronic acid (121 mg, 963 µmol) were dissolved in 2 mL dioxane, aqueous sodium carbonate solution (960 μL, 2.0 M, 1.9 mmol) and tetrakis(triphenylphosphine)palladium(0) (74.2 mg, 64.2 μmol) were added. The mixture was stirred for 2 h at 90° C. The reaction was diluted with water and the aqueous mixture was extracted twice with DCM. The organic layer was dried over a silicone filter and concentrated under reduced pressure. The residue was purified by preparative HPLC to give 57.0 mg (95% purity, 20% yield) of the title compound.

LC-MS (Method 1): R$_t$=1.18 min; MS (ESIpos): m/z=420 [M+H]$^+$ $^1$H-NMR (400 MHz, DMSO-d6): δ [ppm]=1.16 (s, 6H), 3.37 (d, 2H), 3.97 (s, 3H), 4.75 (s, 1H), 7.94 (d, 2H), 8.32 (d, 2H), 8.57 (d, 2H), 8.64 (s, 1H), 8.81 (t, 1H)

Example 9

6-(4-chlorophenyl)-N-[(2S)-1-hydroxypropan-2-yl]-2-(pyridin-3-yl)pyrimidine-4-carboxamide

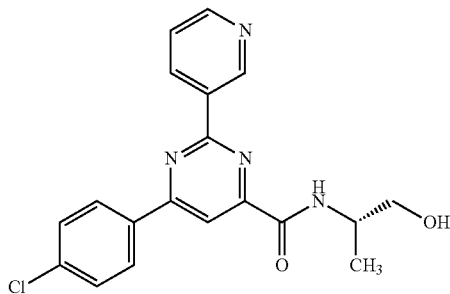 [SMILES: C[C@@H](CO)NC(=O)c1cc(-c2ccc(Cl)cc2)nc(-c2cccnc2)n1]

2-Chloro-6-(4-chlorophenyl)-N-[(2S)-1-hydroxypropan-2-yl]pyrimidine-4-carboxamide (250 mg, 766 μmol) and pyridin-3-ylboronic acid (141 mg, 1.15 mmol) were dissolved in 2.5 mL dioxane, aqueous sodium carbonate solution (1.1 mL, 2.0 M, 2.3 mmol) and tetrakis(triphenylphosphine)palladium(0) (88.6 mg, 76.6 μmol) were added. The mixture was stirred for 2 h at 90° C. The reaction was diluted with water and the aqueous mixture was extracted twice with DCM. The organic layer was dried over a silicone filter and concentrated under reduced pressure. The residue was purified by preparative HPLC to give 14.0 mg (95% purity, 5% yield) of the title compound.

LC-MS (Method 1): R$_t$=1.15 min; MS (ESIpos): m/z=368 [M+H]$^+$ $^1$H-NMR (400 MHz, DMSO-d6): δ [ppm]=1.24 (d, 3H), 3.46-3.61 (m, 2H), 4.10-4.19 (m, 1H), 4.91 (t, 1H), 7.62-7.66 (m, 1H), 7.66-7.70 (m, 2H), 8.47-8.51 (m, 3H), 8.80 (dd, 1H), 8.85 (d, 1H), 9.01 (dt, 1H), 9.90 (dd, 1H)

Example 10

6-(4-chlorophenyl)-N-(2-hydroxy-2-methylpropyl)-2-(pyridin-3-yl)pyrimidine-4-carboxamide

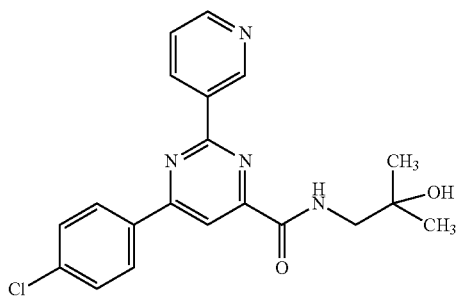 [SMILES: CC(C)(O)CNC(=O)c1cc(-c2ccc(Cl)cc2)nc(-c2cccnc2)n1]

2-Chloro-6-(4-chlorophenyl)-N-(2-hydroxy-2-methylpropyl)pyrimidine-4-carboxamide (750 mg, 60% purity, 1.32 mmol) and pyridin-3-ylboronic acid (244 mg, 1.98 mmol) were dissolved in 4.1 mL dioxane, aqueous sodium carbonate solution (2.0 mL, 2.0 M, 4.0 mmol) and tetrakis(triphenylphosphine)palladium(0) (153 mg, 132 μmol) were added. The mixture was stirred for 2 h at 90° C. The reaction was diluted with water and the aqueous mixture was extracted twice with DCM. The organic layer was dried over a silicone filter and concentrated under reduced pressure. The residue was purified by preparative HPLC to give 44.0 mg (95% purity, 8% yield) of the title compound.

LC-MS (Method 1): R$_t$=1.17 min; MS (ESIpos): m/z=383 [M+H]$^+$ $^1$H-NMR (400 MHz, DMSO-d6): δ [ppm]=1.16 (s, 6H), 3.39 (d, 2H), 4.76 (s, 1H), 7.62-7.72 (m, 3H), 8.47-8.53 (m, 3H), 8.80 (dd, 1H), 8.93-9.06 (m, 2H), 9.85 (d, 1H)

Example 11

6-(4-chlorophenyl)-N-[(2S)-1-hydroxypropan-2-yl]-2-(1-methyl-1H-pyrazol-4-yl)pyrimidine-4-carboxamide

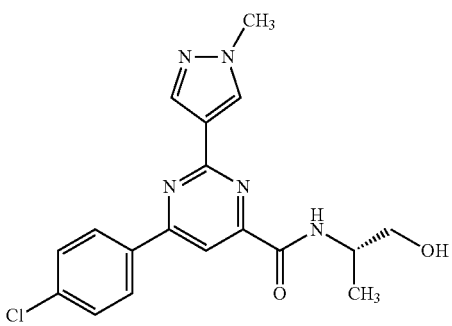 [SMILES: C[C@@H](CO)NC(=O)c1cc(-c2ccc(Cl)cc2)nc(-c2cnn(C)c2)n1]

2-Chloro-6-(4-chlorophenyl)-N-[(2S)-1-hydroxypropan-2-yl]pyrimidine-4-carboxamide (98.0 mg, 300 μmol) and (1-methyl-1H-pyrazol-4-yl)boronic acid (56.7 mg, 451 μmol) were dissolved in 4.8 mL dioxane, aqueous sodium carbonate solution (450 μL, 2.0 M, 900 μmol) and tetrakis(triphenylphosphine)palladium(0) (34.7 mg, 30.0 μmol) were added. The mixture was stirred for 4 h at 90° C. The mixture was concentrated under reduced pressure. The residue was suspended in DMSO/DMF, filtered and the filtrate was purified by preparative HPLC to give 52.7 mg (100% purity, 47% yield) of the title compound.

LC-MS (Method 1): R$_t$=1.11 min; MS (ESIneg): m/z=370 [M−H]$^−$ $^1$H-NMR (400 MHz, DMSO-d6): δ [ppm]=1.24 (d, 3H), 3.54 (br d, 2H), 4.08-4.21 (m, 1H), 4.93 (t, 1H), 7.66 (d, 3H), 8.42-8.50 (m, 3H), 8.77-8.82 (m, 1H), 8.82-8.89 (m, 1H), 9.00 (d, 1H), 9.88 (d, 1H)

Example 12

6-(4-chlorophenyl)-N-[(2R)-1-hydroxypropan-2-yl]-2-(1-methyl-1H-pyrazol-4-yl)pyrimidine-4-carboxamide

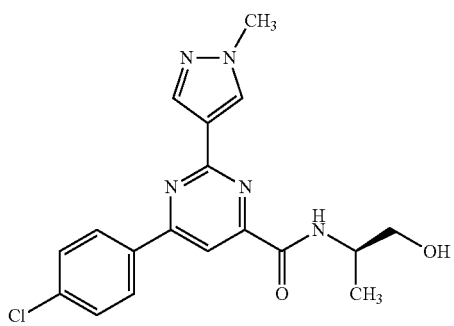 [SMILES: C[C@H](CO)NC(=O)c1cc(-c2ccc(Cl)cc2)nc(-c2cnn(C)c2)n1]

2-Chloro-6-(4-chlorophenyl)-N-[(2R)-1-hydroxypropan-2-yl]pyrimidine-4-carboxamide (160 mg, 491 µmol) and (1-methyl-1H-pyrazol-4-yl)boronic acid (92.7 mg, 736 µmol) were dissolved in 7.8 mL dioxane, aqueous sodium carbonate solution (740 µL, 2.0 M, 1.5 mmol) and tetrakis(triphenylphosphine)palladium(0) (56.7 mg, 49.1 µmol) were added. The mixture was stirred for 4 h at 90° C. The mixture was concentrated under reduced pressure. The residue was purified by preparative HPLC to give 50.9 mg (100% purity, 28% yield) of the title compound.

LC-MS (Method 1): $R_t$=1.11 min; MS (ESIpos): m/z=372 [M+H]$^+$ $^1$H-NMR (400 MHz, DMSO-d6): δ [ppm]=1.22 (d, 3H), 3.44-3.58 (m, 2H), 3.96 (s, 3H), 4.04-4.16 (m, 1H), 4.89-4.94 (m, 1H), 7.62-7.67 (m, 2H), 8.23 (s, 1H), 8.35-8.41 (m, 3H), 8.61 (d, 1H), 8.66 (s, 1H)

Example 13

6-(4-chlorophenyl)-N-(2-hydroxy-2-methylpropyl)-2-(1-methyl-1H-pyrazol-4-yl)pyrimidine-4-carboxamide

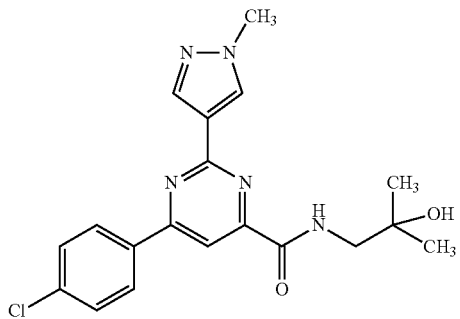 [SMILES: Cn1cc(-c2nc(C(=O)NCC(C)(C)O)cc(-c3ccc(Cl)cc3)n2)cn1]

2-Chloro-6-(4-chlorophenyl)-N-(2-hydroxy-2-methylpropyl)pyrimidine-4-carboxamide (750 mg, 60% purity, 1.32 mmol) and (1-methyl-1H-pyrazol-4-yl)boronic acid (250 mg, 1.98 mmol) were dissolved in 3 mL dioxane, aqueous sodium carbonate solution (2.0 mL, 2.0 M, 4.0 mmol) and tetrakis(triphenylphosphine)palladium(0) (153 mg, 132 µmol) were added. The mixture was stirred for 2 h at 90° C. The reaction was diluted with water and the aqueous mixture was extracted twice with DCM. The organic layer was dried over a silicone filter and concentrated under reduced pressure. The residue was dissolved in DMSO, filtered and purified by preparative HPLC to give 93.0 mg (95% purity, 17% yield) of the title compound.

LC-MS (Method 1): $R_t$=1.13 min; MS (ESIpos): m/z=386 [M+H]$^+$ $^1$H-NMR (400 MHz, DMSO-d6): δ [ppm]=1.15 (s, 6H), 3.36 (d, 2H), 3.96 (s, 3H), 4.75 (s, 1H), 7.60-7.67 (m, 2H), 8.24 (s, 1H), 8.29 (s, 1H), 8.39 (d, 2H), 8.62 (s, 1H), 8.78 (t, 1H)

Example 14

N-(2-hydroxy-2-methylpropyl)-2-(6-methoxypyridin-3-yl)-6-[4-(trifluoromethoxy)phenyl]pyrimidine-4-carboxamide

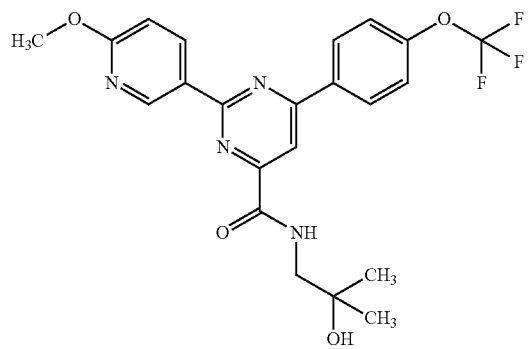 [SMILES: COc1ccc(-c2nc(C(=O)NCC(C)(C)O)cc(-c3ccc(OC(F)(F)F)cc3)n2)cn1]

To (6-methoxypyridin-3-yl)boronic acid (45.9 mg, 300 µmol) a solutions of 2-chloro-N-(2-hydroxy-2-methylpropyl)-6-[4-(trifluoromethoxy)phenyl]pyrimidine-4-carboxamide (intermediate 5, 58.5 mg, 150 µmol) in 1 mL of dioxane, sodium carbonate in 0.225 mL of water and Tetrakis(triphenylphosphin)palladium(0) (34.7 mg, 30.0 µmol) in 1 mL of dioxane were added. The reaction was heated for 12 h to 90° C. The crude mixture was filtered through a pad of Celite and purified by preparative HPLC to give the title compound 9.15 mg (99% purity, 13% yield).

LC-MS (method 2): $R_t$=1.42 min; MS (ESIpos): m/z=463 [M+H]$^+$

The following examples were prepared in analogy to example 14:

| Example | Structure IUPAC-Name LC-MS (method): Retention time; Mass found ¹H-NMR |
|---|---|
| Example 15 | 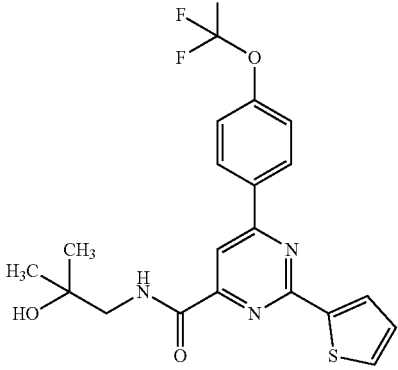<br>N-(2-hydroxy-2-methylpropyl)-2-(thiophen-2-yl)-6-[4-(trifluoromethoxy)phenyl]pyrimidine-4-carboxamide<br>LC-MS (method 2): $R_t$ = 1.44 min;<br>MS (ESIpos): m/z = 438 [M + H]⁺ |
| Example 16 | 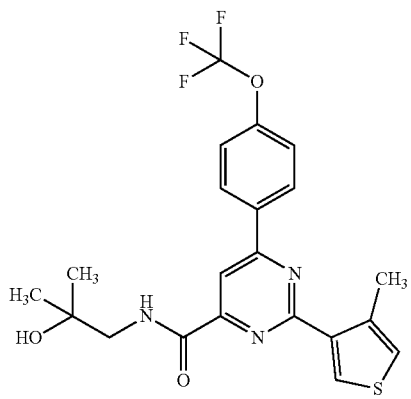 [SMILES: Cc1cscc1-c1nc(C(=O)NCC(C)(C)O)cc(-c2ccc(OC(F)(F)F)cc2)n1]<br>N-(2-hydroxy-2-methylpropyl)-2-(4-methylthiophen-3-yl)-6-[4-(trifluoromethoxy)phenyl]pyrimidine-4-carboxamide<br>LC-MS (method 2): $R_t$ = 1.51 min; MS (ESIpos):<br>m/z = 452 [M + H]⁺ |
| Example 17 | 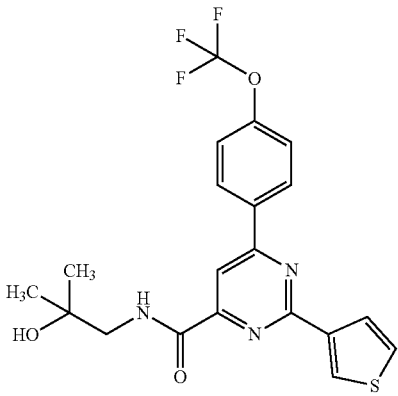 [SMILES: CC(C)(O)CNC(=O)c1cc(-c2ccc(OC(F)(F)F)cc2)nc(-c2ccsc2)n1]<br>N-(2-hydroxy-2-methylpropyl)-2-(thiophen-3-yl)-6-[4-(trifluoromethoxy)phenyl]pyrimidine-4-carboxamide<br>LC-MS (method 2): $R_t$ = 1.44 min; MS (ESIpos):<br>m/z = 438 [M + H]⁺ |
| Example 18 | 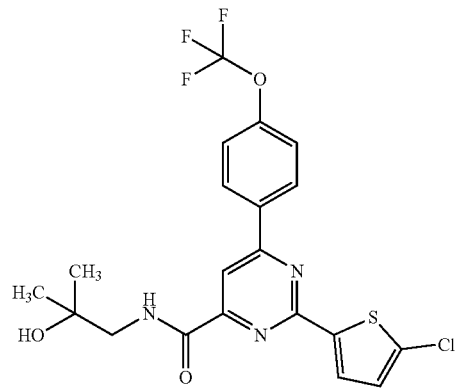 [SMILES: CC(C)(O)CNC(=O)c1cc(-c2ccc(OC(F)(F)F)cc2)nc(-c2ccc(Cl)s2)n1]<br>2-(5-chlorothiophen-2-yl)-N-(2-hydroxy-2-methylpropyl)-6-[4-(trifluoromethoxy)phenyl]pyrimidine-4-carboxamide<br>LC-MS (method 2): $R_t$ = 1.57 min; MS (ESIpos):<br>m/z = 472 [M + H]⁺ |
| Example 19 | 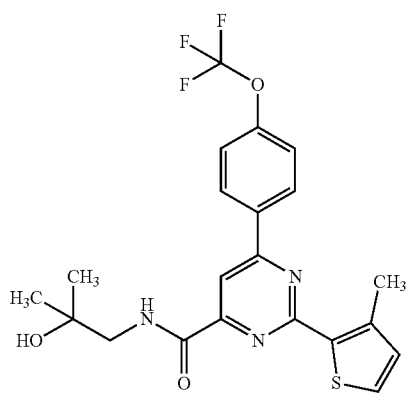 [SMILES: Cc1ccsc1-c1nc(C(=O)NCC(C)(C)O)cc(-c2ccc(OC(F)(F)F)cc2)n1]<br>N-(2-hydroxy-2-methylpropyl)-2-(3-methylthiophen-2-yl)-6-[4-(trifluoromethoxy)phenyl]pyrimidine-4-carboxamide<br>LC-MS (method 2): $R_t$ = 1.51 min; MS (ESIpos):<br>m/z = 452 [M + H]⁺ |
| Example 20 | 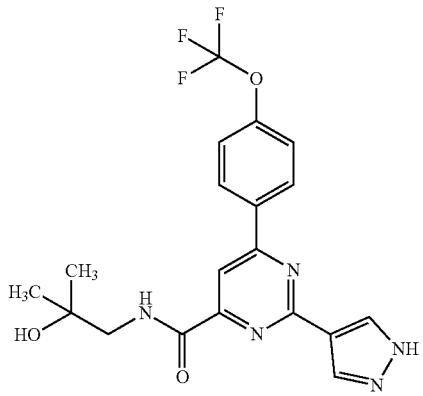 [SMILES: CC(C)(O)CNC(=O)c1cc(-c2ccc(OC(F)(F)F)cc2)nc(-c2cn[nH]c2)n1]<br>N-(2-hydroxy-2-methylpropyl)-2-(1H-pyrazol-4-yl)-6-[4-(trifluoromethoxy)phenyl]pyrimidine-4-carboxamide<br>LC-MS (method 2): $R_t$ = 1.13 min; MS (ESIpos):<br>m/z = 422 [M + H]⁺ |

| Example | Structure / IUPAC-Name / LC-MS (method): Retention time; Mass found / 1H-NMR |
|---|---|
| Example 21 | 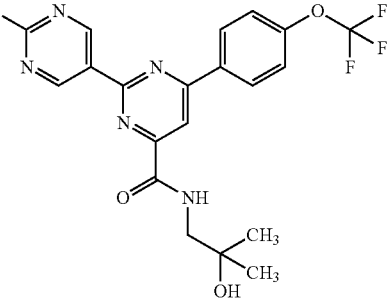 N-(2-hydroxy-2-methylpropyl)-2'-methyl-6-[4-(trifluoromethoxy)phenyl][2,5'-bipyrimidine]-4-carboxamide<br>LC-MS (method 2): $R_t$ = 1.23 min; MS (ESIpos): m/z = 448 [M + H]⁺ |
| Example 22 | 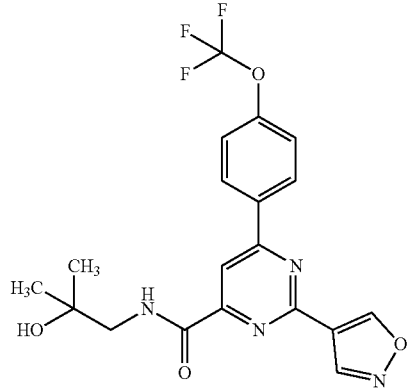 [SMILES: CC(C)(O)CNC(=O)c1cc(-c2ccc(OC(F)(F)F)cc2)nc(-c2cnoc2)n1] N-(2-hydroxy-2-methylpropyl)-2-(1,2-oxazol-4-yl)-6-[4-(trifluoromethoxy)phenyl]pyrimidine-4-carboxamide<br>LC-MS (method 2): $R_t$ = 1.16 min; MS (ESIpos): m/z = 423 [M + H]⁺ |
| Example 23 | 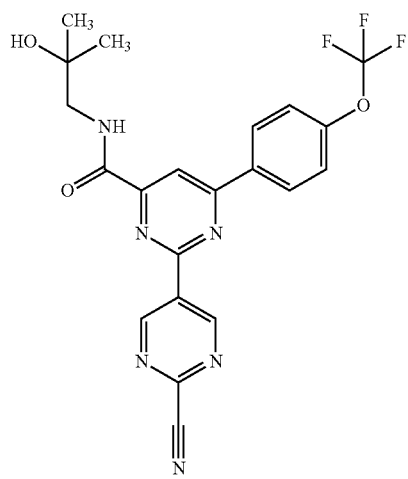 [SMILES: CC(C)(O)CNC(=O)c1cc(-c2ccc(OC(F)(F)F)cc2)nc(-c2cnc(C#N)nc2)n1] 2'-cyano-N-(2-hydroxy-2-methylpropyl)-6-[4-(trifluoromethoxy)phenyl][2,5'-bipyrimidine]-4-carboxamide<br>LC-MS (method 2): $R_t$ = 1.32 min; MS (ESIpos): m/z = 459 [M + H]⁺ |
| Example 24 | 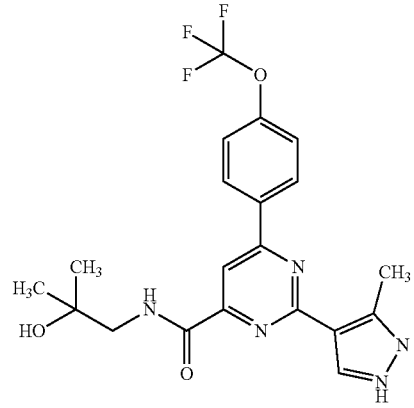 [SMILES: Cc1[nH]ncc1-c1nc(C(=O)NCC(C)(C)O)cc(-c2ccc(OC(F)(F)F)cc2)n1] N-(2-hydroxy-2-methylpropyl)-2-(3-methyl-1H-pyrazol-4-yl)-6-[4-(trifluoromethoxy)phenyl]pyrimidine-4-carboxamide<br>LC-MS (method 2): $R_t$ = 1.17 min; MS (ESIpos): m/z = 436 [M + H]⁺ |
| Example 25 | 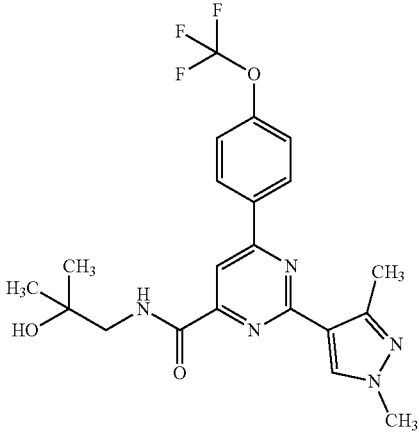 [SMILES: Cc1nn(C)cc1-c1nc(C(=O)NCC(C)(C)O)cc(-c2ccc(OC(F)(F)F)cc2)n1] 2-(1,3-dimethyl-1H-pyrazol-4-yl)-N-(2-hydroxy-2-methylpropyl)-6-[4-(trifluoromethoxy)phenyl]pyrimidine-4-carboxamide<br>LC-MS (method 2): $R_t$ = 1.25 min; MS (ESIpos): m/z = 450 [M + H]⁺ |

| Example | Structure / IUPAC-Name / LC-MS (method): Retention time; Mass found / ¹H-NMR |
|---|---|
| Example 26 | 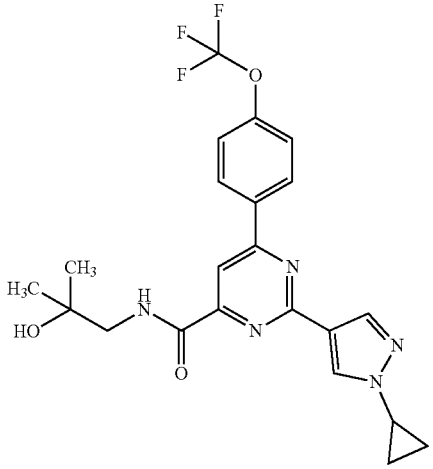 [SMILES: CC(C)(O)CNC(=O)c1cc(-c2ccc(OC(F)(F)F)cc2)nc(-c2cnn(C3CC3)c2)n1]<br>2-(1-cyclopropyl-1H-pyrazol-4-yl)-N-(2-hydroxy-2-methylpropyl)-6-[4-(trifluoromethoxy)phenyl]pyrimidine-4-carboxamide<br>LC-MS (method 2): $R_t$ = 1.31 min; MS (ESIpos):<br>m/z = 462 [M + H]⁺ |
| Example 27 | 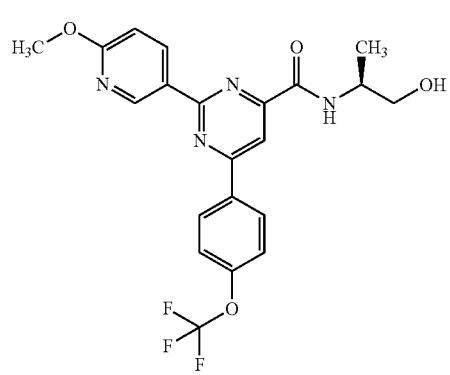 [SMILES: COc1ccc(-c2nc(C(=O)N[C@@H](C)CO)cc(-c3ccc(OC(F)(F)F)cc3)n2)cn1]<br>N-[(2S)-1-hydroxypropan-2-yl]-2-(6-methoxypyridin-3-yl)-6-[4-(trifluoromethoxy)phenyl]pyrimidine-4-carboxamide<br>LC-MS (method 2): $R_t$ = 1.38 min; MS (ESIpos):<br>m/z = 449 [M + H]⁺ |
| Example 28 | 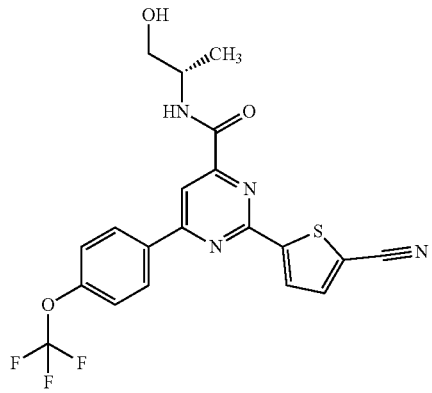 [SMILES: C[C@@H](CO)NC(=O)c1cc(-c2ccc(OC(F)(F)F)cc2)nc(-c2ccc(C#N)s2)n1]<br>2-(5-cyanothiophen-2-yl)-N-[(2S)-1-hydroxypropan-2-yl]-6-[4-(trifluoromethoxy)phenyl]pyrimidine-4-carboxamide<br>LC-MS (method 2): $R_t$ = 1.38 min; MS (ESIpos):<br>m/z = 449 [M + H]⁺ |
| Example 29 | 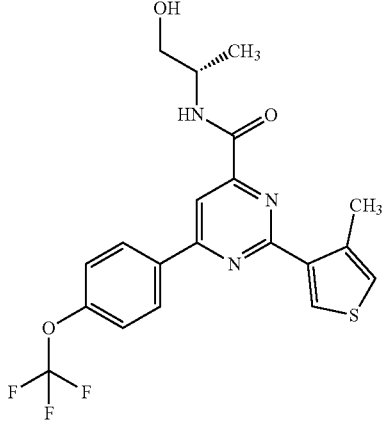 [SMILES: Cc1cscc1-c1nc(C(=O)N[C@@H](C)CO)cc(-c2ccc(OC(F)(F)F)cc2)n1]<br>N-[(2S)-1-hydroxypropan-2-yl]-2-(4-methylthiophen-3-yl)-6-[4-(trifluoromethoxy)phenyl]pyrimidine-4-carboxamide<br>LC-MS (method 2): $R_t$ = 1.48 min; MS (ESIpos):<br>m/z = 438 [M + H]⁺ |
| Example 30 | 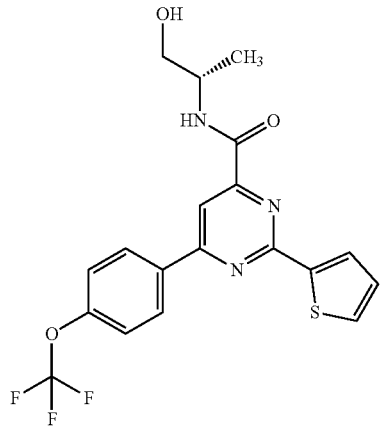 [SMILES: C[C@@H](CO)NC(=O)c1cc(-c2ccc(OC(F)(F)F)cc2)nc(-c2cccs2)n1]<br>N-[(2S)-1-hydroxypropan-2-yl]-2-(thiophen-2-yl)-6-[4-(trifluoromethoxy)phenyl]pyrimidine-4-carboxamide<br>LC-MS (method 2): $R_t$ = 1.40 min; MS (ESIpos):<br>m/z = 424 [M + H]⁺ |

| Example | Structure<br>IUPAC-Name<br>LC-MS (method): Retention time; Mass found<br>¹H-NMR |
|---|---|
| Example 31 | 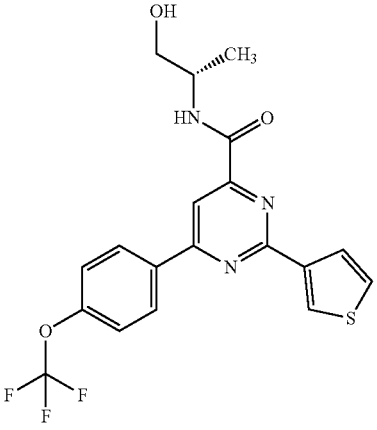 [SMILES: C[C@@H](CO)NC(=O)c1cc(-c2ccc(OC(F)(F)F)cc2)nc(-c2ccsc2)n1]<br>N-[(2S)-1-hydroxypropan-2-yl]-2-(thiophen-3-yl)-6-[4-(trifluoromethoxy)phenyl]pyrimidine-4-carboxamide<br>LC-MS (method 2): $R_t$ = 1.41 min; MS (ESIpos):<br>m/z = 424 [M + H]⁺ |
| Example 32 | 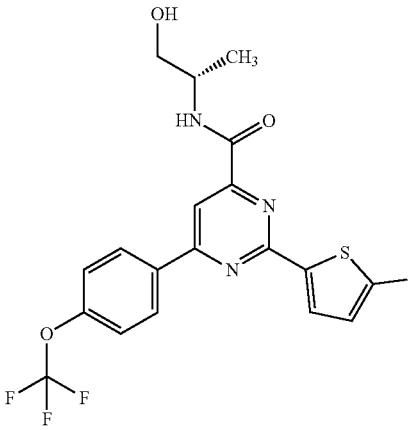<br>2-(5-chlorothiophen-2-yl)-N-[(2S)-1-hydroxypropan-2-yl]-6-[4-(trifluoromethoxy)phenyl]pyrimidine-4-carboxamide<br>LC-MS (method 2): $R_t$ = 1.55 min; MS (ESIpos):<br>m/z = 458 [M + H]⁺ |
| Example 33 | 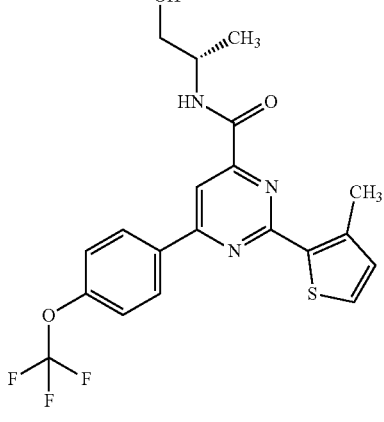<br>N-[(2S)-1-hydroxypropan-2-yl]-2-(3-methylthiophen-2-yl)-6-[4-(trifluoromethoxy)phenyl]pyrimidine-4-carboxamide<br>LC-MS (method 2): $R_t$ = 1.48 min; MS (ESIpos):<br>m/z = 438 [M + H]⁺ |
| Example 34 | 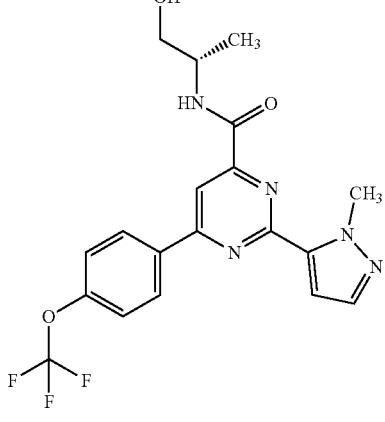<br>N-[(2S)-1-hydroxypropan-2-yl]-2-(1-methyl-1H-pyrazol-5-yl)-6-[4-(trifluoromethoxy)phenyl]pyrimidine-4-carboxamide<br>LC-MS (method 2): $R_t$ = 1.22 min; MS (ESIpos):<br>m/z = 422 [M + H]⁺ |

| Example | Structure / IUPAC-Name / LC-MS (method): Retention time; Mass found / ¹H-NMR |
|---|---|
| Example 35 | 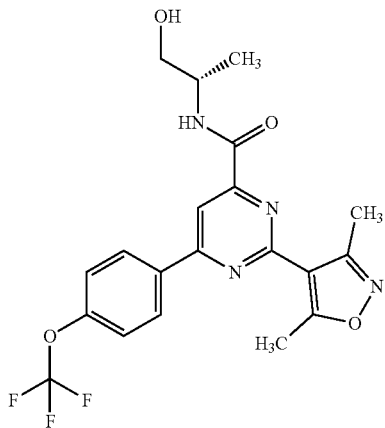 [SMILES: Cc1noc(C)c1-c1nc(C(=O)N[C@@H](C)CO)cc(-c2ccc(OC(F)(F)F)cc2)n1]<br>2-(3,5-dimethyl-1,2-oxazol-4-yl)-N-[(2S)-1-hydroxypropan-2-yl]-6-[4-(trifluoromethoxy)phenyl]pyrimidine-4-carboxamide<br>LC-MS (method 2): $R_t$ = 1.34 min; MS (ESIpos): m/z = 437 [M + H]⁺ |
| Example 36 | 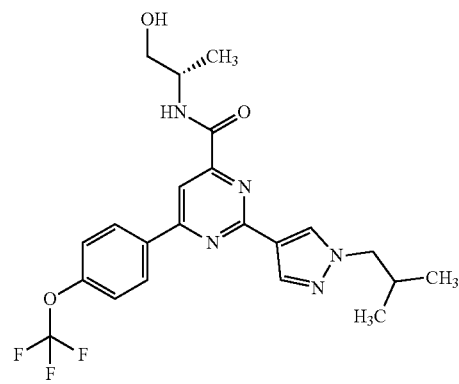 [SMILES: CC(C)Cn1cc(-c2nc(C(=O)N[C@@H](C)CO)cc(-c3ccc(OC(F)(F)F)cc3)n2)cn1]<br>N-[(2S)-1-hydroxypropan-2-yl]-2-[1-(2-methylpropyl)-1H-pyrazol-4-yl]-6-[4-(trifluoromethoxy)phenyl]pyrimidine-4-carboxamide<br>LC-MS (method 2): $R_t$ = 1.37 min; MS (ESIpos): m/z = 464 [M + ]⁺ |
| Example 37 | 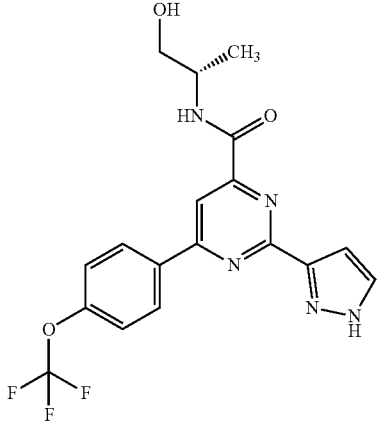 [SMILES: C[C@@H](CO)NC(=O)c1cc(-c2ccc(OC(F)(F)F)cc2)nc(-c2cc[nH]n2)n1]<br>N-[(2S)-1-hydroxypropan-2-yl]-2-(1H-pyrazol-3-yl)-6-[4-(trifluoromethoxy)phenyl]pyrimidine-4-carboxamide<br>LC-MS (method 2): $R_t$ = 1.13 min; MS (ESIpos): m/z = 408 [M + H]⁺ |
| Example 38 | 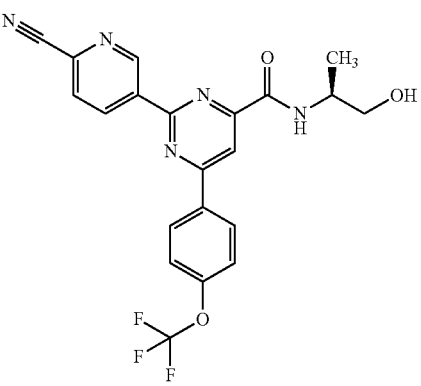 [SMILES: C[C@@H](CO)NC(=O)c1cc(-c2ccc(OC(F)(F)F)cc2)nc(-c2ccc(C#N)nc2)n1]<br>2-(6-cyanopyridin-3-yl)-N-[(2S)-1-hydroxypropan-2-yl]-6-[4-(trifluoromethoxy)phenyl]pyrimidine-4-carboxamide<br>LC-MS (method 2): $R_t$ = 1.29 min; MS (ESIpos): m/z = 444 [M + H]⁺ |
| Example 39 | 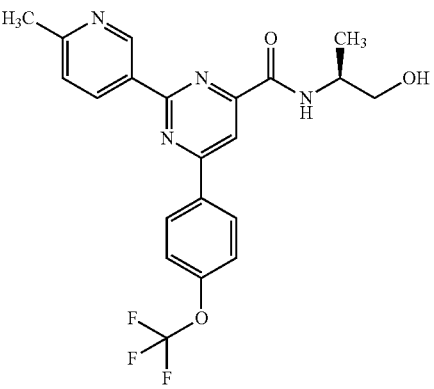 [SMILES: Cc1ccc(-c2nc(C(=O)N[C@@H](C)CO)cc(-c3ccc(OC(F)(F)F)cc3)n2)cn1]<br>N-[(2S)-1-hydroxypropan-2-yl]-2-(6-methylpyridin-3-yl)-6-[4-(trifluoromethoxy)phenyl]pyrimidine-4-carboxamide<br>LC-MS (method 2): $R_t$ = 1.09 min; MS (ESIpos): m/z = 433 [M + H]⁺ |

| Example | Structure<br>IUPAC-Name<br>LC-MS (method): Retention time; Mass found<br>¹H-NMR |
|---|---|
| Example 40 | 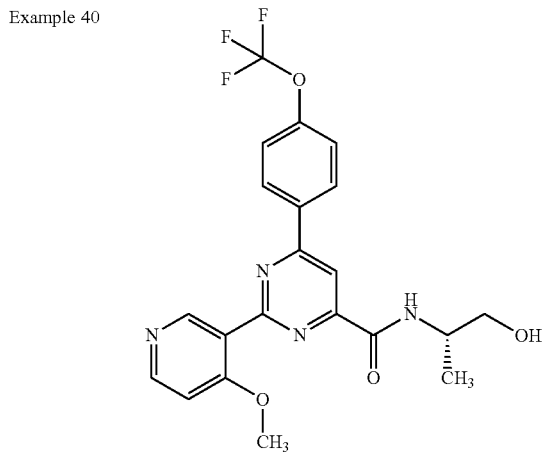<br>N-[(2S)-1-hydroxypropan-2-yl]-2-(4-methoxypyridin-3-yl)-6-[4-(trifluoromethoxy)phenyl]pyrimidine-4-carboxamide<br>LC-MS (method 2): $R_t$ = 0.87 min; MS (ESIpos): m/z = 449 [M + H]⁺ |
| Example 41 | 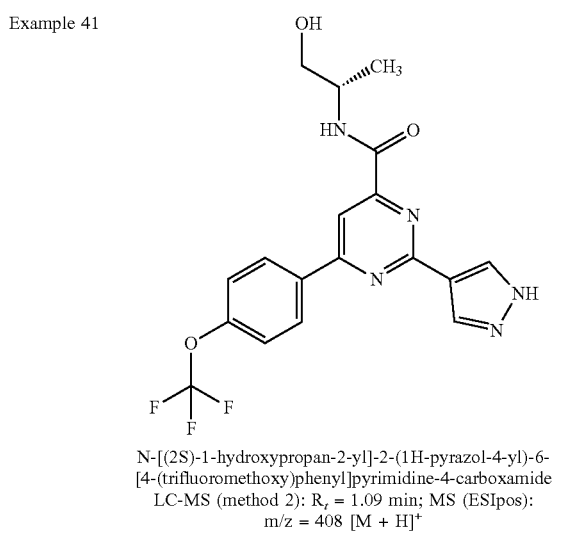<br>N-[(2S)-1-hydroxypropan-2-yl]-2-(1H-pyrazol-4-yl)-6-[4-(trifluoromethoxy)phenyl]pyrimidine-4-carboxamide<br>LC-MS (method 2): $R_t$ = 1.09 min; MS (ESIpos): m/z = 408 [M + H]⁺ |
| Example 42 | 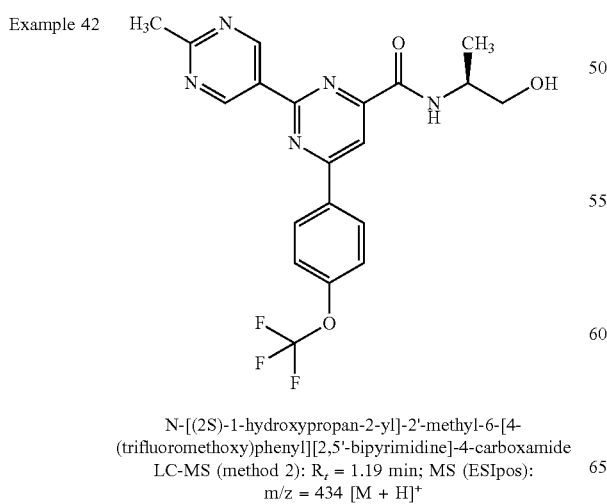<br>N-[(2S)-1-hydroxypropan-2-yl]-2'-methyl-6-[4-(trifluoromethoxy)phenyl][2,5'-bipyrimidine]-4-carboxamide<br>LC-MS (method 2): $R_t$ = 1.19 min; MS (ESIpos): m/z = 434 [M + H]⁺ |
| Example 43 | 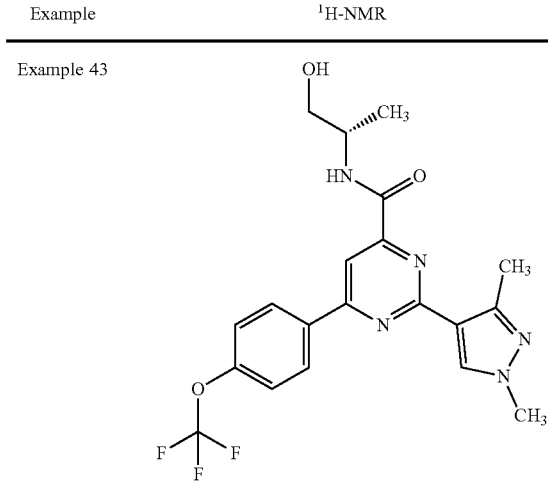<br>2-(1,3-dimethyl-1H-pyrazol-4-yl)-N-[(2S)-1-hydroxypropan-2-yl]-6-[4-(trifluoromethoxy)phenyl]pyrimidine-4-carboxamide<br>LC-MS (method 2): $R_t$ = 1.22 min; MS (ESIpos): m/z = 436 [M + H]⁺ |
| Example 44 | 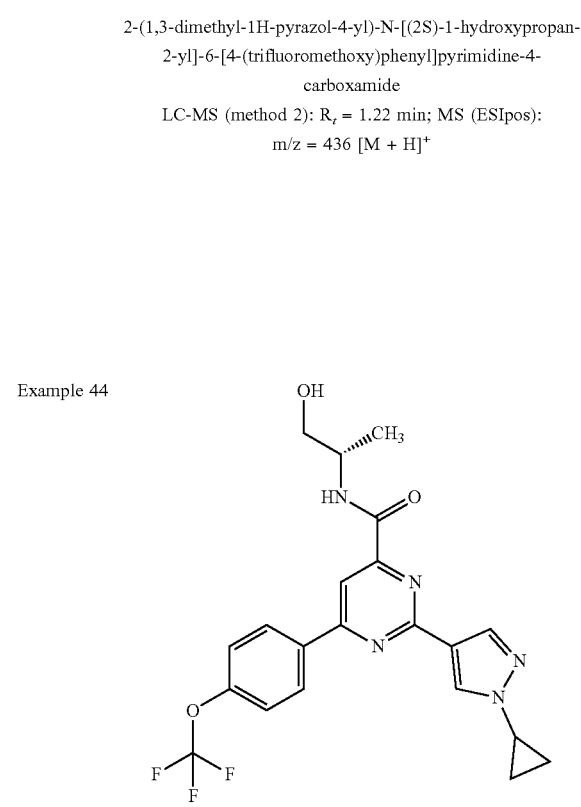<br>2-(1-cyclopropyl-1H-pyrazol-4-yl)-N-[(2S)-1-hydroxypropan-2-yl]-6-[4-(trifluoromethoxy)phenyl]pyrimidine-4-carboxamide<br>LC-MS (method 2): $R_t$ = 1.27 min; MS (ESIpos): m/z = 448 [M + H]⁺ |

| Example | Structure IUPAC-Name LC-MS (method): Retention time; Mass found ¹H-NMR |
|---|---|
| Example 45 | 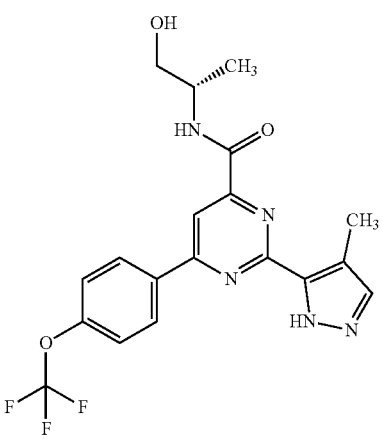 [SMILES: Cc1cn[nH]c1-c1nc(C(=O)N[C@@H](C)CO)cc(-c2ccc(OC(F)(F)F)cc2)n1]<br>N-[(2S)-1-hydroxypropan-2-yl]-2-(4-methyl-1H-pyrazol-5-yl)-6-[4-(trifluoromethoxy)phenyl]pyrimidine-4-carboxamide<br>LC-MS (method 2): R$_t$ = 1.22 min; MS (ESIpos): m/z = 422 [M + H]⁺ |
| Example 46 | 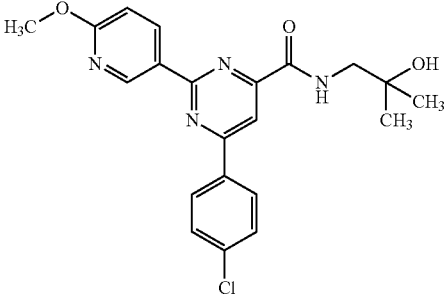 [SMILES: COc1ccc(-c2nc(C(=O)NCC(C)(C)O)cc(-c3ccc(Cl)cc3)n2)cn1]<br>6-(4-chlorophenyl)-N-(2-hydroxy-2-methylpropyl)-2-(6-methoxypyridin-3-yl)pyrimidine-4-carboxamide<br>LC-MS (method 2): R$_t$ = 1.35 min; MS (ESIpos): m/z = 413 [M + H]⁺ |
| Example 47 | 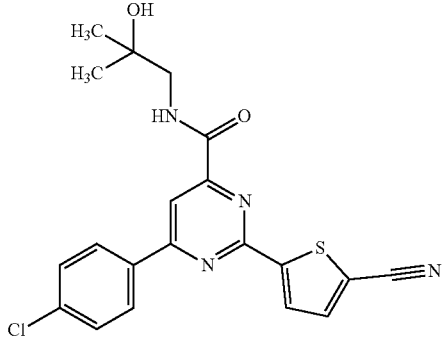 [SMILES: CC(C)(O)CNC(=O)c1cc(-c2ccc(Cl)cc2)nc(-c2ccc(C#N)s2)n1]<br>6-(4-chlorophenyl)-2-(5-cyanothiophen-2-yl)-N-(2-hydroxy-2-methylpropyl)pyrimidine-4-carboxamide<br>LC-MS (method 2): R$_t$ = 1.35 min; MS (ESIpos): m/z = 413 [M + H]⁺ |
| Example 48 | 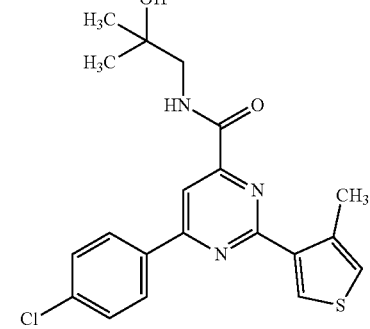<br>6-(4-chlorophenyl)-N-(2-hydroxy-2-methylpropyl)-2-(4-methylthiophen-3-yl)pyrimidine-4-carboxamide<br>LC-MS (method 2): R$_t$ = 1.45 min; MS (ESIpos): m/z = 402 [M + H]⁺ |
| Example 49 | 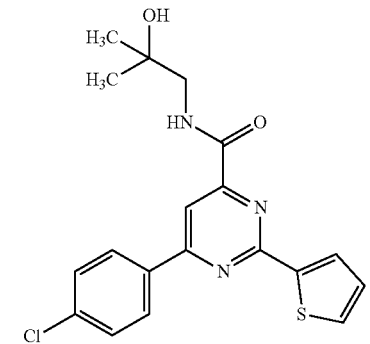 [SMILES: CC(C)(O)CNC(=O)c1cc(-c2ccc(Cl)cc2)nc(-c2cccs2)n1]<br>6-(4-chlorophenyl)-N-(2-hydroxy-2-methylpropyl)-2-(thiophen-2-yl)pyrimidine-4-carboxamide<br>LC-MS (method 2): R$_t$ = 1.37 min; MS (ESIpos): m/z = 388 [M + H]⁺ |
| Example 50 | 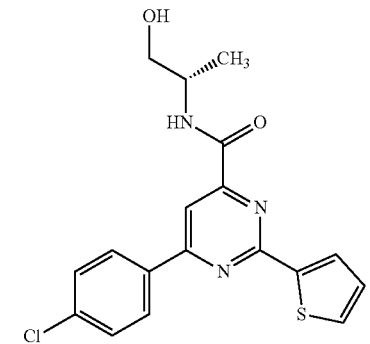 [SMILES: C[C@@H](CO)NC(=O)c1cc(-c2ccc(Cl)cc2)nc(-c2cccs2)n1]<br>6-(4-chlorophenyl)-N-[(2S)-1-hydroxypropan-2-yl]-2-(thiophen-2-yl)pyrimidine-4-carboxamide<br>LC-MS (method 2): R$_t$ = 1.33 min; MS (ESIpos): m/z = 374 [M + H]⁺ |

| Example | Structure / IUPAC-Name / LC-MS (method): Retention time; Mass found / ¹H-NMR |
|---|---|
| Example 51 | 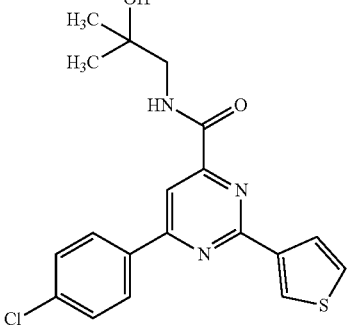<br>6-(4-chlorophenyl)-N-(2-hydroxy-2-methylpropyl)-2-(thiophen-3-yl)pyrimidine-4-carboxamide<br>LC-MS (method 2): $R_t$ = 1.37 min; MS (ESIpos): m/z = 388 [M + H]⁺ |
| Exampe 52 | 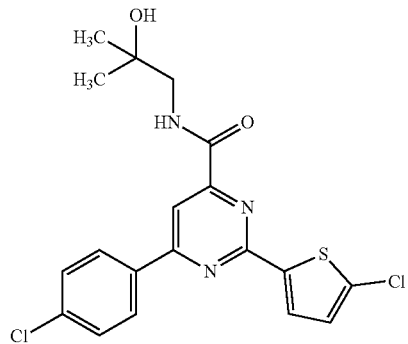 [SMILES: CC(C)(O)CNC(=O)c1cc(-c2ccc(Cl)cc2)nc(-c2ccc(Cl)s2)n1]<br>6-(4-chlorophenyl)-2-(5-chlorothiophen-2-yl)-N-(2-hydroxy-2-methylpropyl)pyrimidine-4-carboxamide<br>LC-MS (method 2): $R_t$ = 1.53 min; MS (ESIpos): m/z = 422 [M + H]⁺ |
| Example 53 | 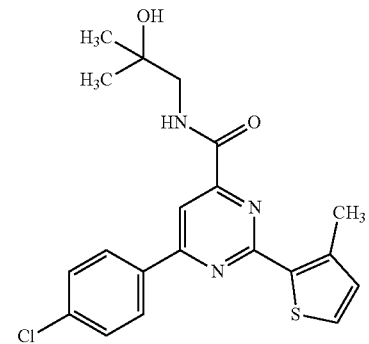 [SMILES: Cc1ccsc1-c1nc(C(=O)NCC(C)(C)O)cc(-c2ccc(Cl)cc2)n1]<br>6-(4-chlorophenyl)-N-(2-hydroxy-2-methylpropyl)-2-(3-methylthiophen-2-yl)pyrimidine-4-carboxamide<br>LC-MS (method 2): $R_t$ = 1.45 min; MS (ESIpos): m/z = 402 [M + H]⁺ |
| Example 54 | 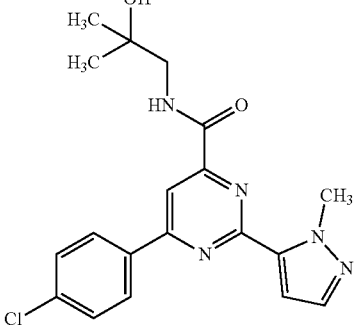<br>6-(4-chlorophenyl)-N-(2-hydroxy-2-methylpropyl)-2-(1-methyl-1H-pyrazol-5-yl)pyrimidine-4-carboxamide<br>LC-MS (method 2): $R_t$ = 1.18 min; MS (ESIpos): m/z = 386 [M + H]⁺ |
| Example 55 | 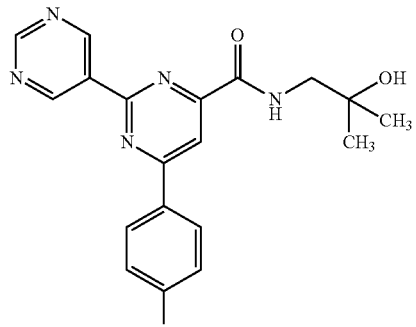<br>6-(4-chlorophenyl)-N-(2-hydroxy-2-methylpropyl)[2,5'-bipyrimidine]-4-carboxamide<br>LC-MS (method 2): $R_t$ = 1.10 min; MS (ESIpos): m/z = 384 [M + H]⁺ |
| Example 56 | 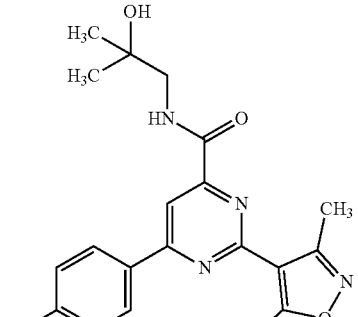<br>6-(4-chlorophenyl)-2-(3,5-dimethyl-1,2-oxazol-4-yl)-N-(2-hydroxy-2-methylpropyl)pyrimidine-4-carboxamide<br>LC-MS (method 2): $R_t$ = 1.30 min; MS (ESIpos): m/z = 401 [M + H]⁺ |

| Example | Structure / IUPAC-Name / LC-MS (method): Retention time; Mass found / ¹H-NMR |
|---|---|
| Example 57 | 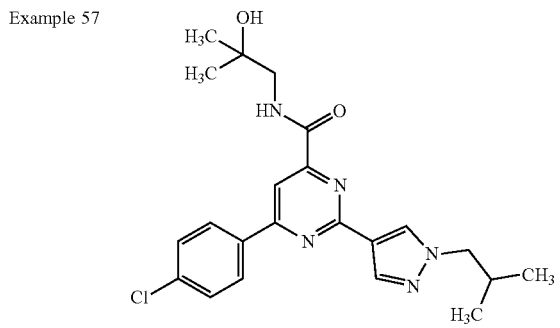<br>6-(4-chlorophenyl)-N-(2-hydroxy-2-methylpropyl)-2-[1-(2-methylpropyl)-1H-pyrazol-4-yl]pyrimidine-4-carboxamide<br>LC-MS (method 2): $R_t$ = 1.34 min; MS (ESIpos): m/z = 428 [M + H]⁺ |
| Example 58 | 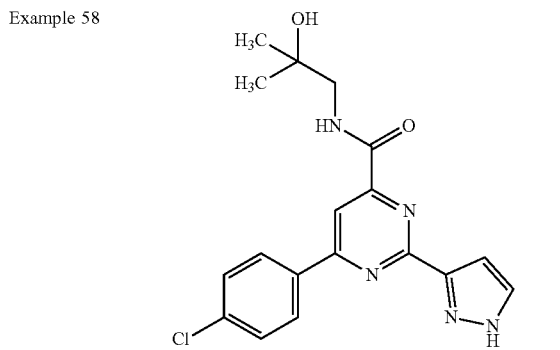<br>6-(4-chlorophenyl)-N-(2-hydroxy-2-methylpropyl)-2-(1H-pyrazol-3-yl)pyrimidine-4-carboxamide<br>LC-MS (method 2): $R_t$ = 1.09 min; MS (ESIpos): m/z = 372 [M + H]⁺ |
| Example 59 | 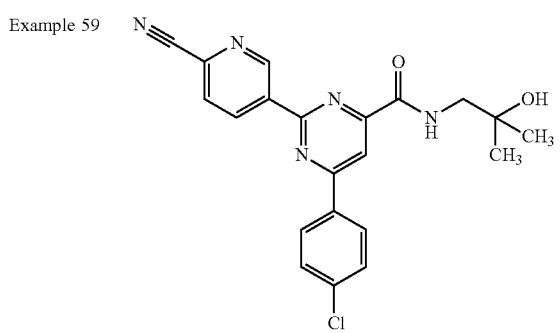<br>6-(4-chlorophenyl)-2-(6-cyanopyridin-3-yl)-N-(2-hydroxy-2-methylpropyl)pyrimidine-4-carboxamide<br>LC-MS (method 2): $R_t$ = 1.25 min; MS (ESIpos): m/z = 408 [M + H]⁺ |
| Example 60 | 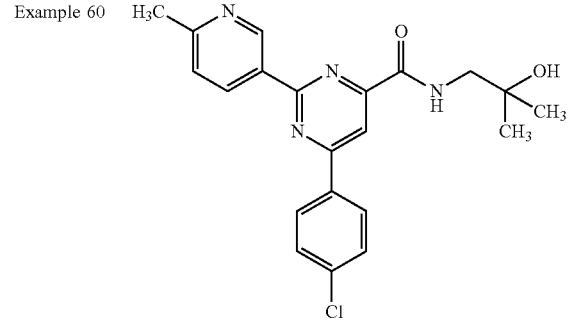<br>6-(4-chlorophenyl)-N-(2-hydroxy-2-methylpropyl)-2-(6-methylpyridin-3-yl)pyrimidine-4-carboxamide<br>LC-MS (method 2): $R_t$ = 1.04 min; MS (ESIpos): m/z = 397 [M + H]⁺ |
| Example 61 | 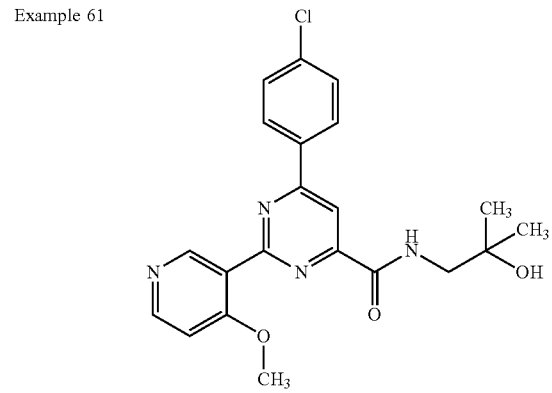<br>6-(4-chlorophenyl)-N-(2-hydroxy-2-methylpropyl)-2-(4-methoxypyridin-3-yl)pyrimidine-4-carboxamide<br>LC-MS (method 2): $R_t$ = 0.82 min; MS (ESIpos): m/z = 413 [M + H]⁺ |
| Example 62 | 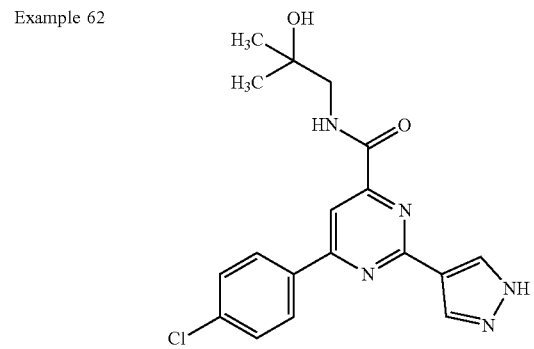<br>6-(4-chlorophenyl)-N-(2-hydroxy-2-methylpropyl)-2-(1H-pyrazol-4-yl)pyrimidine-4-carboxamide<br>LC-MS (method 2): $R_t$ = 1.03 min; MS (ESIpos): m/z = 372 [M + H]⁺ |

| Example | Structure<br>IUPAC-Name<br>LC-MS (method): Retention time; Mass found<br>$^1$H-NMR |
|---|---|
| Example 63 | 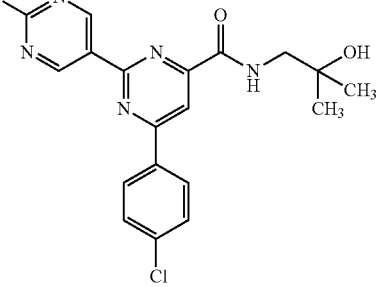<br>6-(4-chlorophenyl)-N-(2-hydroxy-2-methylpropyl)-2'-methyl[2,5'-bipyrimidine]-4-carboxamide<br>LC-MS (method 2): R$_t$ = 1.14 min; MS (ESIpos):<br>m/z = 398 [M + H]$^+$ |
| Example 64 | 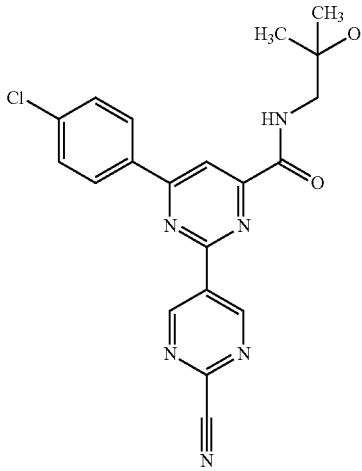<br>6-(4-chlorophenyl)-2'-cyano-N-(2-hydroxy-2-methyl-propyl)[2,5'-bipyrimidine]-4-carboxamide<br>LC-MS (method 2): R$_t$ = 1.25 min; MS (ESIpos):<br>m/z = 409 [M + H]$^+$ |
| Example 65 | 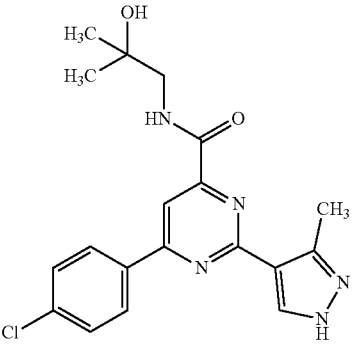 [SMILES: Cc1n[nH]cc1-c1nc(C(=O)NCC(C)(C)O)cc(-c2ccc(Cl)cc2)n1]<br>6-(4-chlorophenyl)-N-(2-hydroxy-2-methylpropyl)-2-(3-methyl-1H-pyrazol-4-yl)pyrimidine-4-carboxamide<br>LC-MS (method 2): R$_t$ = 1.08 min; MS (ESIpos):<br>m/z = 386 [M + H]$^+$ |
| Example 66 | 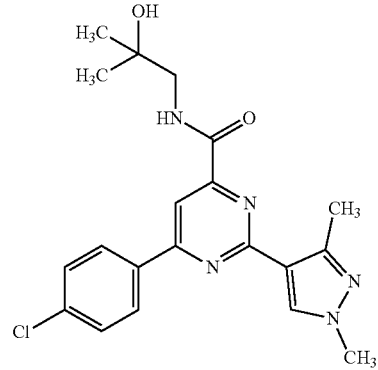 [SMILES: Cc1nn(C)cc1-c1nc(C(=O)NCC(C)(C)O)cc(-c2ccc(Cl)cc2)n1]<br>6-(4-chlorophenyl)-2-(1,3-dimethyl-1H-pyrazol-4-yl)-N-(2-hydroxy-2-methylpropyl)pyrimidine-4-carboxamide<br>LC-MS (method 2): R$_t$ = 1.17 min; MS (ESIpos):<br>m/z = 400 [M + H]$^+$ |
| Example 67 | 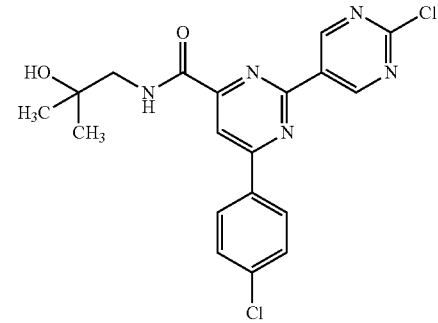 [SMILES: CC(C)(O)CNC(=O)c1cc(-c2ccc(Cl)cc2)nc(-c2cnc(Cl)nc2)n1]<br>2'-chloro-6-(4-chlorophenyl)-N-(2-hydroxy-2-methyl-propyl)[2,5'-bipyrimidine]-4-carboxamide<br>LC-MS (method 2): R$_t$ = 1.28 min; MS (ESIpos):<br>m/z = 418 [M + H]$^+$ |
| Example 68 | 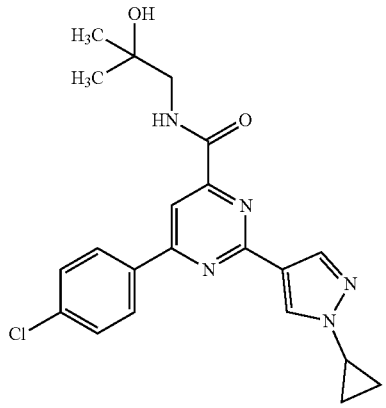 [SMILES: CC(C)(O)CNC(=O)c1cc(-c2ccc(Cl)cc2)nc(-c2cnn(C3CC3)c2)n1]<br>6-(4-chlorophenyl)-2-(1-cyclopropyl-1H-pyrazol-4-yl)-N-(2-hydroxy-2-methylpropyl)pyrimidine-4-carboxamide<br>LC-MS (method 2): R$_t$ = 1.23 min; MS (ESIpos):<br>m/z = 412 [M + H]$^+$ |

| Example | Structure<br>IUPAC-Name<br>LC-MS (method): Retention time; Mass found<br>¹H-NMR |
|---|---|
| Example 69 | 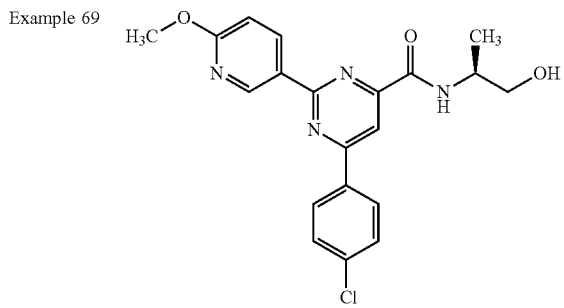<br>6-(4-chlorophenyl)-N-[(2S)-1-hydroxypropan-2-yl]-2-(6-methoxypyridin-3-yl)pyrimidine-4-carboxamide<br>LC-MS (method 2): $R_t$ = 1.31 min; MS (ESIpos): m/z = 399 [M + H]⁺ |
| Example 70 | 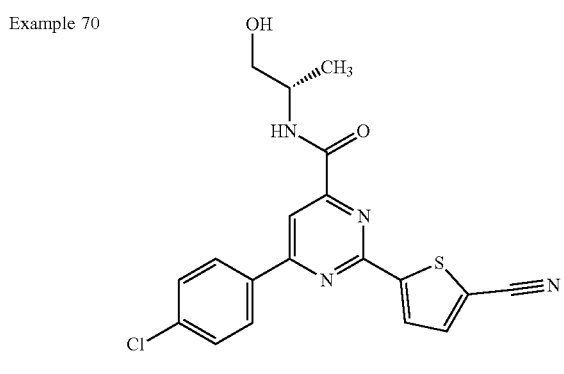<br>6-(4-chlorophenyl)-2-(5-cyanothiophen-2-yl)-N-[(2S)-1-hydroxypropan-2-yl]pyrimidine-4-carboxamide<br>LC-MS (method 2): $R_t$ = 1.31 min; MS (ESIpos): m/z = 399 [M + H]⁺ |
| Example 71 | 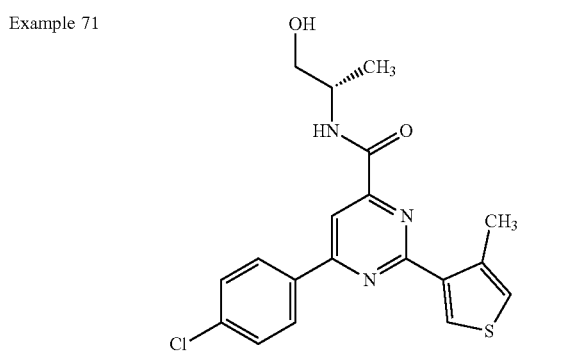<br>6-(4-chlorophenyl)-N-[(2S)-1-hydroxypropan-2-yl]-2-(4-methylthiophen-3-yl)pyrimidine-4-carboxamide<br>LC-MS (method 2): $R_t$ = 1.41 min; MS (ESIpos): m/z = 388 [M + H]⁺ |
| Example 72 | 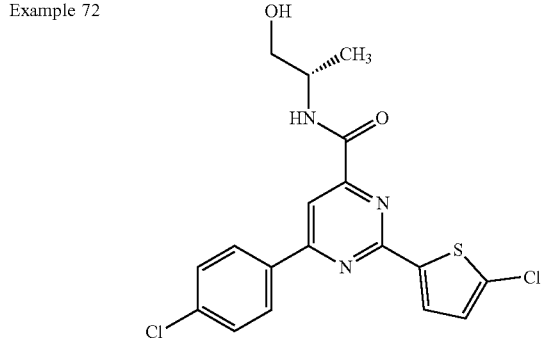<br>6-(4-chlorophenyl)-2-(5-chlorothiophen-2-yl)-N-[(2S)-1-hydroxypropan-2-yl]pyrimidine-4-carboxamide<br>LC-MS (method 2): $R_t$ = 1.49 min; MS (ESIpos): m/z = 408 [M + H]⁺ |
| Example 73 | 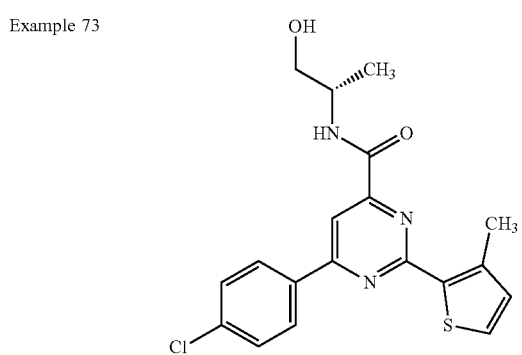<br>6-(4-chlorophenyl)-N-[(2S)-1-hydroxypropan-2-yl]-2-(3-methylthiophen-2-yl)pyrimidine-4-carboxamide<br>LC-MS (method 2): $R_t$ = 1.42 min; MS (ESIpos): m/z = 388 [M + H]⁺ |
| Example 74 | 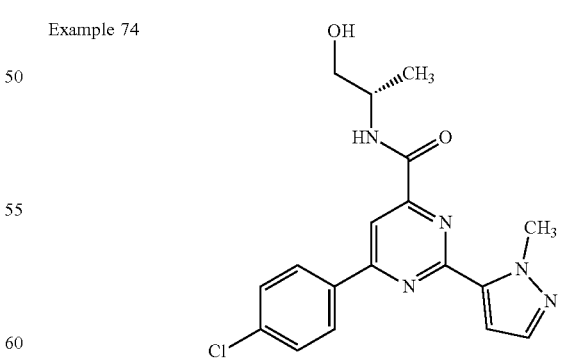<br>6-(4-chlorophenyl)-N-[(2S)-1-hydroxypropan-2-yl]-2-(1-methyl-1H-pyrazol-5-yl)pyrimidine-4-carboxamide<br>LC-MS (method 2): $R_t$ = 1.13 min; MS (ESIpos): m/z = 372 [M + H]⁺ |

| Example | Structure<br>IUPAC-Name<br>LC-MS (method): Retention time; Mass found<br>$^1$H-NMR |
|---|---|
| Example 75 | 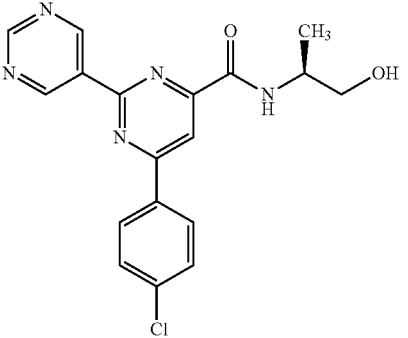 [SMILES: C[C@@H](CO)NC(=O)c1cc(-c2ccc(Cl)cc2)nc(-c2cncnc2)n1]<br>6-(4-chlorophenyl)-N-[(2S)-1-hydroxypropan-2-yl][2,5'-bipyrimidine]-4-carboxamide<br>LC-MS (method 2): $R_t$ = 1.06 min; MS (ESIpos):<br>m/z = 370 [M + H]$^+$ |
| Example 76 | 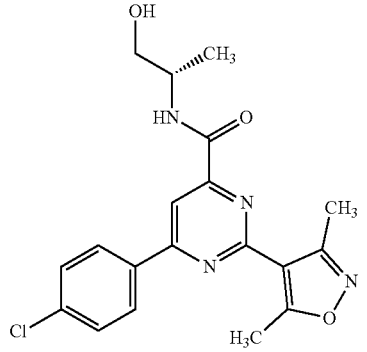 [SMILES: Cc1noc(C)c1-c1nc(C(=O)N[C@@H](C)CO)cc(-c2ccc(Cl)cc2)n1]<br>6-(4-chlorophenyl)-2-(3,5-dimethyl-1,2-oxazol-4-yl)-N-[(2S)-1-hydroxypropan-2-yl]pyrimidine-4-carboxamide<br>LC-MS (method 2): $R_t$ = 1.26 min; MS (ESIpos):<br>m/z = 387 [M + H]$^+$ |
| Example 77 | 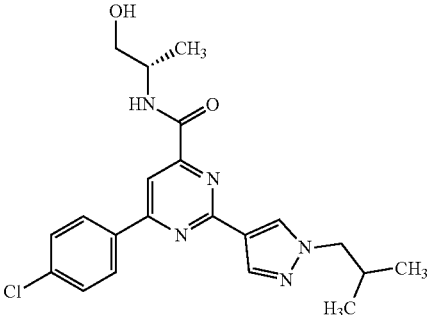<br>6-(4-chlorophenyl)-N-[(2S)-1-hydroxypropan-2-yl]-2-[1-(2-methylpropyl)-1H-pyrazol-4-yl]pyrimidine-4-carboxamide<br>LC-MS (method 2): $R_t$ = 1.30 min; MS (ESIpos):<br>m/z = 414 [M + H]$^+$ |
| Example 78 | 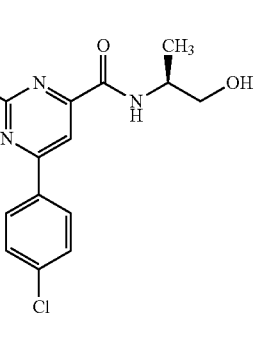<br>6-(4-chlorophenyl)-2-(6-cyanopyridin-3-yl)-N-[(2S)-1-hydroxypropan-2-yl]pyrimidine-4-carboxamide<br>LC-MS (method 2): $R_t$ = 1.22 min; MS (ESIpos):<br>m/z = 394 [M + H]$^+$ |
| Example 79 | 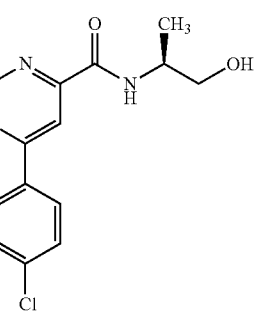<br>6-(4-chlorophenyl)-N-[(2S)-1-hydroxypropan-2-yl]-2-(6-methylpyridin-3-yl)pyrimidine-4-carboxamide<br>LC-MS (method 2): $R_t$ = 0.97 min; MS (ESIpos):<br>m/z = 383 [M + H]$^+$ |
| Example 80 | 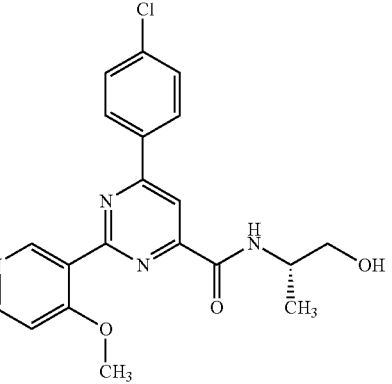<br>6-(4-chlorophenyl)-N-[(2S)-1-hydroxypropan-2-yl]-2-(4-methoxypyridin-3-yl)pyrimidine-4-carboxamide<br>LC-MS (method 2): $R_t$ = 0.78 min; MS (ESIpos):<br>m/z = 399 [M + H]$^+$ |

| Example | Structure<br>IUPAC-Name<br>LC-MS (method): Retention time; Mass found<br>¹H-NMR |
|---|---|
| Example 81 | 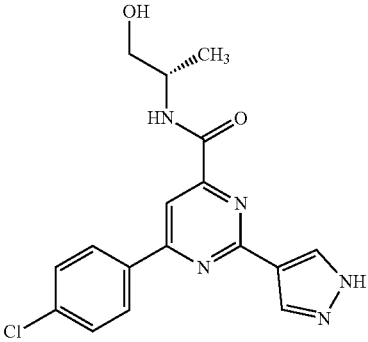 [SMILES: C[C@@H](CO)NC(=O)c1cc(-c2ccc(Cl)cc2)nc(-c2cn[nH]c2)n1]<br>6-(4-chlorophenyl)-N-[(2S)-1-hydroxypropan-2-yl]-2-(1H-pyrazol-4-yl)pyrimidine-4-carboxamide<br>LC-MS (method 2): $R_t$ = 0.99 min; MS (ESIpos):<br>m/z = 358 [M + H]⁺ |
| Example 82 | 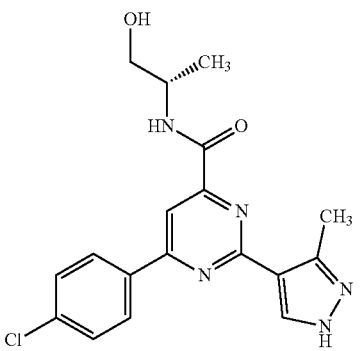 [SMILES: Cc1n[nH]cc1-c1nc(C(=O)N[C@@H](C)CO)cc(-c2ccc(Cl)cc2)n1]<br>6-(4-chlorophenyl)-N-[(2S)-1-hydroxypropan-2-yl]-2-(3-methyl-1H-pyrazol-4-yl)pyrimidine-4-carboxamide<br>LC-MS (method 2): $R_t$ = 1.04 min; MS (ESIpos):<br>m/z = 372 [M + H]⁺ |
| Example 83 | 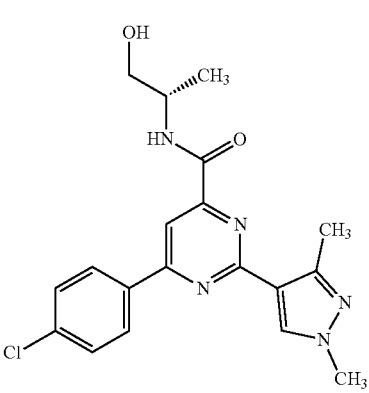 [SMILES: Cc1nn(C)cc1-c1nc(C(=O)N[C@@H](C)CO)cc(-c2ccc(Cl)cc2)n1]<br>6-(4-chlorophenyl)-2-(1,3-dimethyl-1H-pyrazol-4-yl)-N-[(2S)-1-hydroxypropan-2-yl]pyrimidine-4-carboxamide<br>LC-MS (method 2): $R_t$ = 1.13 min; MS (ESIpos):<br>m/z = 386 [M + H]⁺ |
| Example 84 | 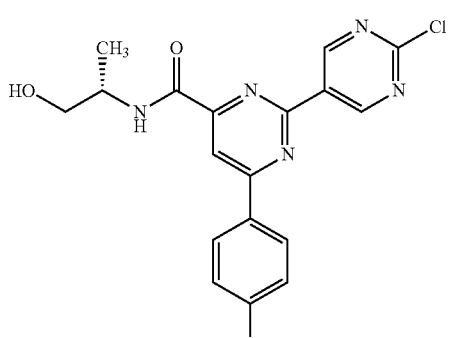<br>2'-chloro-6-(4-chlorophenyl)-N-[(2S)-1-hydroxypropan-2-yl][2,5'-bipyrimidine]-4-carboxamide<br>LC-MS (method 2): $R_t$ = 1.24 min; MS (ESIpos):<br>m/z = 404 [M + H]⁺ |
| Example 85 | 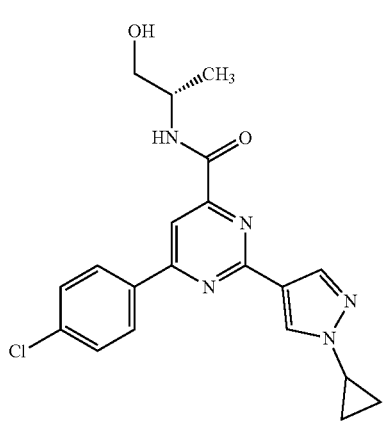 [SMILES: C[C@@H](CO)NC(=O)c1cc(-c2ccc(Cl)cc2)nc(-c2cnn(C3CC3)c2)n1]<br>6-(4-chlorophenyl)-2-(1-cyclopropyl-1H-pyrazol-4-yl)-N-[(2S)-1-hydroxypropan-2-yl]pyrimidine-4-carboxamide<br>LC-MS (method 2): $R_t$ = 1.18 min; MS (ESIpos):<br>m/z = 398 [M + H]⁺ |

Example 86

N-[(trans)-2-hydroxycyclobutyl]-2-(1-methyl-1H-pyrazol-4-yl)-6-[4-(trifluoromethoxy)phenyl]pyrimidine-4-carboxamide

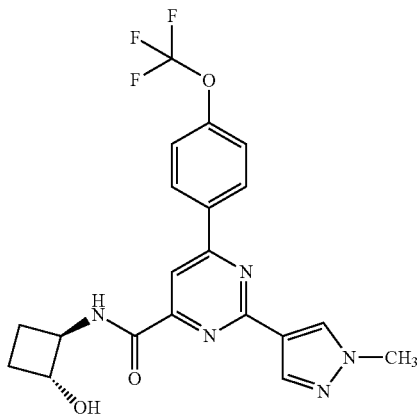 [SMILES: Cn1cc(-c2nc(C(=O)N[C@@H]3CC[C@H]3O)cc(-c3ccc(OC(F)(F)F)cc3)n2)cn1]

To (trans)-2-aminocyclobutan-1-ol (26.1 mg, 300 µmol), a solution of 2-(1-methyl-1H-pyrazol-4-yl)-6-[4-(trifluoromethoxy)phenyl]pyrimidine-4-carboxylic acid (54.6 mg, 150 µmol) in 1 mL of DMF, HATU (171 mg, 450 µmol) in 1 mL of DMF and sodium hydrogen carbonate (75.6 mg, 900 µmol) were added. The reaction was stirred for 3 days at room temperature. The crude mixture was filtered through a pad of Celite and purified by preparative HPLC to give 17.9 mg (93% purity, 26% yield) of the title compound.

LC-MS (method 2): $R_t$=1.18 min; MS (ESIpos): m/z=434 [M+H]$^+$

The following examples were prepared in analogy to example 86:

| Example | Structure<br>IUPAC-Name<br>LC-MS (method): Retention time; Mass found<br>$^1$H-NMR |
|---|---|
| Example 87 | N-[(trans)-2-hydroxycyclopentyl]-2-(1-methyl-1H-pyrazol-4-yl)-6-[4-(trifluoromethoxy)phenyl]pyrimidine-4-carboxamide<br>LC-MS (method 2): $R_t$ = 1.22 min;<br>MS (ESIpos): m/z = 448 [M + H]$^+$ |
| Example 88 | N-[(2S)-1-hydroxy-3,3-dimethylbutan-2-yl]-2-(1-methyl-1H-pyrazol-4-yl)-6-[4-(trifluoromethoxy)phenyl]pyrimidine-4-carboxamide<br>LC-MS (method 2): $R_t$ = 1.31 min;<br>MS (ESIpos): m/z = 464 [M + H]$^+$ |
| Example 89 | 2-(1-methyl-1H-pyrazol-4-yl)-N-[1,1,1-trifluoro-3-hydroxy-2-(hydroxymethyl)propan-2-yl]-6-[4-(trifluoromethoxy)phenyl]pyrimidine-4-carboxamide<br>LC-MS (method 2): $R_t$ = 1.24 min;<br>MS (ESIpos): m/z = 506 [M + H]$^+$ |
| Example 91 | N-[(cis)-2-hydroxycyclopentyl]-2-(1-methyl-1H-pyrazol-4-yl)-6-[4-(trifluoromethoxy)phenyl]pyrimidine-4-carboxamide<br>LC-MS (method 2): $R_t$ = 1.24 min;<br>MS (ESIpos): m/z = 448 [M + H]$^+$ |

| Example | Structure IUPAC-Name LC-MS (method): Retention time; Mass found ¹H-NMR |
|---|---|
| Example 92 | 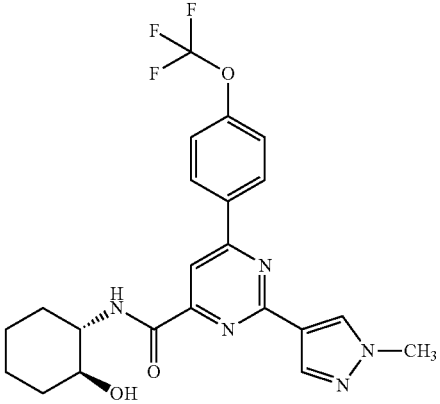 [SMILES: Cn1cc(-c2nc(C(=O)N[C@H]3CCCC[C@@H]3O)cc(-c3ccc(OC(F)(F)F)cc3)n2)cn1]<br>N-[(trans)-2-hydroxycyclohexyl]-2-(1-methyl-1H-pyrazol-4-yl)-6-[4-(trifluoromethoxy)phenyl]pyrimidine-4-carboxamide<br>LC-MS (method 2): $R_t$ = 1.25 min;<br>MS (ESIpos): m/z = 462 [M + H]⁺ |
| Example 93 | 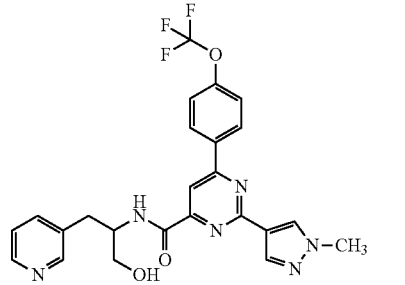 [SMILES: Cn1cc(-c2nc(C(=O)NC(CO)Cc3cccnc3)cc(-c3ccc(OC(F)(F)F)cc3)n2)cn1]<br>N-[1-hydroxy-3-(pyridin-3-yl)propan-2-yl]-2-(1-methyl-1H-pyrazol-4-yl)-6-[4-(trifluoromethoxy)phenyl]pyrimidine-4-carboxamide<br>LC-MS (method 2): $R_t$ = 0.86 min;<br>MS (ESIpos): m/z = 499 [M + H]⁺ |
| Example 94 | 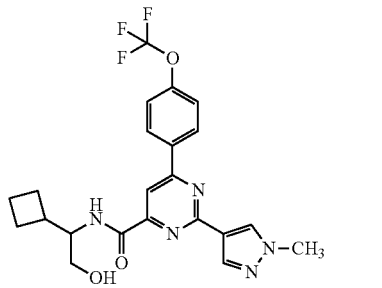 [SMILES: Cn1cc(-c2nc(C(=O)NC(CO)C3CCC3)cc(-c3ccc(OC(F)(F)F)cc3)n2)cn1]<br>N-(1-cyclobutyl-2-hydroxyethyl)-2-(1-methyl-1H-pyrazol-4-yl)-6-[4-(trifluoromethoxy)phenyl]pyrimidine-4-carboxamide<br>LC-MS (method 2): $R_t$ = 1.29 min;<br>MS (ESIpos): m/z = 462 [M + H]⁺ |

| Example | Structure IUPAC-Name LC-MS (method): Retention time; Mass found ¹H-NMR |
|---|---|
| Example 95 | 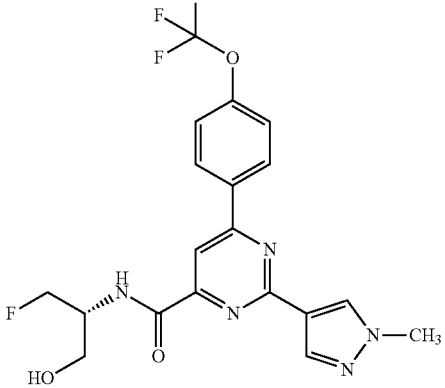<br>N-[(2R)-1-fluoro-3-hydroxypropan-2-yl]-2-(1-methyl-1H-pyrazol-4-yl)-6-[4-(trifluoromethoxy)phenyl]pyrimidine-4-carboxamide<br>LC-MS (method 2): $R_t$ = 1.17 min;<br>MS (ESIpos): m/z = 440 [M + H]⁺ |
| Example 96 | 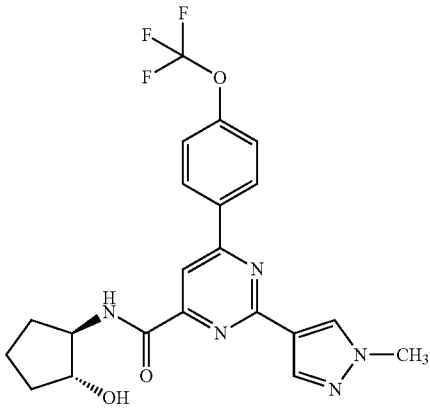 [SMILES: Cn1cc(-c2nc(C(=O)N[C@@H]3CCC[C@H]3O)cc(-c3ccc(OC(F)(F)F)cc3)n2)cn1]<br>N-[(trans)-2-hydroxycyclopentyl]-2-(1-methyl-1H-pyrazol-4-yl)-6-[4-(trifluoromethoxy)phenyl]pyrimidine-4-carboxamide<br>LC-MS (method 2): $R_t$ = 1.22 min;<br>MS (ESIpos): m/z = 448 [M + H]⁺ |
| Example 97 | 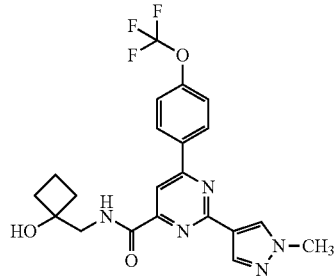 [SMILES: Cn1cc(-c2nc(C(=O)NCC3(O)CCC3)cc(-c3ccc(OC(F)(F)F)cc3)n2)cn1]<br>N-[(1-hydroxycyclobutyl)methyl]-2-(1-methyl-1H-pyrazol-4-yl)-6-[4-(trifluoromethoxy)phenyl]pyrimidine-4-carboxamide<br>LC-MS (method 2): $R_t$ = 1.24 min;<br>MS (ESIpos): m/z = 448 [M + H]⁺ |

| Example | Structure / IUPAC-Name / LC-MS (method): Retention time; Mass found / ¹H-NMR |
|---|---|
| Example 98 | N-[(cis)-4-hydroxy-1,1-dioxo-1lambda⁶-thiolan-3-yl]-2-(1-methyl-1H-pyrazol-4-yl)-6-[4-(trifluoromethoxy)phenyl]pyrimidine-4-carboxamide<br>LC-MS (method 2): $R_t$ = 1.13 min;<br>MS (ESIpos): m/z = 498 [M + H]⁺ |
| Example 99 | N-[(1S)-1-cyclopropyl-2-hydroxyethyl]-2-(1-methyl-1H-pyrazol-4-yl)-6-[4-(trifluoromethoxy)phenyl]pyrimidine-4-carboxamide<br>LC-MS (method 2): $R_t$ = 1.22 min;<br>MS (ESIpos): m/z = 448 [M + H]⁺ |
| Example 100 | N-[(trans)-4-hydroxy-1,1-dioxo-1lambda⁶-thiolan-3-yl]-2-(1-methyl-1H-pyrazol-4-yl)-6-[4-(trifluoromethoxy)phenyl]pyrimidine-4-carboxamide<br>LC-MS (method 2): $R_t$ = 1.13 min;<br>MS (ESIpos): m/z = 498 [M + H]⁺ |
| Example 101 | N-[(1S)-1-cyano-2-hydroxyethyl]-2-(1-methyl-1H-pyrazol-4-yl)-6-[4-(trifluoromethoxy)phenyl]pyrimidine-4-carboxamide<br>LC-MS (method 2): $R_t$ = 1.17 min;<br>MS (ESIpos): m/z = 433 [M + H]⁺ |
| Example 102 | N-[(2S)-3-hydroxy-3-methylbutan-2-yl]-2-(1-methyl-1H-pyrazol-4-yl)-6-[4-(trifluoromethoxy)phenyl]pyrimidine-4-carboxamide<br>LC-MS (method 2): $R_t$ = 1.25 min;<br>MS (ESIpos): m/z = 450 [M + H]⁺ |
| Example 103 | N-[(3S,4S)-4-hydroxytetrahydrofuran-3-yl]-2-(1-methyl-1H-pyrazol-4-yl)-6-[4-(trifluoromethoxy)phenyl]pyrimidine-4-carboxamide<br>LC-MS (method 2): $R_t$ = 1.14 min;<br>MS (ESIpos): m/z = 450 [M + H]⁺ |

| Example | Structure IUPAC-Name LC-MS (method): Retention time; Mass found ¹H-NMR |
|---|---|
| Example 104 | 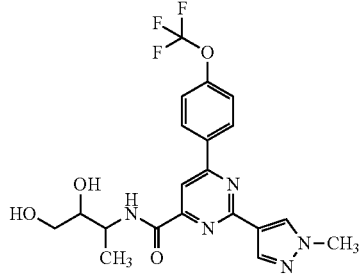 [SMILES: CC(NC(=O)c1cc(-c2ccc(OC(F)(F)F)cc2)nc(-c2cnn(C)c2)n1)C(O)CO]<br>N-(3,4-dihydroxybutan-2-yl)-2-(1-methyl-1H-pyrazol-4-yl)-6-[4-(trifluoromethoxy)phenyl]pyrimidine-4-carboxamide<br>LC-MS (method 2): $R_t$ = 1.11 min;<br>MS (ESIpos): m/z = 452 [M + H]⁺ |
| Example 105 | 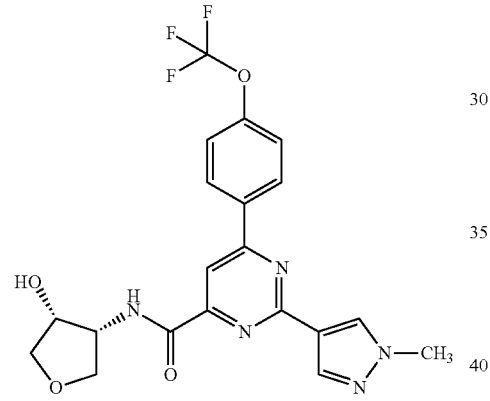<br>N-[(cis)-4-hydroxyoxolan-3-yl]-2-(1-methyl-1H-pyrazol-4-yl)-6-[4-(trifluoromethoxy)phenyl]pyrimidine-4-carboxamide<br>LC-MS (method 2): $R_t$ = 1.14 min;<br>MS (ESIpos): m/z = 450 [M + H]⁺ |
| Example 106 | 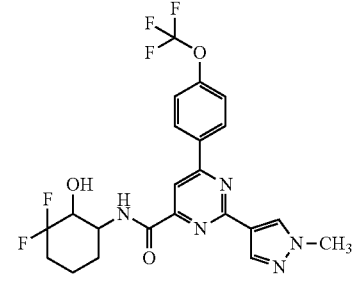 [SMILES: Cn1cc(-c2nc(C(=O)NC3CCCC(F)(F)C3O)cc(-c3ccc(OC(F)(F)F)cc3)n2)cn1]<br>N-(3,3-difluoro-2-hydroxycyclohexyl)-2-(1-methyl-1H-pyrazol-4-yl)-6-[4-(trifluoromethoxy)phenyl]pyrimidine-4-carboxamide<br>LC-MS (method 2): $R_t$ = 1.25 min;<br>MS (ESIpos): m/z = 498 [M + H]⁺ |
| Example 107 | 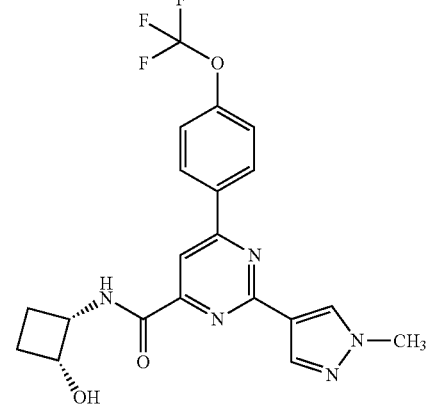<br>N-[(cis)-2-hydroxycyclobutyl]-2-(1-methyl-1H-pyrazol-4-yl)-6-[4-(trifluoromethoxy)phenyl]pyrimidine-4-carboxamide<br>LC-MS (method 2): $R_t$ = 1.20 min;<br>MS (ESIpos): m/z = 434 [M + H]⁺ |
| Example 108 | 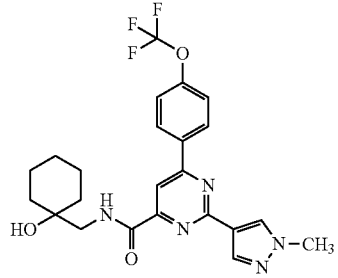 [SMILES: Cn1cc(-c2nc(C(=O)NCC3(O)CCCCC3)cc(-c3ccc(OC(F)(F)F)cc3)n2)cn1]<br>N-[(1-hydroxycyclohexyl)methyl]-2-(1-methyl-1H-pyrazol-4-yl)-6-[4-(trifluoromethoxy)phenyl]pyrimidine-4-carboxamide<br>LC-MS (method 2): $R_t$ = 1.33 min;<br>MS (ESIpos): m/z = 476 [M + H]⁺ |
| Example 109 | 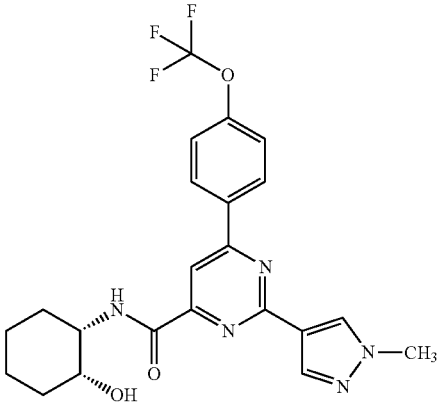 [SMILES: Cn1cc(-c2nc(C(=O)N[C@H]3CCCC[C@H]3O)cc(-c3ccc(OC(F)(F)F)cc3)n2)cn1]<br>N-[(1S,2R)-2-hydroxycyclohexyl]-2-(1-methyl-1H-pyrazol-4-yl)-6-[4-(trifluoromethoxy)phenyl]pyrimidine-4-carboxamide<br>LC-MS (method 2): $R_t$ = 1.29 min;<br>MS (ESIpos): m/z = 462 [M + H]⁺ |

| Example | Structure<br>IUPAC-Name<br>LC-MS (method): Retention time; Mass found<br>¹H-NMR |
|---|---|
| Example 110 | 2-(1-methyl-1H-pyrazol-4-yl)-N-[(2R)-1,1,1-trifluoro-3-hydroxy-3-methylbutan-2-yl]-6-[4-(trifluoromethoxy)phenyl]pyrimidine-4-carboxamide<br>LC-MS (method 2): R$_t$ = 1.34 min;<br>MS (ESIpos): m/z = 504 [M + H]⁺ |
| Example 111 | N-[(3S,4R)-4-hydroxythiolan-3-yl]-2-(1-methyl-1H-pyrazol-4-yl)-6-[4-(trifluoromethoxy)phenyl]pyrimidine-4-carboxamide<br>LC-MS (method 2): R$_t$ = 1.23 min;<br>MS (ESIpos): m/z = 466 [M + H]⁺ |
| Example 112 | 2-(1-methyl-1H-pyrazol-4-yl)-N-[(2R)-1,1,1-trifluoro-3-hydroxypropan-2-yl]-6-[4-(trifluoromethoxy)phenyl]pyrimidine-4-carboxamide<br>LC-MS (method 2): R$_t$ = 1.26 min;<br>MS (ESIpos): m/z = 476 [M + H]⁺ |
| Example 113 | N-[(1S,2R)-2-hydroxycyclohexyl]-2-(1-methyl-1H-pyrazol-4-yl)-6-[4-(trifluoromethoxy)phenyl]pyrimidine-4-carboxamide<br>LC-MS (method 2): R$_t$ = 1.29 min;<br>MS (ESIpos): m/z = 462 [M + H]⁺ |
| Example 114 | 2-(1-methyl-1H-pyrazol-4-yl)-N-[(2S)-3,3,3-trifluoro-2-hydroxypropyl]-6-[4-(trifluoromethoxy)phenyl]pyrimidine-4-carboxamide<br>LC-MS (method 2): R$_t$ = 1.25 min;<br>MS (ESIpos): m/z = 476 [M + H]⁺ |

| Example | Structure<br>IUPAC-Name<br>LC-MS (method): Retention time; Mass found<br>¹H-NMR |
|---|---|
| Example 115 | 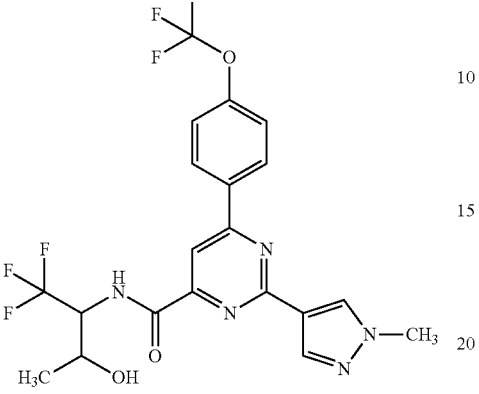<br>2-(1-methyl-1H-pyrazol-4-yl)-N-(1,1,1-trifluoro-3-hydroxybutan-2-yl)-6-[4-(trifluoromethoxy)phenyl]pyrimidine-4-carboxamide<br>LC-MS (method 2): $R_t$ = 1.29 min;<br>MS (ESIpos): m/z = 490 [M + H]⁺ |
| Example 116 | 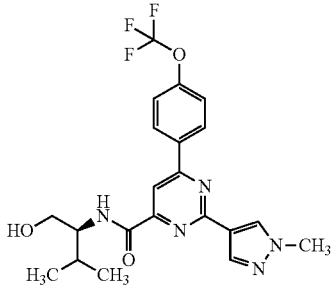 [SMILES: CC(C)[C@@H](CO)NC(=O)c1cc(-c2ccc(OC(F)(F)F)cc2)nc(-c2cnn(C)c2)n1]<br>N-[(2S)-1-hydroxy-3-methylbutan-2-yl]-2-(1-methyl-1H-pyrazol-4-yl)-6-[4-(trifluoromethoxy)phenyl]pyrimidine-4-carboxamide<br>LC-MS (method 2): $R_t$ = 1.26 min;<br>MS (ESIpos): m/z = 450 [M + H]⁺ |

Example 117

N-[(2S)-1-hydroxypropan-2-yl]-2-(pyridin-3-yl)-6-[4-(trifluoromethyl)phenyl]pyrimidine-4-carboxamide

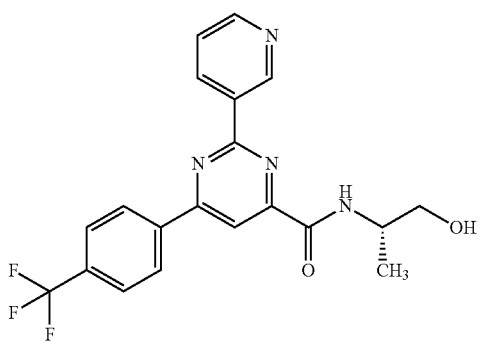 [SMILES: C[C@@H](CO)NC(=O)c1cc(-c2ccc(C(F)(F)F)cc2)nc(-c2cccnc2)n1]

2-(pyridin-3-yl)-6-[4-(trifluoromethyl)phenyl]pyrimidine-4-carboxylic acid (33.0 mg, 95.6 µmol), (2S)-2-aminopropan-1-ol (14.4 mg, 191 µmol), NaHCO₃ (48.2 mg, 573 µmol) and HATU (109 mg, 287 µmol) were stirred in DMF (330 µl) overnight at rt. The crude mixture was purified by preparative HPLC to give 6.0 mg (95% purity, 15% yield) of the title compound LC-MS (method 1): $R_t$=1.20 min; MS (ESIpos): m/z=403 [M+H]⁺

¹H-NMR (400 MHz, DMSO-d6): δ [ppm]=1.25 (d, 3H), 3.46-3.62 (m, 2H), 4.11-4.21 (m, 1H), 4.84-4.98 (m, 1H), 7.64-7.70 (m, 1H), 7.97 (d, 2H), 8.56 (s, 1H), 8.66 (d, 2H), 8.82 (dd, 1H), 8.89 (d, 1H), 9.04 (dt, 1H), 9.92 (d, 1H).

Example 118

N-[(3S,4R)-4-hydroxyoxolan-3-yl]-2-(pyridin-3-yl)-6-[4-(trifluoromethoxy)phenyl]pyrimidine-4-carboxamide

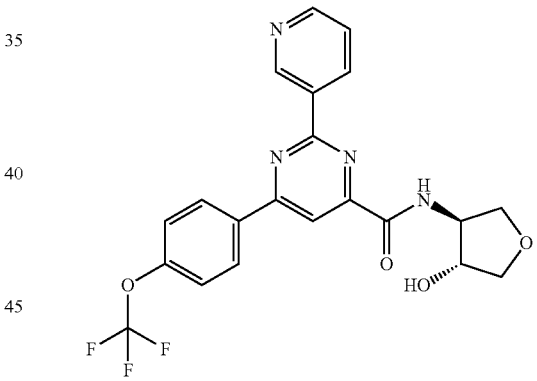

2-(pyridin-3-yl)-6-[4-(trifluoromethoxy)phenyl]pyrimidine-4-carboxylic acid (62.0 mg, 172 µmol), (3R,4S)-4-aminooxolan-3-ol (53.1 mg, 515 µmol), NaHCO₃ (86.5 mg, 1.03 mmol) and HATU (196 mg, 515 µmol) were stirred in DMF (600 µl) overnight at rt. The crude mixture was purified by preparative HPLC to give 40.0 mg (95% purity, 50% yield) of the title compound.

LC-MS (method 2): $R_t$=1.15 min; MS (ESIpos): m/z=447 [M+H]⁺

1H-NMR (400 MHz, DMSO-d6): δ [ppm]=3.59 (dd, 1H), 3.77 (dd, 1H), 4.00 (dd, 1H), 4.07 (dd, 1H), 4.31-4.39 (m, 1H), 4.39-4.45 (m, 1H), 5.40 (d, 1H), 7.60 (d, 2H), 7.65 (ddd, 1H), 8.49 (s, 1H), 8.56-8.62 (m, 2H), 8.80 (dd, 1H), 9.04 (dt, 1H), 9.19 (d, 1H), 9.93 (dd, 1H).

Example 119

6-[4-(difluoromethyl)phenyl]-N-[(2S)-3-hydroxy-3-methylbutan-2-yl]-2-(pyridin-3-yl)pyrimidine-4-carboxamide

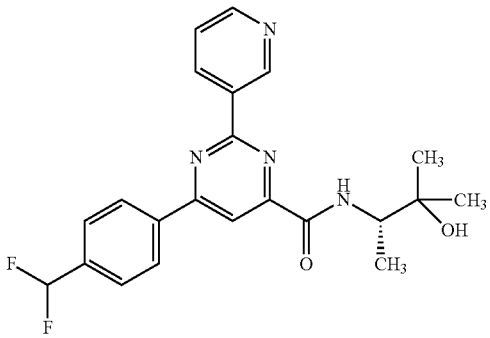 [SMILES: C[C@H](NC(=O)c1cc(-c2ccc(C(F)F)cc2)nc(-c2cccnc2)n1)C(C)(C)O]

6-[4-(difluoromethyl)phenyl]-2-(pyridin-3-yl)pyrimidine-4-carboxylic acid (143 mg, 437 µmol), (3S)-3-amino-2-methylbutan-2-ol hydrogen chloride (1/1) (122 mg, 874 µmol), NaHCO$_3$ (220 mg, 2.62 mmol) and HATU (498 mg, 1.31 mmol) were stirred in DMF (1.5 ml) overnight at rt. The crude mixture was purified by preparative HPLC to give 115 mg (95% purity, 61% yield) of the title compound.

LC-MS (method 1): R$_t$=1.14 min; MS (ESIpos): m/z=413 [M+H]$^+$ $^1$H-NMR (400 MHz, DMSO-d6): δ [ppm]=1.19 (d, 6H), 1.23 (d, 3H), 4.03 (dq, 1H), 4.81 (s, 1H), 7.02-7.34 (m, 1H), 7.67 (ddd, 1H), 7.81 (d, 2H), 8.53 (s, 1H), 8.59 (d, 2H), 8.64 (d, 1H), 8.81 (dd, 1H), 8.93 (dt, 1H), 9.78-9.81 (m, 1H).

Example 120

6-[4-(difluoromethyl)phenyl]-N-(2-hydroxy-2-methylpropyl)-2-(pyridin-3-yl)pyrimidine-4-carboxamide

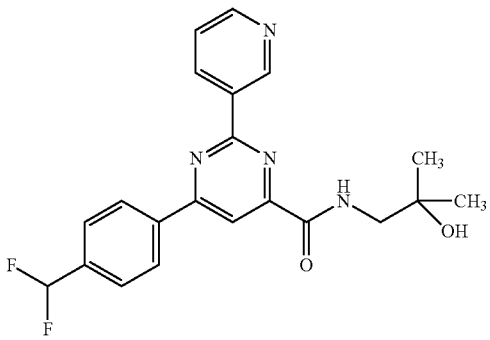 [SMILES: CC(C)(O)CNC(=O)c1cc(-c2ccc(C(F)F)cc2)nc(-c2cccnc2)n1]

6-[4-(difluoromethyl)phenyl]-2-(pyridin-3-yl)pyrimidine-4-carboxylic acid (143 mg, 437 µmol), 1-amino-2-methylpropan-2-ol (77.9 mg, 874 µmol), NaHCO$_3$ (220 mg, 2.62 mmol) and HATU (498 mg, 1.31 mmol) were stirred in DMF (1.5 ml) overnight at rt. The crude material was purified by preparative HPLC to give 104 mg (98% purity, 59% yield) of the title compound LC-MS (method 1): R$_t$=1.09 min; MS (ESIpos): m/z=399 [M+H]$^+$ $^1$H-NMR (400 MHz, DMSO-d6): δ [ppm]=1.17 (s, 6H), 3.39 (d, 2H), 4.78 (s, 1H), 7.02-7.33 (m, 1H), 7.66 (ddd, 1H), 7.80 (d, 2H), 8.53 (s, 1H), 8.58 (d, 2H), 8.80 (dd, 1H), 8.98 (dt, 1H), 9.02 (t, 1H), 9.82-9.87 (m, 1H).

EXPERIMENTAL SECTION—BIOLOGICAL ASSAYS

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

Transactivation Assay in Human Cell Line (In Vitro Assay 1)

Transactivation assay was carried out in U87 glioblastoma cells (ATCC) endogenously expressing AHR. In addition the cells were stably transfected with an AHR inducible firefly luciferase reporter gene construct that carried AHR-binding sites (DRE) in its promoter and a renilla reporter gene construct with constitutively active promoter. Kynurenic acid is an endogenous AHR activating ligand and was used to prestimulate test cells prior to testing the antagonistic properties of compounds.

In Vitro Assay 1: Antagonism in Human Cell Line

Cells in medium (tryptophan free RPMI (PAN-Biotech #P04-17598), 1% FCS (Biochrome Superior #S0615), 1× Penicillin/Streptomycin (Sigma P0781) supplemented with 150 µM kynurenic acid were grown for 20 hours in absence (negative control) or presence of increasing concentrations of test compounds (typical dilutions: 72 pmol/L, 0.25 nmol/L, 0.89 nmol/L; 3.1 nmol/L, 11 nmol/L, 38 nmol/L, 130 nmol/L, 470 nmol/L, 1.6 µmol/L, 5.7 µmol/L and 20 µmol/L in duplicates). As positive inhibition control cells supplemented with 150 µM kynurenic acid were incubated in presence of 5 µM Staurosporin. Normalization was done by positive and negative controls.

Firefly luciferase and Renilla activity was determined by the DualGlo Luciferase Assay System (Promega, #2920). Renilla activity was used to assess toxic effects of compounds.

Transactivation Assay in Mouse Cell Line (In Vitro Assay 2)

Transactivation assay was carried out in Hepa 1c1c7 cells (ATCC #CRL-2026) endogenously expressing AHR. In addition the cells were stably transfected with an AHR inducible firefly luciferase reporter gene construct that carried AHR-binding sites (DRE) in its promoter. Kynurenic acid is an endogenous AHR activating ligand and was used to prestimulate test cells prior to testing the antagonistic properties of compounds.

In Vitro Assay 2: Antagonism in Mouse Cell Line

Cells in medium (tryptophan free RPMI (PAN-Biotech #P04-17598), 1% FCS (Biochrome Superior #S0615), 1× Penicillin/Streptomycin (Sigma P0781) supplemented with 200 μM kynurenic acid (Sigma #K3375) were grown for 20 hours in absence (negative control) or presence of increasing concentrations of test compounds (typical dilutions: 72 pmol/L, 0.25 nmol/L, 0.89 nmol/L; 3.1 nmol/L, 11 nmol/L, 38 nmol/L, 130 nmol/L, 470 nmol/L, 1.6 μmol/L, 5.7 μmol/L and 20 μmol/L in duplicates). As positive inhibition control cells without addition of kynurenic acid were incubated. Normalization was done by positive and negative controls.

Firefly luciferase activity was determined by the Steady-Glo Luciferase Assay System (Promega, #E2550).

TABLE 2

IC$_{50}$ values of examples in in vitro assays 1 and 2

| Example No | Assay 1: Human AhR Antagonism IC$_{50}$ [M] | Assay 2: Mouse AhR Antagonism IC$_{50}$ [M] |
|---|---|---|
| 1 | 8.85E−10 | 2.03E−09 |
| 2 | 2.88E−09 | 2.03E−08 |
| 3 | 3.86E−09 | 7.81E−09 |
| 4 | | |
| 5 | 3.68E−09 | 2.92E−09 |
| 6 | 7.53E−09 | 1.50E−08 |
| 7 | | 1.27E−08 |
| 8 | 2.57E−09 | 7.19E−09 |
| 9 | 1.10E−09 | 2.84E−09 |
| 10 | 1.38E−09 | 8.42E−09 |
| 11 | 3.93E−09 | 7.94E−09 |
| 12 | 7.34E−08 | 2.06E−07 |
| 13 | 1.43E−08 | 5.81E−08 |
| 14 | 3.07E−07 | |
| 15 | | |
| 16 | | |
| 17 | | |
| 18 | | |
| 19 | | |
| 20 | 7.17E−07 | 3.54E−07 |
| 21 | 3.79E−07 | 2.13E−06 |
| 22 | 1.10E−06 | 5.53E−06 |
| 23 | >2.00E−5 | |
| 24 | 2.08E−07 | 3.59E−07 |
| 25 | 8.05E−09 | 1.10E−07 |
| 26 | 3.96E−06 | |
| 27 | 4.38E−07 | |
| 28 | 1.67E−07 | 2.29E−07 |
| 29 | 1.52E−08 | |
| 30 | 6.38E−09 | |
| 31 | 1.45E−08 | |
| 32 | 4.62E−08 | 3.88E−08 |
| 33 | 9.25E−09 | |
| 34 | 2.96E−08 | 2.40E−08 |
| 35 | 1.03E−06 | 5.31E−06 |
| 36 | 5.22E−06 | 1.00E−05 |
| 37 | 7.17E−08 | 9.30E−08 |
| 38 | 4.51E−06 | |
| 39 | 6.84E−08 | 4.31E−07 |
| 40 | 4.24E−09 | 4.26E−08 |
| 41 | 9.76E−08 | 5.58E−08 |
| 42 | 1.20E−07 | |
| 43 | 2.52E−08 | 2.71E−07 |
| 44 | 9.72E−07 | |
| 45 | 5.72E−08 | |
| 46 | 4.31E−07 | |
| 47 | 3.17E−07 | 9.61E−07 |
| 48 | | |
| 49 | | |
| 50 | 5.91E−09 | |
| 51 | | |
| 52 | | |
| 53 | | |
| 54 | 3.66E−08 | 4.11E−08 |
| 55 | 1.03E−08 | 1.73E−08 |
| 56 | 9.65E−07 | |
| 57 | | |
| 58 | 3.28E−07 | |
| 59 | 6.87E−06 | |
| 60 | 6.47E−08 | 1.42E−06 |
| 61 | | 4.80E−09 |
| 62 | | |
| 63 | | |
| 64 | | |
| 65 | 3.55E−07 | |
| 66 | 5.01E−08 | |
| 67 | 1.26E−05 | |
| 68 | 7.24E−06 | 9.83E−06 |
| 69 | 3.42E−07 | |
| 70 | 9.42E−08 | 2.95E−07 |
| 71 | 3.23E−09 | 4.71E−09 |
| 72 | 3.26E−08 | 9.82E−08 |
| 73 | 1.63E−08 | 2.88E−08 |
| 74 | 3.36E−08 | 6.29E−08 |
| 75 | 6.37E−09 | 2.12E−08 |
| 76 | | |
| 77 | 1.18E−06 | |
| 78 | 7.41E−07 | |
| 79 | 1.08E−07 | 6.71E−07 |
| 80 | 2.64E−09 | 3.08E−08 |
| 81 | 1.04E−06 | |
| 82 | 2.15E−07 | |
| 83 | 5.42E−08 | 1.51E−06 |
| 84 | 1.76E−05 | |
| 85 | 1.20E−06 | 7.40E−06 |
| 86 | 5.74E−09 | 7.07E−09 |
| 87 | 5.33E−09 | 3.93E−09 |
| 88 | 2.04E−08 | 8.19E−09 |
| 89 | 7.95E−09 | 4.34E−09 |
| 91 | 1.58E−09 | |
| 92 | 4.27E−09 | 5.79E−09 |
| 93 | 3.41E−08 | 1.65E−08 |
| 94 | 5.44E−09 | 2.43E−08 |
| 95 | 3.48E−09 | 4.00E−09 |
| 96 | 5.32E−08 | 5.61E−08 |
| 97 | 4.99E−09 | |
| 98 | 2.06E−08 | |
| 99 | 1.76E−08 | 2.15E−08 |
| 100 | 1.01E−08 | 8.18E−09 |
| 101 | 2.23E−08 | 1.89E−08 |
| 102 | 6.86E−09 | 3.26E−09 |
| 103 | 6.74E−09 | 5.82E−09 |
| 104 | 1.25E−08 | 2.04E−08 |
| 105 | 8.48E−09 | 6.01E−09 |
| 106 | 7.32E−09 | 2.00E−08 |
| 107 | 4.57E−09 | |
| 108 | | |
| 109 | | |
| 110 | | |
| 111 | | |
| 112 | | |
| 113 | | |
| 114 | | |
| 115 | | |
| 117 | 1.26E−09 | 1.33E−09 |
| 116 | | 1.97E−09 |
| 118 | 2.34E−09 | 3.40E−09 |
| 119 | 2.88E−09 | 6.81E−09 |
| 120 | | 1.02E−08 |

The invention claimed is:
1. A compound of formula (I):

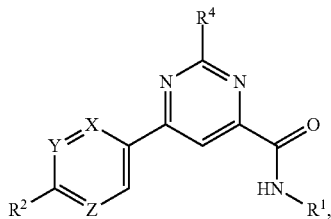

wherein
X is CH;
Y is CR³;
Z is CH;
R¹ is C₂-C₆-hydroxyalkyl, wherein said C₂-C₆-hydroxyalkyl groups are optionally substituted once with R⁷ and optionally one to three times with fluoro, or C₄-C₆-cycloalkyl substituted once with hydroxy and optionally one to two times with fluoro, or (C₄-C₆-cycloalkyl substituted once with hydroxy)-methyl, or 4-hydroxyoxolan-3-yl, 4-hydroxythiolan-3-yl or 4-hydroxy-1,1-dioxo-1lambda⁶-thiolan-3-yl;
R² is chloro, difluoromethyl, trifluoromethyl, or trifluoromethoxy;
R³ is hydrogen;
R⁴ is a group selected from the group consisting of

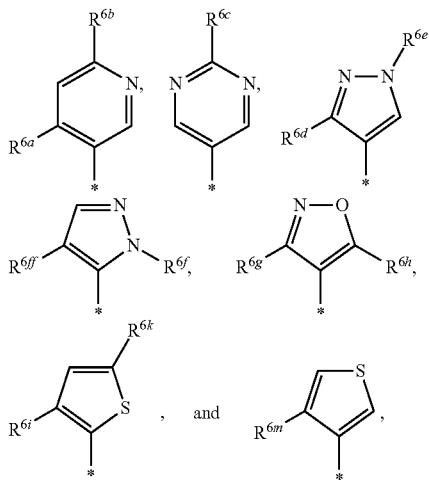

wherein * indicates the point of attachment of said group with the rest of the molecule;
R⁶ᵃ is hydrogen or methoxy;
R⁶ᵇ is hydrogen, methyl, methoxy, or cyano;
R⁶ᶜ is hydrogen, chloro, methyl, or cyano;
R⁶ᵈ is hydrogen or methyl;
R⁶ᵉ is hydrogen, methyl, isobutyl, or cyclopropyl;
R⁶ᶠ is hydrogen or methyl;
R⁶ᶠᶠ is hydrogen or methyl;
R⁶ᵍ is hydrogen or methyl;
R⁶ʰ is hydrogen or methyl;
R⁶ⁱ is hydrogen or methyl;
R⁶ᵏ is hydrogen, chloro, or cyano;
R⁶ᵐ is hydrogen or methyl;
R⁷ is cyano, C₃-C₄-cycloalkyl, or pyridinyl; or a polymorph, an enantiomer, a diastereomer, a racemate, a tautomer, an N-oxide, a hydrate, or a solvate, a physiologically acceptable salt, or a solvate of a physiologically acceptable salt thereof.

2. The compound according to claim 1 which is selected from the group consisting of
N-[(2S)-1-hydroxypropan-2-yl]-2-(pyridin-3-yl)-6-[4-(trifluoromethoxy)phenyl]pyrimidine-4-carboxamide;
N-[(2R)-1-hydroxypropan-2-yl]-2-(pyridin-3-yl)-6-[4-(trifluoromethoxy)phenyl]pyrimidine-4-carboxamide;
N-(2-hydroxy-2-methylpropyl)-2-(pyridin-3-yl)-6-[4-(trifluoromethoxy)phenyl]pyrimidine-4-carboxamide;
2-(pyridin-3-yl)-N-[(2S)-3,3,3-trifluoro-2-hydroxypropyl]-6-[4-(trifluoromethoxy)phenyl]pyrimidine-4-carboxamide;
N-[(2S)-1-hydroxypropan-2-yl]-2-(1-methyl-1H-pyrazol-4-yl)-6-[4-(trifluoromethoxy)phenyl]pyrimidine-4-carboxamide;
N-(2-hydroxy-2-methylpropyl)-2-(1-methyl-1H-pyrazol-4-yl)-6-[4-(trifluoromethoxy)phenyl]pyrimidine-4-carboxamide;
N-(2-hydroxy-2-methylpropyl)-2-(pyridin-3-yl)-6-[4-(trifluoromethyl)phenyl]pyrimidine-4-carboxamide;
N-(2-hydroxy-2-methylpropyl)-2-(1-methyl-1H-pyrazol-4-yl)-6-[4-(trifluoromethyl)phenyl]pyrimidine-4-carboxamide;
6-(4-chlorophenyl)-N-[(2S)-1-hydroxypropan-2-yl]-2-(pyridin-3-yl)pyrimidine-4-carboxamide;
6-(4-chlorophenyl)-N-(2-hydroxy-2-methylpropyl)-2-(pyridin-3-yl)pyrimidine-4-carboxamide;
6-(4-chlorophenyl)-N-[(2S)-1-hydroxypropan-2-yl]-2-(1-methyl-1H-pyrazol-4-yl)pyrimidine-4-carboxamide;
6-(4-chlorophenyl)-N-[(2R)-1-hydroxypropan-2-yl]-2-(1-methyl-1H-pyrazol-4-yl)pyrimidine-4-carboxamide;
6-(4-chlorophenyl)-N-(2-hydroxy-2-methylpropyl)-2-(1-methyl-1H-pyrazol-4-yl)pyrimidine-4-carboxamide;
N-(2-hydroxy-2-methylpropyl)-2-(6-methoxypyridin-3-yl)-6-[4-(trifluoromethoxy)phenyl]pyrimidine-4-carboxamide;
N-(2-hydroxy-2-methylpropyl)-2-(thiophen-2-yl)-6-[4-(trifluoromethoxy)phenyl]pyrimidine-4-carboxamide;
N-(2-hydroxy-2-methylpropyl)-2-(4-methylthiophen-3-yl)-6-[4-(trifluoromethoxy)phenyl]pyrimidine-4-carboxamide;
N-(2-hydroxy-2-methylpropyl)-2-(thiophen-3-yl)-6-[4-(trifluoromethoxy)phenyl]pyrimidine-4-carboxamide;
2-(5-chlorothiophen-2-yl)-N-(2-hydroxy-2-methylpropyl)-6-[4-(trifluoromethoxy)phenyl]pyrimidine-4-carboxamide;
N-(2-hydroxy-2-methylpropyl)-2-(3-methylthiophen-2-yl)-6-[4-(trifluoromethoxy)phenyl]pyrimidine-4-carboxamide;
N-(2-hydroxy-2-methylpropyl)-2-(1H-pyrazol-4-yl)-6-[4-(trifluoromethoxy)phenyl]pyrimidine-4-carboxamide;
N-(2-hydroxy-2-methylpropyl)-2'-methyl-6-[4-(trifluoromethoxy)phenyl][2,5'-bipyrimidine]-4-carboxamide;
N-(2-hydroxy-2-methylpropyl)-2-(1,2-oxazol-4-yl)-6-[4-(trifluoromethoxy)phenyl]pyrimidine-4-carboxamide;
2'-cyano-N-(2-hydroxy-2-methylpropyl)-6-[4-(trifluoromethoxy)phenyl][2,5'-bipyrimidine]-4-carboxamide;
N-(2-hydroxy-2-methylpropyl)-2-(3-methyl-1H-pyrazol-4-yl)-6-[4-(trifluoromethoxy)phenyl]pyrimidine-4-carboxamide;

2-(1,3-dimethyl-1H-pyrazol-4-yl)-N-(2-hydroxy-2-methylpropyl)-6-[4-(trifluoromethoxy)phenyl]pyrimidine-4-carboxamide;
2-(1-cyclopropyl-1H-pyrazol-4-yl)-N-(2-hydroxy-2-methylpropyl)-6-[4-(trifluoromethoxy)phenyl]pyrimidine-4-carboxamide;
N-[(2S)-1-hydroxypropan-2-yl]-2-(6-methoxypyridin-3-yl)-6-[4-(trifluoromethoxy)phenyl]pyrimidine-4-carboxamide;
2-(5-cyanothiophen-2-yl)-N-[(2S)-1-hydroxypropan-2-yl]-6-[4-(trifluoromethoxy)phenyl]pyrimidine-4-carboxamide;
N-[(2S)-1-hydroxypropan-2-yl]-2-(4-methylthiophen-3-yl)-6-[4-(trifluoromethoxy)phenyl]pyrimidine-4-carboxamide;
N-[(2S)-1-hydroxypropan-2-yl]-2-(thiophen-2-yl)-6-[4-(trifluoromethoxy)phenyl]pyrimidine-4-carboxamide;
N-[(2S)-1-hydroxypropan-2-yl]-2-(thiophen-3-yl)-6-[4-(trifluoromethoxy)phenyl]pyrimidine-4-carboxamide;
2-(5-chlorothiophen-2-yl)-N-[(2S)-1-hydroxypropan-2-yl]-6-[4-(trifluoromethoxy)phenyl]pyrimidine-4-carboxamide;
N-[(2S)-1-hydroxypropan-2-yl]-2-(3-methylthiophen-2-yl)-6-[4-(trifluoromethoxy)phenyl]pyrimidine-4-carboxamide;
N-[(2S)-1-hydroxypropan-2-yl]-2-(1-methyl-1H-pyrazol-5-yl)-6-[4-(trifluoromethoxy)phenyl]pyrimidine-4-carboxamide;
2-(3,5-dimethyl-1,2-oxazol-4-yl)-N-[(2S)-1-hydroxypropan-2-yl]-6-[4-(trifluoromethoxy)phenyl]pyrimidine-4-carboxamide;
N-[(2S)-1-hydroxypropan-2-yl]-2-[1-(2-methylpropyl)-1H-pyrazol-4-yl]-6-[4-(trifluoromethoxy)phenyl]pyrimidine-4-carboxamide;
N-[(2S)-1-hydroxypropan-2-yl]-2-(1H-pyrazol-3-yl)-6-[4-(trifluoromethoxy)phenyl]pyrimidine-4-carboxamide;
2-(6-cyanopyridin-3-yl)-N-[(2S)-1-hydroxypropan-2-yl]-6-[4-(trifluoromethoxy)phenyl]pyrimidine-4-carboxamide;
N-[(2S)-1-hydroxypropan-2-yl]-2-(6-methylpyridin-3-yl)-6-[4-(trifluoromethoxy)phenyl]pyrimidine-4-carboxamide;
N-[(2S)-1-hydroxypropan-2-yl]-2-(4-methoxypyridin-3-yl)-6-[4-(trifluoromethoxy)phenyl]pyrimidine-4-carboxamide;
N-[(2S)-1-hydroxypropan-2-yl]-2-(1H-pyrazol-4-yl)-6-[4-(trifluoromethoxy)phenyl]pyrimidine-4-carboxamide;
N-[(2S)-1-hydroxypropan-2-yl]-2'-methyl-6-[4-(trifluoromethoxy)phenyl][2,5'-bipyrimidine]-4-carboxamide;
2-(1,3-dimethyl-1H-pyrazol-4-yl)-N-[(2S)-1-hydroxypropan-2-yl]-6-[4-(trifluoromethoxy)phenyl]pyrimidine-4-carboxamide;
2-(1-cyclopropyl-1H-pyrazol-4-yl)-N-[(2S)-1-hydroxypropan-2-yl]-6-[4-(trifluoromethoxy)phenyl]pyrimidine-4-carboxamide;
N-[(2S)-1-hydroxypropan-2-yl]-2-(4-methyl-1H-pyrazol-5-yl)-6-[4-(trifluoromethoxy)phenyl]pyrimidine-4-carboxamide;
6-(4-chlorophenyl)-N-(2-hydroxy-2-methylpropyl)-2-(6-methoxypyridin-3-yl)pyrimidine-4-carboxamide;
6-(4-chlorophenyl)-2-(5-cyanothiophen-2-yl)-N-(2-hydroxy-2-methylpropyl)pyrimidine-4-carboxamide;
6-(4-chlorophenyl)-N-(2-hydroxy-2-methylpropyl)-2-(4-methylthiophen-3-yl)pyrimidine-4-carboxamide;
6-(4-chlorophenyl)-N-(2-hydroxy-2-methylpropyl)-2-(thiophen-2-yl)pyrimidine-4-carboxamide;
6-(4-chlorophenyl)-N-[(2S)-1-hydroxypropan-2-yl]-2-(thiophen-2-yl)pyrimidine-4-carboxamide;
6-(4-chlorophenyl)-N-(2-hydroxy-2-methylpropyl)-2-(thiophen-3-yl)pyrimidine-4-carboxamide;
6-(4-chlorophenyl)-2-(5-chlorothiophen-2-yl)-N-(2-hydroxy-2-methylpropyl)pyrimidine-4-carboxamide;
6-(4-chlorophenyl)-N-(2-hydroxy-2-methylpropyl)-2-(3-methylthiophen-2-yl)pyrimidine-4-carboxamide;
6-(4-chlorophenyl)-N-(2-hydroxy-2-methylpropyl)-2-(1-methyl-1H-pyrazol-5-yl)pyrimidine-4-carboxamide;
6-(4-chlorophenyl)-N-(2-hydroxy-2-methylpropyl)[2,5'-bipyrimidine]-4-carboxamide;
6-(4-chlorophenyl)-2-(3,5-dimethyl-1,2-oxazol-4-yl)-N-(2-hydroxy-2-methylpropyl)pyrimidine-4-carboxamide;
6-(4-chlorophenyl)-N-(2-hydroxy-2-methylpropyl)-2-[1-(2-methylpropyl)-1H-pyrazol-4-yl]pyrimidine-4-carboxamide;
6-(4-chlorophenyl)-N-(2-hydroxy-2-methylpropyl)-2-(1H-pyrazol-3-yl)pyrimidine-4-carboxamide;
6-(4-chlorophenyl)-2-(6-cyanopyridin-3-yl)-N-(2-hydroxy-2-methylpropyl)pyrimidine-4-carboxamide;
6-(4-chlorophenyl)-N-(2-hydroxy-2-methylpropyl)-2-(6-methylpyridin-3-yl)pyrimidine-4-carboxamide;
6-(4-chlorophenyl)-N-(2-hydroxy-2-methylpropyl)-2-(4-methoxypyridin-3-yl)pyrimidine-4-carboxamide;
6-(4-chlorophenyl)-N-(2-hydroxy-2-methylpropyl)-2-(1H-pyrazol-4-yl)pyrimidine-4-carboxamide;
6-(4-chlorophenyl)-N-(2-hydroxy-2-methylpropyl)-2'-methyl[2,5'-bipyrimidine]-4-carboxamide;
6-(4-chlorophenyl)-2'-cyano-N-(2-hydroxy-2-methylpropyl)[2,5'-bipyrimidine]-4-carboxamide;
6-(4-chlorophenyl)-N-(2-hydroxy-2-methylpropyl)-2-(3-methyl-1H-pyrazol-4-yl)pyrimidine-4-carboxamide;
6-(4-chlorophenyl)-2-(1,3-dimethyl-1H-pyrazol-4-yl)-N-(2-hydroxy-2-methylpropyl)pyrimidine-4-carboxamide;
2'-chloro-6-(4-chlorophenyl)-N-(2-hydroxy-2-methylpropyl)[2,5'-bipyrimidine]-4-carboxamide;
6-(4-chlorophenyl)-2-(1-cyclopropyl-1H-pyrazol-4-yl)-N-(2-hydroxy-2-methylpropyl)pyrimidine-4-carboxamide;
6-(4-chlorophenyl)-N-[(2S)-1-hydroxypropan-2-yl]-2-(6-methoxypyridin-3-yl)pyrimidine-4-carboxamide;
6-(4-chlorophenyl)-2-(5-cyanothiophen-2-yl)-N-[(2S)-1-hydroxypropan-2-yl]pyrimidine-4-carboxamide;
6-(4-chlorophenyl)-N-[(2S)-1-hydroxypropan-2-yl]-2-(4-methylthiophen-3-yl)pyrimidine-4-carboxamide;
6-(4-chlorophenyl)-2-(5-chlorothiophen-2-yl)-N-[(2S)-1-hydroxypropan-2-yl]pyrimidine-4-carboxamide;
6-(4-chlorophenyl)-N-[(2S)-1-hydroxypropan-2-yl]-2-(3-methylthiophen-2-yl)pyrimidine-4-carboxamide;
6-(4-chlorophenyl)-N-[(2S)-1-hydroxypropan-2-yl]-2-(1-methyl-1H-pyrazol-5-yl)pyrimidine-4-carboxamide;
6-(4-chlorophenyl)-N-[(2S)-1-hydroxypropan-2-yl][2,5'-bipyrimidine]-4-carboxamide;
6-(4-chlorophenyl)-2-(3,5-dimethyl-1,2-oxazol-4-yl)-N-[(2S)-1-hydroxypropan-2-yl]pyrimidine-4-carboxamide;
6-(4-chlorophenyl)-N-[(2S)-1-hydroxypropan-2-yl]-2-[1-(2-methylpropyl)-1H-pyrazol-4-yl]pyrimidine-4-carboxamide;
6-(4-chlorophenyl)-2-(6-cyanopyridin-3-yl)-N-[(2S)-1-hydroxypropan-2-yl]pyrimidine-4-carboxamide;

6-(4-chlorophenyl)-N-[(2S)-1-hydroxypropan-2-yl]-2-(6-methylpyridin-3-yl)pyrimidine-4-carboxamide;
6-(4-chlorophenyl)-N-[(2S)-1-hydroxypropan-2-yl]-2-(4-methoxypyridin-3-yl)pyrimidine-4-carboxamide;
6-(4-chlorophenyl)-N-[(2S)-1-hydroxypropan-2-yl]-2-(1H-pyrazol-4-yl)pyrimidine-4-carboxamide;
6-(4-chlorophenyl)-N-[(2S)-1-hydroxypropan-2-yl]-2-(3-methyl-1H-pyrazol-4-yl)pyrimidine-4-carboxamide;
6-(4-chlorophenyl)-2-(1,3-dimethyl-1H-pyrazol-4-yl)-N-[(2S)-1-hydroxypropan-2-yl]pyrimidine-4-carboxamide;
2'-chloro-6-(4-chlorophenyl)-N-[(2S)-1-hydroxypropan-2-yl][2,5'-bipyrimidine]-4-carboxamide;
6-(4-chlorophenyl)-2-(1-cyclopropyl-1H-pyrazol-4-yl)-N-[(2S)-1-hydroxypropan-2-yl]pyrimidine-4-carboxamide;
N-[(1R,2R)-2-hydroxycyclobutyl]-2-(1-methyl-1H-pyrazol-4-yl)-6-[4-(trifluoromethoxy)phenyl]pyrimidine-4-carboxamide;
N-[(1S,2S)-2-hydroxycyclopentyl]-2-(1-methyl-1H-pyrazol-4-yl)-6-[4-(trifluoromethoxy)phenyl]pyrimidine-4-carboxamide;
N-[(2S)-1-hydroxy-3,3-dimethylbutan-2-yl]-2-(1-methyl-1H-pyrazol-4-yl)-6-[4-(trifluoromethoxy)phenyl]pyrimidine-4-carboxamide;
2-(1-methyl-1H-pyrazol-4-yl)-N-[1,1,1-trifluoro-3-hydroxy-2-(hydroxymethyl)propan-2-yl]-6-[4-(trifluoromethoxy)phenyl]pyrimidine-4-carboxamide;
N-[(1S,2R)-2-hydroxycyclopentyl]-2-(1-methyl-1H-pyrazol-4-yl)-6-[4-(trifluoromethoxy)phenyl]pyrimidine-4-carboxamide;
N-[(1S,2S)-2-hydroxycyclohexyl]-2-(1-methyl-1H-pyrazol-4-yl)-6-[4-(trifluoromethoxy)phenyl]pyrimidine-4-carboxamide;
N-[1-hydroxy-3-(pyridin-3-yl)propan-2-yl]-2-(1-methyl-1H-pyrazol-4-yl)-6-[4-(trifluoromethoxy)phenyl]pyrimidine-4-carboxamide;
N-(1-cyclobutyl-2-hydroxyethyl)-2-(1-methyl-1H-pyrazol-4-yl)-6-[4-(trifluoromethoxy)phenyl]pyrimidine-4-carboxamide;
N-[(2R)-1-fluoro-3-hydroxypropan-2-yl]-2-(1-methyl-1H-pyrazol-4-yl)-6-[4-(trifluoromethoxy)phenyl]pyrimidine-4-carboxamide;
N-[(1R,2R)-2-hydroxycyclopentyl]-2-(1-methyl-1H-pyrazol-4-yl)-6-[4-(trifluoromethoxy)phenyl]pyrimidine-4-carboxamide;
N-[(1-hydroxycyclobutyl)methyl]-2-(1-methyl-1H-pyrazol-4-yl)-6-[4-(trifluoromethoxy)phenyl]pyrimidine-4-carboxamide;
N-[(3R,4S)-4-hydroxy-1,1-dioxo-1 lambda⁶-thiolan-3-yl]-2-(1-methyl-1H-pyrazol-4-yl)-6-[4-(trifluoromethoxy)phenyl]pyrimidine-4-carboxamide;
N-[(1S)-1-cyclopropyl-2-hydroxyethyl]-2-(1-methyl-1H-pyrazol-4-yl)-6-[4-(trifluoromethoxy)phenyl]pyrimidine-4-carboxamide;
N-[(3R,4R)-4-hydroxy-1,1-dioxo-1 lambda⁶-thiolan-3-yl]-2-(1-methyl-1H-pyrazol-4-yl)-6-[4-(trifluoromethoxy)phenyl]pyrimidine-4-carboxamide;
N-[(1S)-1-cyano-2-hydroxyethyl]-2-(1-methyl-1H-pyrazol-4-yl)-6-[4-(trifluoromethoxy)phenyl]pyrimidine-4-carboxamide;
N-[(2S)-3-hydroxy-3-methylbutan-2-yl]-2-(1-methyl-1H-pyrazol-4-yl)-6-[4-(trifluoromethoxy)phenyl]pyrimidine-4-carboxamide;
N-[(3S,4S)-4-hydroxyoxolan-3-yl]-2-(1-methyl-1H-pyrazol-4-yl)-6-[4-(trifluoromethoxy)phenyl]pyrimidine-4-carboxamide;
N-(3,4-dihydroxybutan-2-yl)-2-(1-methyl-1H-pyrazol-4-yl)-6-[4-(trifluoromethoxy)phenyl]pyrimidine-4-carboxamide;
N-[(3R,4R)-4-hydroxyoxolan-3-yl]-2-(1-methyl-1H-pyrazol-4-yl)-6-[4-(trifluoromethoxy)phenyl]pyrimidine-4-carboxamide;
N-(3,3-difluoro-2-hydroxycyclohexyl)-2-(1-methyl-1H-pyrazol-4-yl)-6-[4-(trifluoromethoxy)phenyl]pyrimidine-4-carboxamide;
N-[(1S,2R)-2-hydroxycyclobutyl]-2-(1-methyl-1H-pyrazol-4-yl)-6-[4-(trifluoromethoxy)phenyl]pyrimidine-4-carboxamide;
N-[(1-hydroxycyclohexyl)methyl]-2-(1-methyl-1H-pyrazol-4-yl)-6-[4-(trifluoromethoxy)phenyl]pyrimidine-4-carboxamide;
N-[(1S,2R)-2-hydroxycyclohexyl]-2-(1-methyl-1H-pyrazol-4-yl)-6-[4-(trifluoromethoxy)phenyl]pyrimidine-4-carboxamide;
2-(1-methyl-1H-pyrazol-4-yl)-N-[(2R)-1,1,1-trifluoro-3-hydroxy-3-methylbutan-2-yl]-6-[4-(trifluoromethoxy)phenyl]pyrimidine-4-carboxamide;
N-[(3S,4R)-4-hydroxythiolan-3-yl]-2-(1-methyl-1H-pyrazol-4-yl)-6-[4-(trifluoromethoxy)phenyl]pyrimidine-4-carboxamide;
2-(1-methyl-1H-pyrazol-4-yl)-N-[(2R)-1,1,1-trifluoro-3-hydroxypropan-2-yl]-6-[4-(trifluoromethoxy)phenyl]pyrimidine-4-carboxamide;
N-[(1S,2R)-2-hydroxycyclohexyl]-2-(1-methyl-1H-pyrazol-4-yl)-6-[4-(trifluoromethoxy)phenyl]pyrimidine-4-carboxamide;
2-(1-methyl-1H-pyrazol-4-yl)-N-[(2S)-3,3,3-trifluoro-2-hydroxypropyl]-6-[4-(trifluoromethoxy)phenyl]pyrimidine-4-carboxamide;
2-(1-methyl-1H-pyrazol-4-yl)-N-(1,1,1-trifluoro-3-hydroxybutan-2-yl)-6-[4-(trifluoromethoxy)phenyl]pyrimidine-4-carboxamide;
N-[(2S)-1-hydroxypropan-2-yl]-2-(pyridin-3-yl)-6-[4-(trifluoromethyl)phenyl]pyrimidine-4-carboxamide;
N-[(2S)-1-hydroxy-3-methylbutan-2-yl]-2-(1-methyl-1H-pyrazol-4-yl)-6-[4-(trifluoromethoxy)phenyl]pyrimidine-4-carboxamide;
N-[(3S,4R)-4-hydroxyoxolan-3-yl]-2-(pyridin-3-yl)-6-[4-(trifluoromethoxy)phenyl]pyrimidine-4-carboxamide;
6-[4-(difluoromethyl)phenyl]-N-[(2S)-3-hydroxy-3-methylbutan-2-yl]-2-(pyridin-3-yl)pyrimidine-4-carboxamide; and
6-[4-(difluoromethyl)phenyl]-N-(2-hydroxy-2-methylpropyl)-2-(pyridin-3-yl)pyrimidine-4-carboxamide; or
a polymorph, an enantiomer, a diastereomer, a racemate, a tautomer, an N-oxide, a hydrate, or a solvate, a physiologically acceptable salt, or a solvate of a physiologically acceptable salt thereof.

3. A method of preparing a compound of formula (I) according to claim 1, said method comprising the step of reacting an intermediate compound of formula (VII):

(VII)

or a salt thereof, wherein X, Y, Z, R² and R⁴ are as defined for the compound of formula (I) according to claim 1, with a compound of formula (VIII):

H₂N—R¹ (VIII), in which R¹ is as defined for the compound of formula (I) according to claim 1, thereby giving a compound of formula (I):

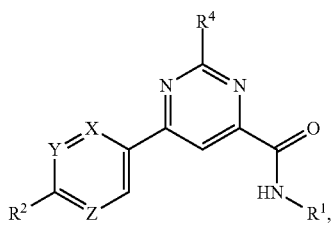

(I)

or a salt thereof, wherein X, Y, Z, R¹, R² and R⁴ are as defined for the compound of formula (I) according to claim 1.

4. A pharmaceutical composition comprising a compound of formula (I) according to claim 1, or a polymorph, an enantiomer, a diastereomer, a racemate, a tautomer, an N-oxide, a hydrate, or a solvate, a physiologically acceptable salt, or a solvate of a physiologically acceptable salt thereof, and one or more pharmaceutically acceptable excipients.

5. A pharmaceutical combination comprising:
one or more compounds of formula (I) according to claim 1, or a polymorph, an enantiomer, a diastereomer, a racemate, a tautomer, an N-oxide, a hydrate, or a solvate, a physiologically acceptable salt, or a solvate of a physiologically acceptable salt thereof, and
one or more pharmaceutically active anti cancer compounds or
one or more pharmaceutically active immune checkpoint inhibitors.

6. The compound of claim 1, or a salt thereof.

7. The compound of claim 2, or a physiologically acceptable salt thereof.

8. A compound of formula (VII):

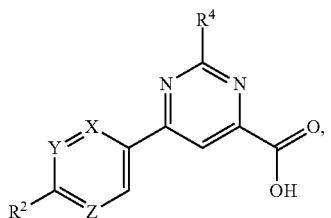

(VII)

or a salt thereof, wherein
X is CH;
Y is CR³;
Z is CH;

R² is chloro, difluoromethyl, trifluoromethyl, or trifluoromethoxy;
R³ is hydrogen;
R⁴ is a group selected from the group consisting of

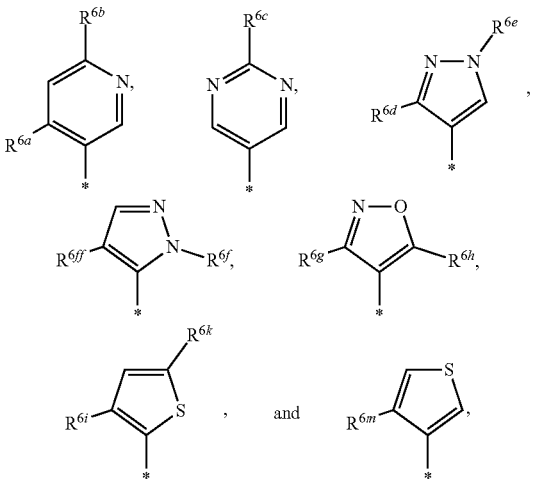

wherein * indicates the point of attachment of said group with the rest of the molecule;
$R^{6a}$ is hydrogen or methoxy;
$R^{6b}$ is hydrogen, methyl, methoxy, or cyano;
$R^{6c}$ is hydrogen, chloro, methyl, or cyano;
$R^{6d}$ is hydrogen or methyl;
$R^{6e}$ is hydrogen, methyl, isobutyl, or cyclopropyl;
$R^{6f}$ is hydrogen or methyl;
$R^{6ff}$ is hydrogen or methyl;
$R^{6g}$ is hydrogen or methyl;
$R^{6h}$ is hydrogen or methyl;
$R^{6i}$ is hydrogen or methyl;
$R^{6k}$ is hydrogen, chloro, or cyano; and
$R^{6m}$ is hydrogen or methyl.

9. A method for treatment of cancer, comprising administering a therapeutically effective amount of a compound of formula (I) according to claim 1, or a polymorph, an enantiomer, a diastereomer, a racemate, a tautomer, an N-oxide, a hydrate, or a solvate, a physiologically acceptable salt, or a solvate of a physiologically acceptable salt thereof, to a subject in need thereof.

10. The method according to claim 9, wherein the disease is a liquid tumour or a solid tumour.

11. The method according to claim 10, wherein the cancer is a solid tumour.

* * * * *